United States Patent
Attala et al.

(10) Patent No.: US 8,440,832 B2
(45) Date of Patent: May 14, 2013

(54) HETEROCYCLIC MODULATORS OF CANNABINOID RECEPTORS

(75) Inventors: Mohamed Naguib Attala, Houston, TX (US); Philippe Diaz, Missoula, MT (US)

(73) Assignee: Board of Regents, The University of Texas System, Austin, TX (US)

( * ) Notice: Subject to any disclaimer, the term of this patent is extended or adjusted under 35 U.S.C. 154(b) by 346 days.

(21) Appl. No.: 12/668,840

(22) PCT Filed: Jul. 14, 2008

(86) PCT No.: PCT/US2008/069977
§ 371 (c)(1),
(2), (4) Date: Mar. 2, 2010

(87) PCT Pub. No.: WO2009/012221
PCT Pub. Date: Jan. 22, 2009

(65) Prior Publication Data
US 2010/0204220 A1    Aug. 12, 2010

Related U.S. Application Data

(60) Provisional application No. 60/949,536, filed on Jul. 13, 2007, provisional application No. 61/036,321, filed on Mar. 13, 2008.

(51) Int. Cl.
*C07D 405/10* (2006.01)
*C07D 307/79* (2006.01)
*A61K 31/343* (2006.01)

(52) U.S. Cl.
USPC ........ 546/196; 514/233.5; 514/320; 514/459; 514/469; 544/153; 549/414

(58) Field of Classification Search
USPC ............... 546/197, 196; 514/320, 233.5, 459, 514/469; 544/153; 549/414
See application file for complete search history.

(56) References Cited

U.S. PATENT DOCUMENTS

| | | | |
|---|---|---|---|
| 5,684,002 | A | 11/1997 | Scherz et al. |
| 5,981,776 | A | 11/1999 | Diaz et al. |
| 2007/0099990 | A1 | 5/2007 | Ohkawa et al. |

FOREIGN PATENT DOCUMENTS

| | | |
|---|---|---|
| EP | 0816352 A1 | 2/2001 |
| WO | WO9729100 | 8/1997 |
| WO | WO9824778 | 6/1998 |
| WO | WO2006097193 | 9/2006 |

OTHER PUBLICATIONS

Diaz et al. "preparation of . . . " CA127:220571 (1997).*
Szlosek-Pinaud, M., et al., Efficient Synthetic Approach to Heterocycles Possessing the 3,3-Disubstituted-2,3-Dihydrobenzofuran Skeleton Via Diverse Palladium-Catalyzed Tandem Reactions, Tetrahedron, 2007, 63:3340-9.
Mukherjee, S., et al., Species Comparison and Pharmacological Characterization of Rat and Human CB2 Cannabinoid Receptors, Eur J Pharmacol, 2004, 505:1-9.
Kim, S.H., et al., An Experimental Model for Peripheral Neuropathy Produced by Segmental Spinal Nerve Ligation in the Rat, Pain, 1992,50:355-63.
Polomano, R.C., et al., A Painful Peripheral Neuropathy in the Rat Produced by the Chemotherapeutic Drug Paclitaxel, Pain, 2001, 94:293-304.
Chaplan, S.R., et al., Quantitative Assessment of Tactile Allodynia in the Rat Paw, J. Neurosci. Methods, 1994 53:55-63.
Dixon, W.J., The Up-and-Down Method for Small Samples, J. Am. Stat. Assoc., 1965, 60:967-78.
Hosohata, Y., et al., AM630 Antagonism of Cannabinoid-Stimulated [35S]GTP Gamma S Binding in the Mouse Brain, Eur. J. Pharmacol, 1997, 321:RI-3.
Ross, R.A., et al., Agonist-Inverse Agonist Characterization at CBI and CB2 Cannabinoid Receptors of L759633, L759656, and AM630, Br. J. Pharmacol., 1999, 126:665-72.
Gatley, S.J., et al., 123I-labeled AM25I: A Radioiodinated Ligand Which Binds in Vivo to Mouse Brain Cannabinoid CBI Receptors, Eur J Pharmacol, 1996, 307:331-8.
Ibrahim, M.M., Activation of CB2 Cannabinoid Receptors by AM124I Inhibits Experimental Neuropathic Pain: Pain Inhibition by Receptors Not Present in the CNS, Proc. Natl. Acad. Sci. U.S.A., 2003, 100:10529-33.
Ibrahim, M.M., et al., CB2 Cannabinoid Receptor Activation Produces Antinociception by Stimulating Peripheral Release of Endogenous Opioids, Proc. Natl. Acad. Sci. U.S.A., 2005, 102:3093-8.
Herzberg, U., et al., The Analgesic Effects of R(+)-WIN 55,212-2 Mesylate, a High Affinity Cannabinoid Agonist, in a Rat Model of Neuropathic Pain, Neurosci Lett, 1997, 221 :157-60.

Warms, C.A., et al., Treatments for Chronic Pain Associated with Spinal Cord Injuries: Many are tried, few are Helpful. Clin. J. Pain May-Jun 2002; 18 (3):154-63.
Matsuda, L.A., et. al., Structure of a Cannabinoid Receptor and Functional Expression of the Cloned cDNA. Nature Aug. 9, 1990; 346:561-4.
Munro, S., et. al., Molecular Characterization of a Peripheral Receptor for Cannabinoids. Nature 1993; 365:61-5.
Gaoni,Y., et al., Isolation, Structure, and Partial Synthesis of an Active Constituent of Hashish. J Am Chem Soc 1964; 86: 1646-7.
Di Marzo, V., et al., The Endocannabinoid System and Its Therapeutic Exploitation. Nat Rev Drug Discov 2004; 3:771-84.
Onaivi ,E.S., et al., Discovery of the Presence and Functional Expression of Cannabinoid CB2 Receptors in Brain. Ann NY Acad Sci 2006; 1074: 514-536.
Fride, E., Endocannabinoids in the Central Nervous System—An Overview. Prostaglandins Leukot Essent Fatty Acids 2002:66: 221-33.
Van Gaal, L.F. et al., Effects of the Cannabinoid-1 Receptor Blocker Rimonabant on Weight Reduction and Cardiovascular Risk Factors in Overweight Patients: 1-Year Experience From the RIO-Europe Study. The Lancet 2005; 365: 1389-1397.
Di Marzo, V.,et al., Leptin-Regulated Endocannabinoids Are Involved in Maintaining Food Intake. Nature 2001; 410: 822-5.
Maldonado, R.,et al., Involvement of the Endocannabinoid System in Drug Addiction. Trends Neurosci 2006; 29: 225-32.
Kehl, L.J.,et al., A Cannabinoid Agonist Differentially Attenuates Deep Tissue Hyperalgesia in Animal Models of Cancer and Inflammatory Muscle Pain. Pain 2003; 103: 175-86.
Idris, A.I., et al., Regulation of Bone Mass, Bone Loss And Osteoclast Activity by Cannabinoid Receptors. Nat Med 2005; 11: 774-9.
Maccarrone, M., et al., The Endocannabinoid System in Human Keratinocytes. Evidence That Anandamide Inhibits Epidermal Differentiation Through CB1 Receptor-Dependent Inhibition of Protein Kinase C, Activation Protein-1, and Transglutaminase. J Biol Chem 2003; 278: 33896-903.
Wilkinson ,J.D.,et al., Cannabinoids Inhibit Human Keratinocyte Proliferation Through a Non-CB1/CB2 Mechanism and Have a Potential Therapeutic Value in the Treatment of Psoriasis. J Dermatol Sci 2007; 45: 87-92.
Blazquez, C.,et al., Cannabinoid Receptors as Novel Targets for the Treatment of Melanoma. Faseb J 2006; 20: 2633-5.
Ferandin, Y.,et al., 3'-Substituted 7-Halogenoindirubins, A New Class of Cell Death Inducing Agents. J Med Chem 2006; 49: 4638-49.
Trang, T.,et al., Involvement of Cannabinoid (CbI)-Receptors in the Development and Maintenance of Opioid Tolerance. Neuroscience 2007; 146: I27~I288.
Teixeira-Clerc, F.,et al., CBI cannabinoid receptor antagonism: a new strategy for the treatment of liver fibrosis. Nat Med 2006; 12: 671-676.
Maresz, K.,et al., Direct Suppression of CNS Autoimmune Inflammation Via the Cannabinoid Receptor CbI on Neurons and CB2 on Autoreactive T Cells. Nat Med 2007; 13: 492-497.
Berghuis ,P.,et al., Hardwiring the Brain: Endocannabinoids Shape Neuronal Connectivity. Science 2007; 316: 1212-1216.
Kalsi ,V.,et al., Therapy Insight: Bladder Dysfunction Associated With Multiple Sclerosis. Nat Clin Pract Urol 2005; 2: 492-501.
Wang, H., et al., Aberrant Cannabinoid Signaling Impairs Oviductal Transport of Embryos. Nat Med 2004; 10: 1074~1080.
Kathuria, S., et al., Modulation of Anxiety Through Blockade of Anandamide Hydrolysis. Nat Med 2003; 9: 76-81.
Guzman M: Cannabinoids: Potential Anticancer Agents. Nature Reviews Cancer 2003; 3: 74~755.
Crowley, V.E.F., et al., Obesity Therapy: Altering the Energy Intake And-Expenditure Balance Sheet. Nature Reviews Drug Discovery 2002; 1: 276-286.
Baker, D.,et al., Cannabinoids Control Spasticity and Tremor in a Multiple Sclerosis Model. Nature 2000; 404: 8~87.
Steffens, S.,et al., Low Dose Oral Cannabinoid Therapy Reduces Progression of Atherosclerosis in Mice. Nature 2005; 434: 78~786.
Karsak, M., et al., Attenuation of Allergic Contact Dermatitis Through the Endocannabinoid System. Science 2007; 316: 1494-7.
Giblin, G.M.P., et. al., Discovery of a Selective CB 2 Receptor Agonist for the Treatment of Inflammatory Pain. Journal of Medicinal Chem. 2007, 50, 2597-2600.

Diaz, P., et. al., New Synthetic Retinoids Obtained by Palladium-Catalyzed Tandem Cyclisation-Hydride Capture Process. Tetrahedron 54(1998) 4579-4590.
Szlosek-Pinaud,M., et. al., Palladium-Catalyzed Allylation/Carbopalladation/Cross Coupling: A Novel Three-Component Ration for the Synthesis if 3,3-Disubstituted-2,3-Dihydrobenzfurans. Tetrahedron Letters 44 (2003) 8657-8659.
Pertwee, R.G., Cannbinoid Receptors and Pain., Progress in Neurobiology 63 (2001) 569-611.
Chevaleyre, V., et. al., Endocannabinoid-Mediated Synaptic Plasticity in the CNS. Ammu, Rev. Neurosci. 2006 29 37-79.
Vanecek, J., Cellular Mechanisms of Melatonin Action. Physiological Reviews vol. 78 (3) Jul. 1998, 687-721.

* cited by examiner

*Primary Examiner* — Celia Chang
(74) *Attorney, Agent, or Firm* — Tarolli, Sundheim, Covell & Tummino LLP

(57) ABSTRACT

Heterocyclic compounds which modulate cannabinoid receptors are presented. Pharmaceutical compositions containing these compounds, methods of using these compounds as modulators of cannabinoid receptors and processes for synthesizing these compounds are also described herein.

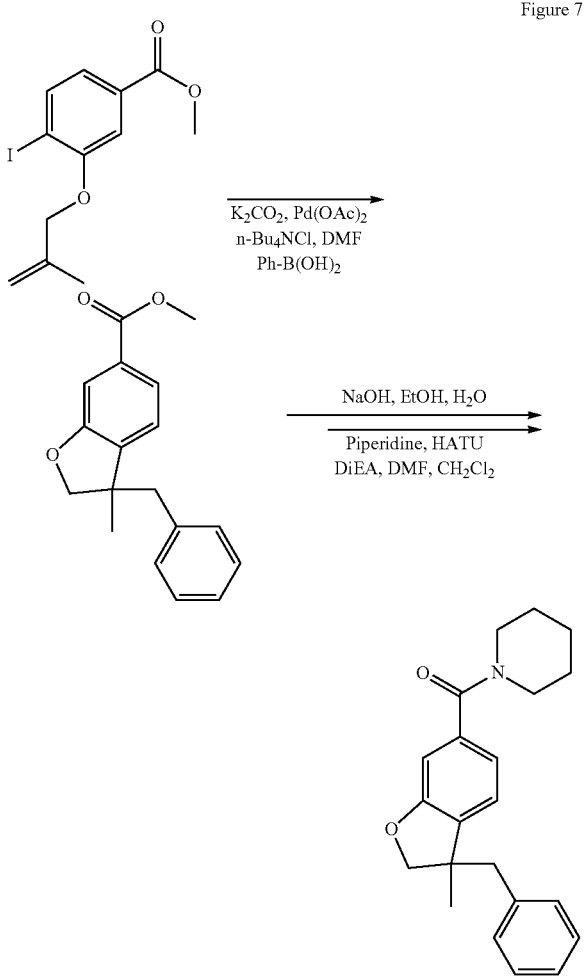

Figure 7

1 Claim, 20 Drawing Sheets

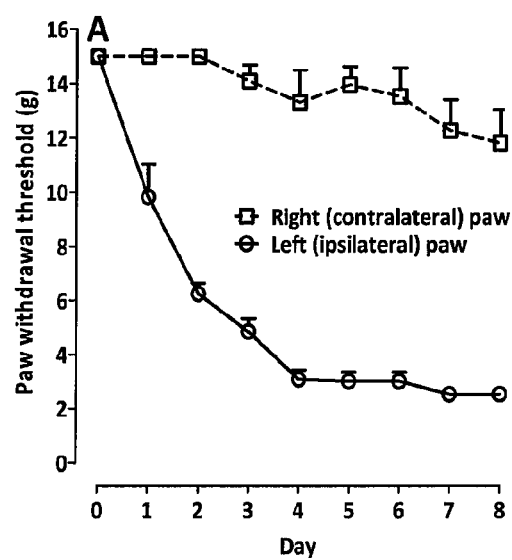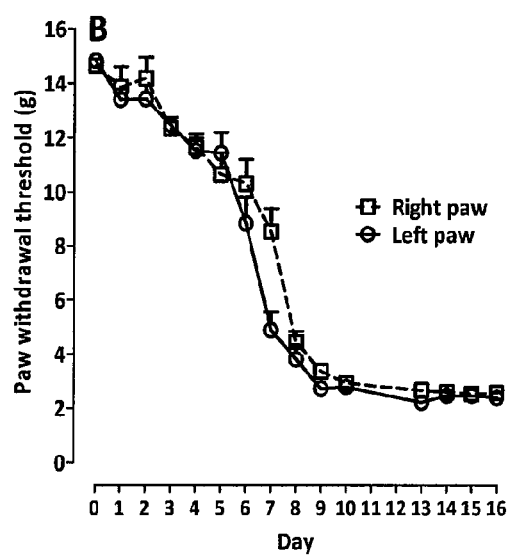
Figure 10A                    Figure 10B

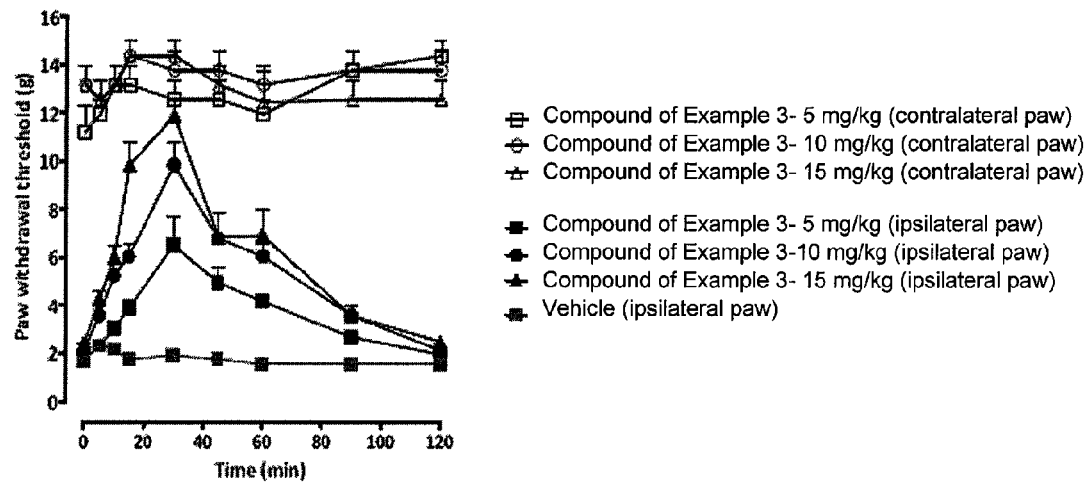
Figure 11A
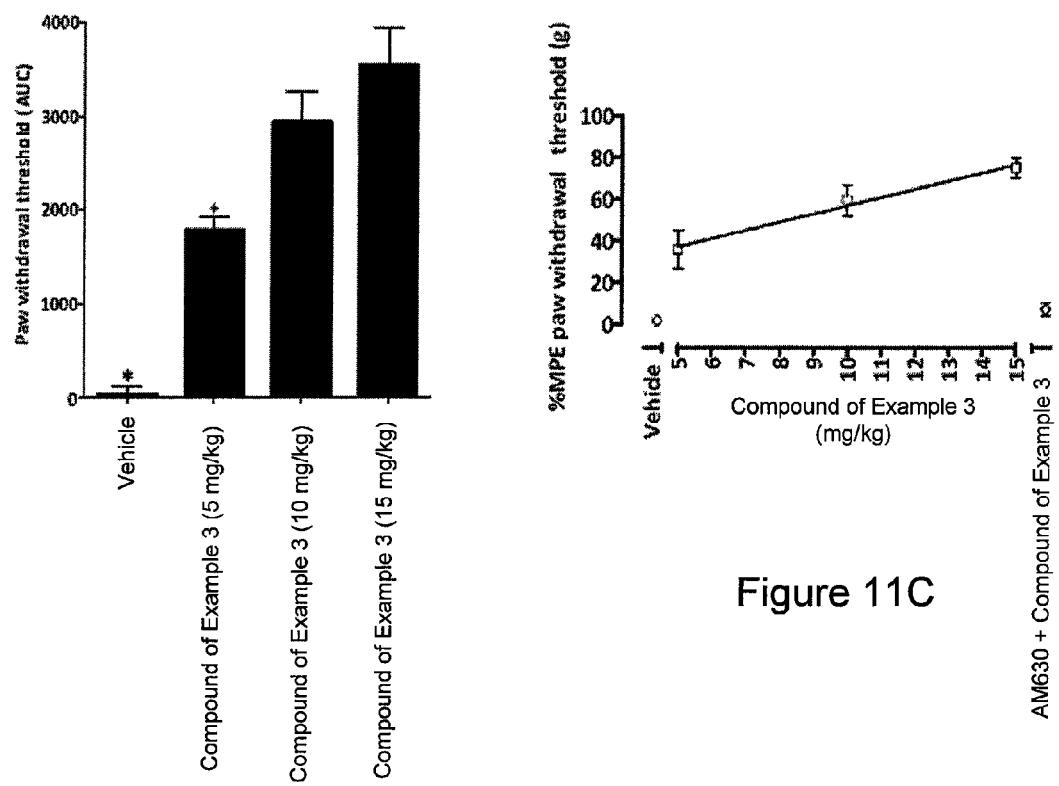
Figure 11B
Figure 11C

HETEROCYCLIC MODULATORS OF CANNABINOID RECEPTORS

CROSS-REFERENCE TO RELATED APPLICATIONS

This application claims priority to U.S. Pat. App. Ser. No. 60/949,536 filed Jul. 13, 2007 and to U.S. Pat. App. Ser. No. 61/036,321 filed Mar. 13, 2008. These applications are incorporated by reference herein it their entirety.

FIELD OF THE INVENTION

The present invention is directed to new heterocyclic compounds and compositions and their application as pharmaceuticals for the treatment of disease. Methods of modulating cannabinoid receptor activity in human or animal subject are provided for the treatment of diseases.

STATEMENT REGARDING FEDERALLY SPONSORED RESEARCH OR DEVELOPMENT

None.

THE NAMES OF THE PARTIES TO A JOINT RESEARCH AGREEMENT

None.

REFERENCE TO SEQUENCE LISTING

None.

BACKGROUND OF THE INVENTION

CB1 and CB2 are two cannabinoid receptors that belong to the GPCR family and have very different functions and distribution. While no x-ray structure is available for these receptors, various models have been described on the basis of the x-ray structure of rhodopsin, a GPCR belonging protein responsible of the light sensitivity in vision. Matsuda L A, Lolait S J, Brownstein M J, Young A C, Bonner T I, *Structure of a Cannabinoid Receptor and Functional Expression of the Cloned cDNA*, Nature 1990, 346:561-4. CB1 is abundantly expressed in the central nervous system and is most dense in the basal ganglia, cerebellum, hippocampus, and cortex and in the peripheral nervous system, it is expressed in such sites as the testis, eye, urinary bladder, and adipocytes. CB2 is mainly expressed in the immune tissues, in cells such as those in the thymus, marrow, spleen, pancreas, and in glioma and skin tumor cells. It was recently demonstrated that CB2 receptors and their gene transcripts are widely distributed in the brain. A third cannabinoid receptor seems to be present as some chemical analogues exhibit cannabinoid biological activity without activating CB1 and CB2. Di Marzo V, Bifulco M, De Petrocellis L, *The Endocannabinoid System and Its Therapeutic Exploitation*, Nat Rev Drug Discov 2004, 3:771-84.

BRIEF SUMMARY OF THE INVENTION

Novel heterocyclic compounds and pharmaceutical compositions that modulate CB1 and CB2 have been found, together with methods of synthesizing and using the compounds including methods for the treatment of cannabinoid receptor-mediated diseases in a patient by administering the compounds.

A class of heterocyclic compounds, useful in treating cannobinoid receptor mediated disorders and conditions, is presented and defined by the structural Formula I:

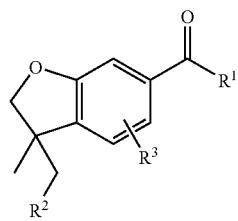

or a salt, ester or prodrug thereof, wherein:
  $R^1$ is selected from the group consisting of $NH_2$, $NHR^4$, $NR^4R^5$, any carbon atom of which may be optionally substituted;
  $R^2$ is selected from the group consisting of hydrogen, aryl, alkyl, cycloalkyl, aralkyl, alkenyl, and alkynyl, any carbon atom of which may be optionally substituted;
  $R^3$ is selected from the group consisting of hydrogen, halogen, alkyl, cycloalkyl, heterocycloalkyl, aryl, and heteroaryl, any carbon atom of which may be optionally substituted; and
  $R^4$ and $R^5$ vary independently and are selected from the group consisting of aryl, alkyl, cycloalkyl, aralkyl, alkenyl, and alkynyl, any carbon atom of which may be optionally substituted,
and by the structural Formula III:

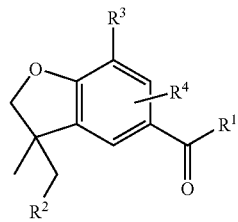

or a salt, ester or prodrug thereof, wherein:
  $R^1$ is selected from the group consisting of $NH_2$, $NHR^5$, $NR^5R^6$, any carbon atom of which may be optionally substituted;
  $R^2$ is selected from the group consisting of hydrogen, aryl, alkyl, cycloalkyl, aralkyl, alkenyl, and alkynyl, any carbon atom of which may be optionally substituted;
  $R^3$ and $R^4$ are independently selected from the group consisting of hydrogen, halogen, alkyl, cycloalkyl, heterocycloalkyl, aryl, and heteroaryl;
  $R^5$ and $R^6$ are independently selected from the group consisting of aryl, alkyl, cycloalkyl, aralkyl, alkenyl, and alkynyl; and
  when $R^2$ is hydrogen, $R^3$ is not t-butyl, bromo, methoxy, or

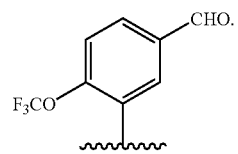 [SMILES: *c1cc(C=O)ccc1OC(F)(F)F]

Heterocyclic compounds presented herein possess useful cannabinoid receptor modulating activity, and may be used in the treatment or prophylaxis of a disease or condition in which a cannabinoid receptor plays an active role. Thus, in broad aspect, pharmaceutical compositions are provided comprising one or more the compounds together with a pharmaceutically acceptable carrier, as well as methods of making and using the compounds and compositions.

Methods for modulating cannabinoid receptors with heterocyclic compounds are also provided. Methods for treating a cannabinoid receptor-mediated disorder such as neuropathic pain or addiction in a patient in need of such treatment comprising administering to said patient a therapeutically effective amount of a heterocyclic compound or composition presented herein. The use of compounds disclosed herein can be used in the manufacture of a medicament for the treatment of a disease or condition ameliorated by the modulation of cannabinoid receptors.

BRIEF DESCRIPTION OF SEVERAL VIEWS OF THE DRAWINGS

The foregoing summary as well as the following detailed description of the preferred embodiment of the invention will be better understood when read in conjunction with the appended drawings. It should be understood, however, that the invention is not limited to the precise arrangements and instrumentalities shown herein.

For a more complete understanding of the present invention, and the advantages thereof, reference is now made to the following descriptions taken in conjunction with the accompanying drawings, in which:

FIG. 10A depicts the development of tactile allodynia after spinal nerve ligation. FIG. 10B depicts development of tactile allodynia after i.p. administration of paclitaxel for 4 days. Each point represents the mean±s.e. mean.

FIGS. 11A, 11B and 11C show the effects of compound of Example 3 (i.p) on tactile allodynia in a spinal nerve ligation neuropathic pain model in contralateral normal, ipsilateral injured rats (n=6 per group). Compound of Example 3 increases in the withdrawal threshold of the nerve-injured paw in a dose-dependent manner. FIG. 11A shows the time course of 5.0, 10, and 15 mg/kg of the compound of Example 3. FIG. 11B shows the area under the curve (AUC). FIG. 11C shows the dose response curve of the anti-allodynic effects the compound of Example 3 at 30 min in a spinal nerve ligation neuropathic pain model ($ED_{50}$=7.48 (CI 5.6-9.9) mg/kg, i.p.). Pretreatment with 5 mg/kg i.p. of a selective CB2 antagonist AM630 antagonized the effects of the compound of Example 3. Data are expressed as mean±s.e. mean. *P<0.001 versus all other groups. $^{+}$P<0.05 versus 10 mg/kg and 15 mg/kg of the compound of Example 3.

FIG. 14A shows the compound of Example 3 suppressed paclitaxel-evoked thermal hyperalgesia in a dose-dependent manner. In the AM630+ the compound of Example 3 group, pretreatment with 5 mg/kg AM630 i.p. followed 15 min later by 15 mg/kg of the compound of Example 3i.p. reversed the anti-hyperalgesic effects of the compound of Example 3 (P<0.001). The effect of 5 mg/kg AM1241 i.p. on reversing thermal hyperalgesia was significantly less than (P<0.05) that noted for 15 mg/kg the compound of Example 3i.p. FIG. 14B shows the calculated $ED_{so}$ of the compound of Example 3 for suppressing thermal hyperalgesia at 20 min was 13.5 mg/kg i.p. (95% CI=8.2-22 mg/kg). FIG. 14C shows the compound of Example 3 dose-dependently attenuated tactile allodynia in this model. FIG. 14D shows an increase in the % MPE withdrawal threshold AUC with an $ED_{50}$ of 24 mg/kg i.p. *P<0.05 or less as compared to 5 mg/kg, 10 mg/kg, and 15 mg/kg the compound of Example 3 groups. $^{+}$P<0.05 or less as compared 15 mg/kg the compound of Example 3 group. **P<0.05 or less as compared to 10 mg/kg, and 15 mg/kg the compound of Example 3 groups.

DETAILED DESCRIPTION OF THE INVENTION

Figure 1A:
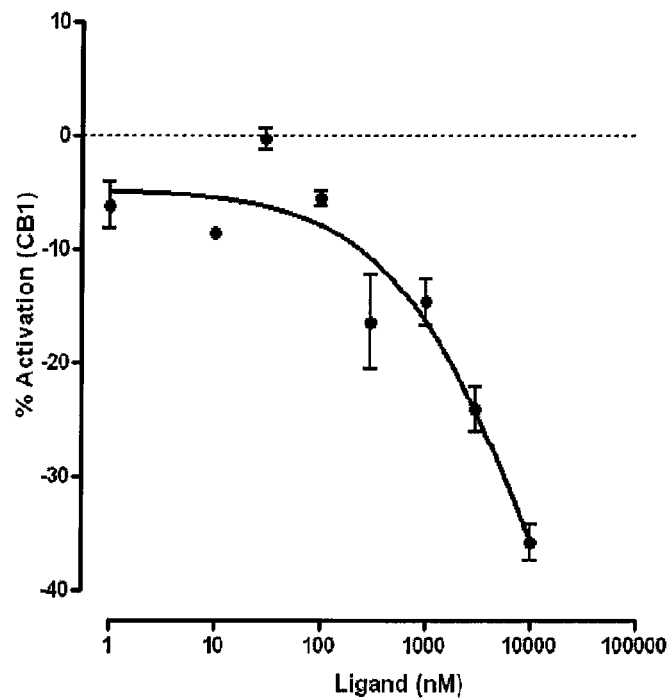
FIGS. 1A and 1B show functional activity data of the compound of Example 2.
Figure 1B:
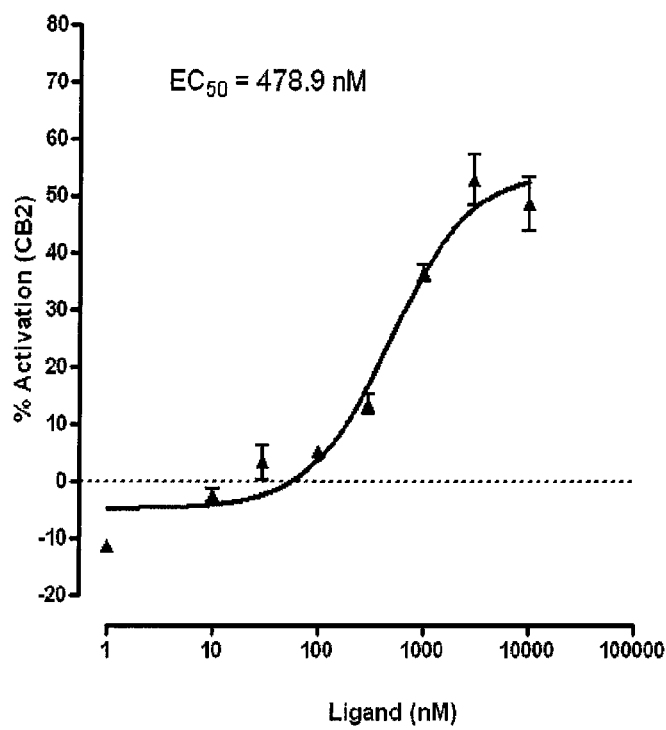
Figure 2A:
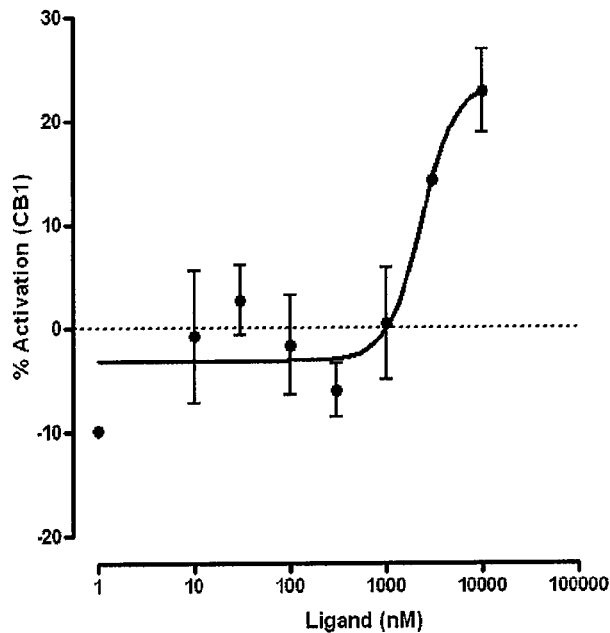
FIGS. 2A and 2B show functional activity data of the compound of Example 3.
Figure 2B:
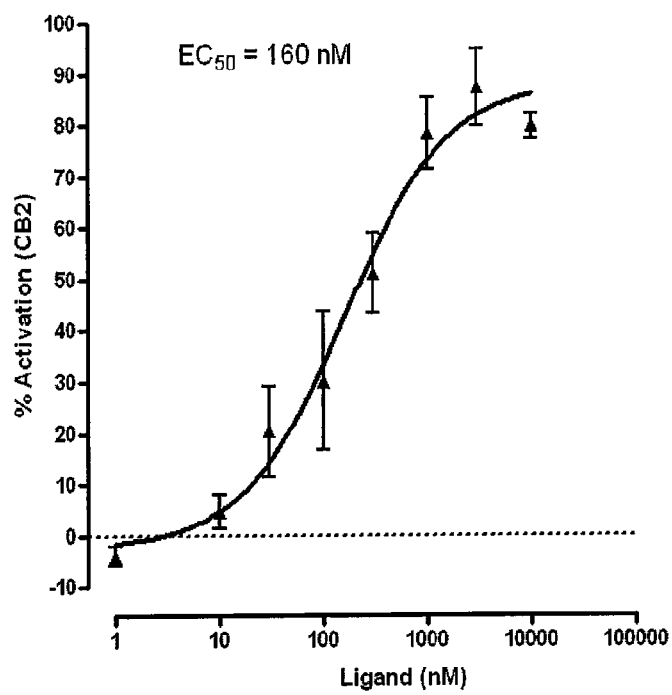
Figure 3A:
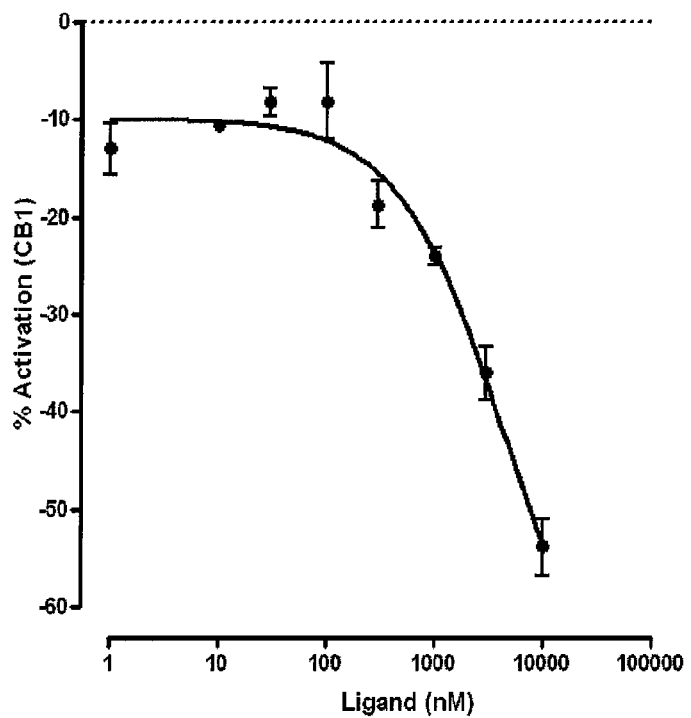
FIGS. 3A and 3B show functional activity data of the compound of Example 5.
Figure 3B:
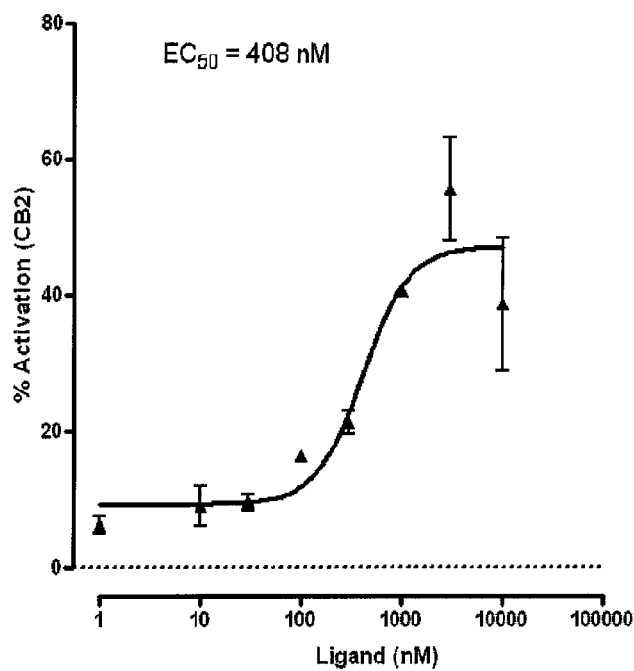

Novel compounds presented include compounds defined by the structural Formula II:

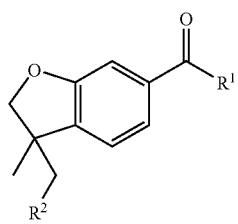

or a salt, ester or prodrug thereof, wherein:
$R^1$ is selected from the group consisting of $NH_2$, $NHR^3$, $NR^3R^4$, any carbon atom of which may be optionally substituted;

$R^2$ is selected from the group consisting of hydrogen, aryl, alkyl, cycloalkyl, aralkyl, alkenyl, and alkynyl, any carbon atom of which may be optionally substituted; and
$R^3$ and $R^4$ are independently selected from the group consisting of aryl, alkyl, cycloalkyl, heterocycloalkyl, aralkyl, alkenyl, and alkynyl, any carbon atom of which may be optionally substituted,
and by the structural Formula IV:

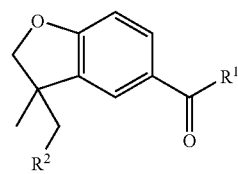

or a salt, ester or prodrug thereof, wherein:
$R^1$ is selected from the group consisting of $NH_2$, $NHR^3$, $NR^3R^4$, any carbon atom of which may be optionally substituted;
$R^2$ is selected from the group consisting of hydrogen, aryl, alkyl, cycloalkyl, aralkyl, alkenyl, and alkynyl, any of carbon atom of which may be optionally substituted;
$R^3$ and $R^4$ are independently selected from the group consisting of aryl, alkyl, cycloalkyl, heterocycloalkyl, aralkyl, alkenyl, and alkynyl, any carbon atom of which may be optionally substituted; and
when $R^2$ is hydrogen, $R^1$ is not $NH_2$,

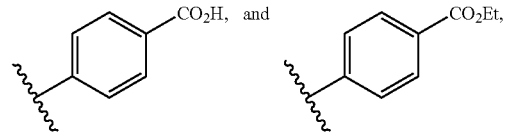

and by the structural Formula V:

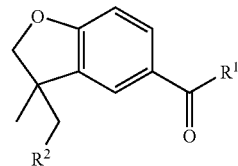

or a salt, ester or prodrug thereof, wherein:
$R^1$ is selected from the group consisting of cyclohexylamino, piperidinyl, and o-iodoanilino; and
$R^2$ is optionally substituted phenyl,
and by the structural Formula VI:

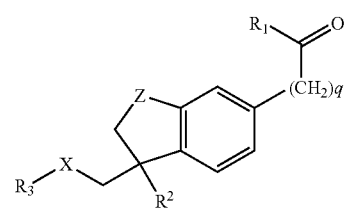

or a salt, ester or prodrug thereof, wherein:

q is an integer ranging from 0 to 2

X is absent or present and represents a —O—, —S—, —Se—, NR$^6$, SO—, —SO$_2$—,

Z represents a —O—, —S—, —SO—, —SO$_2$—, —Se— or NR$^7$

R$^1$ is selected from the group consisting of NH$_2$, NHR$^4$, NR$^4$R$^5$, aryl, a heteroaryl alkyl, cycloalkyl, aralkyl, alkenyl, and alkynyl, any carbon atom of which may be optionally substituted R$^2$ is selected from the group consisting of hydrogen, alkyl, cycloalkyl, aralkyl, alkenyl, and alkynyl an alkoxyl, any carbon atom of which may be optionally substituted;

R$^3$ is selected from the group consisting of aryl, a heteroaryl, alkyl, cycloalkyl, heterocycloalkyl, aralkyl, alkenyl, and alkynyl, any carbon atom of which may be optionally substituted;

R$^4$ and R$^5$ vary independently and are selected from the group consisting of aryl, alkyl, cycloalkyl, aralkyl, alkenyl, and alkynyl, any carbon atom of which may be optionally substituted, R$^6$ is selected from the group consisting of hydrogen, aryl, alkyl, cycloalkyl, aralkyl, alkenyl, and alkynyl, any carbon atom of which may be optionally substituted, R$^7$ is selected from the group consisting of hydrogen, aryl, alkyl, cycloalkyl, aralkyl, alkenyl, and alkynyl, any carbon atom of which may be optionally substituted.

Novel compounds presented further include compounds defined by the structural Formula VII:

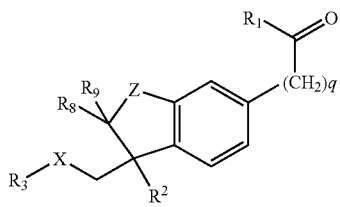

or a salt, ester or prodrug thereof, wherein:

q is an integer ranging from 0 to 2

X is absent or present and represents a —O—, —S—, —Se—, NR$^6$, SO—, —SO$_2$—,

Z represents a —O—, —S—, —SO—, —SO$_2$—, —Se— or NR$^7$

R$^1$ is selected from the group consisting of NH$_2$, NHR$^4$, NR$^4$R$^5$, aryl, a heteroaryl alkyl, cycloalkyl, aralkyl, alkenyl, and alkynyl, any carbon atom of which may be optionally substituted R$^2$ is selected from the group consisting of hydrogen, alkyl, cycloalkyl, aralkyl, alkenyl, and alkynyl an alkoxyl, any carbon atom of which may be optionally substituted;

R$^3$ is selected from the group consisting of aryl, a heteroaryl, alkyl, cycloalkyl, heterocycloalkyl, aralkyl, alkenyl, and alkynyl, any carbon atom of which may be optionally substituted;

R$^4$ and R$^5$ vary independently and are selected from the group consisting of aryl, alkyl, cycloalkyl, aralkyl, alkenyl, and alkynyl, any carbon atom of which may be optionally substituted, R$^6$ is selected from the group consisting of hydrogen, aryl, alkyl, cycloalkyl, aralkyl, alkenyl, and alkynyl, any carbon atom of which may be optionally substituted, R$^3$ and R$^6$ taken together might form a cycloalkyl containing from 3 to 10 carbon atoms and eventually interrupted with one or more hetero atoms or by —CO—, —SO—, —SO$_2$—, —CHOH— or —NR$^{13}$—;

R$^7$ is selected from the group consisting of hydrogen, aryl, alkyl, cycloalkyl, aralkyl, alkenyl, and alkynyl, any carbon atom of which may be optionally substituted, R$^8$ and R$^9$ are selected from the group consisting of hydrogen, alkyl, an alkoxyl or taken together might form a carbonyl.

As used herein, the terms below have the meanings indicated.

The term "acyl," as used herein, alone or in combination, refers to a carbonyl attached to an alkenyl, alkyl, aryl, cycloalkyl, heteroaryl, heterocyclyl, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20, preferably 2 to 6, carbon atoms. Alkenylene refers to a carbon-carbon double bond system attached at two or more positions such as ethenylene [(CH=CH—), (—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::

C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(═O)—NR$_2$ group with R as defined herein. The term "N-amido" as used herein, alone or in combination, refers to a RC(═O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term "aryloxy," as used herein, alone or in combination, refers to an aryl group attached to the parent molecular moiety through an oxy.

According to the present invention, the expression alkyl radicals understood to mean a linear optionally branched and optionally fluorinated radical. In certain embodiments, alkyl radicals having from 6 to 12 carbon atoms are 2-Methylpentan-2-yl, 3,3-Dimethyl-butan-1-yl, hexyl, heptyl, octyl, nonyl, decyl, dodecyl. "Alkyl radicals" containing from 1 to 3 carbon atoms, are linear or branched radicals containing, respectively, from 1 to 3. Preferably, the alkyl radicals containing from 1 to 3 carbon atoms are methyl, ethyl, n-propyl, or 2-propyl radicals. The expression "alkoxyl radical" is understood to mean a radical containing from 1 to 3 carbon atoms, such as methoxyl, ethoxyl, propyloxyl or isopropyloxyl radicals.

The term "aryl radical" means a phenyl or a naphthyl radical, eventually mono- or disubstituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The term "heteroaryl" means an aryl radical interrupted with one or more hetero atoms, such as a thiophenyl, thiazolyl or imidazolyl radical, optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 6 carbon atoms.

The term "polyether radical" means a polyether radical containing from 2 to 6 carbon atoms interrupted with at least one oxygen atom, such as methoxymethoxy, ethoxymethoxy or methoxyethoxymethoxy radicals.

The term "halogen atom" includes, but is not limited to, fluorine, chlorine or bromine atom.

The terms "benzo" and "benz," as used herein, alone or in combination, refer to the divalent radical C$_6$H$_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic heterocyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocyclyl," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particuar moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R$^{41}$ where n=(1, 2, 3, . . . n), every substituent, and every term should be understood to be independent of every other in terms of selection from a group. Should any variable, substituent, or term (e.g. aryl, heterocyclyl, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two kinds of optical isomers. The first optical isomer are compounds that are mirror images of one another but cannot be superimposed on each other. These isomers are called "enantiomers". The second optical isomers are molecules that are not mirror images but each molecule rotates plane polarized light and are considered optically active. Such molecules are called "diastereoisomers". Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"Cannabinoid receptor modulator" is used herein to refer to a compound that exhibits an $EC_{50}$ or $IC_{50}$ with respect to a cannabinoid receptor activity of no more than about 100 μM and more typically not more than about 50 μM, as measured in the cannabinoid receptor assay described generally herein below. "$EC_{50}$" is that concentration of modulator which activates the activity of a cannabinoid receptor to half-maximal level. "$IC_{50}$" is that concentration of modulator which reduces the activity of a cannabinoid receptor to half-maximal level. This test will be done during the exemplification period.

The term "modulator" described herein reflects any chemical compound that will act as full agonist, partial agonist, inverse agonist or as an antagonist at any known or yet to be discovered/identified cannabinoid receptor.

Compounds described herein have been discovered to exhibit modulatory activity against cannabinoid receptors and exhibit an $EC_{50}$ or $IC_{50}$ with respect to a cannabinoid receptor of no more than about 10 μM, more preferably, no more than about 5 μM, even more preferably not more than about 1 μM, and most preferably, not more than about 200 nM, as measured in the assays described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds of the present invention may also exist as prodrugs, as described in *Hydrolysis in Drug and Prodrug Metabolism: Chemistry, Biochemistry, and Enzymology*, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds of the present invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich, *Pharmaceutical Salts: Properties, Selection, and Use*, Wiley-VCHA, Zurich, Switzerland, 2002.

The term "therapeutically acceptable salt," as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described in this patent could be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic nontoxic bases include salts of primary, secondary, and tertiary amines, substituted amines including naturally occurring substituted amines, cyclic amines, and basic ion exchange resins, such as argmine, betaine, caffeine, choline, ethylamine, 2-diethylaminoethano, 1,2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the novel compounds described in this patent are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds of the subject invention to be administered as the raw chemical, it is also possible to present them as a pharmaceutical formulation. Accordingly, the subject invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

One example of a formulation appropriate for administration through an oral route comprises 0.60 g of the compound of Example 16, 10.00 g of NMP, 64.40 g of LABRAFIL® M1944 CS, and 25.00 g of LABRASOL®.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

One example of a formulation appropriate for administration through a parenteral route comprises 1.00 g of the compound of Example 3, 30.00 g of NMP, 30.00 g of propylene glycol, 10.00 g of CREMOPHOR® ELP, 10.00 g of EtOH (95%), and 19.00 g of saline solution.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Compounds of the present invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include solid, liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.01% to 1% w/w of the formulation.

Via the topical route, the pharmaceutical composition according to the invention is more particularly intended for treating the skin and mucous membranes and may be in the form of liquid or semi liquid such as ointments, creams or in the form of solid such as powders. It may also be in the form of suspensions such as polymeric microspheres or polymer patches and hydrogels allowing a controlled release. This topical composition may be in anhydrous form, in aqueous form or in the form of an emulsion. The compounds are used topically at a concentration generally of between 0.001% and 10% by weight and preferably between 0.01% and 1% by weight, relative to the total weight of the composition.

One example of a formulation appropriate for administration through a topical route comprises 3.00 g of the compound of Example 13, 35.00 g of NMP, 25.00 g of LABRASOL®, 15.00 g of oleic acid, 12.00 g of COMPRITOL® 888 ATO, and 10.00 g of EtOH.

The compounds presented herein may also find an application in cosmetics, in particular in body and hair hygiene and more particularly for regulating and/or restoring skin lipid metabolism.

Cosmetic use of a composition comprising, in a physiologically acceptable support, at least one of the compounds described herein for body or hair hygiene are presented. The cosmetic composition, in a cosmetically acceptable support, at least one compound and/or an optical or geometrical isomer thereof or a salt thereof, and may be in the form of liquid or semi liquid such as ointments, creams or in the form of solid such as powders. It may also be in the form of suspensions such as polymeric microspheres or polymer patches and hydrogels allowing a controlled release. This topical composition may be in anhydrous form, in aqueous form or in the form of an emulsion. The concentration of compound in the cosmetic composition is between 0.001% and 5% by weight relative to the total weight of the composition. Finally, a subject of the present invention is a cosmetic process for enhancing the skin, which consists in applying to the skin a composition comprising at least one compound presented herein.

For administration by inhalation, the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

Certain compounds according to the invention can be administered at a daily dose of about 0.001 mg/kg to 100 mg/kg of body weight, in 1 to 3 dosage intakes. Further, certain compounds can be used systemically, at a concentration generally of between 0.001% and 10% by weight and preferably between 0.01% and 1% by weight, relative to the weight of the composition.

The amount of active ingredient that may be combined with the carrier materials to produce a single dosage form will vary depending upon the host treated and the particular mode of administration.

The compounds of the subject invention can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the heterocyclic compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention together with inert or active compounds, or other drugs including wetting agents, flavour enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or anti-acne agents, such as benzoyl peroxide, antibiotics, for instance erythromycin and tetracyclines, antifungal agents such as ketoconazole, agents for promoting regrowth of the hair, for instance Minoxidil (2,4-diamino-6-piperidinopyrimidine 3-oxide), non-steroidal anti-inflammatory agents, carotenoids, and especially p-carotene, antipsoriatic agents such as anthralin and its derivatives, retinoids, i.e. RAR or RXR receptor ligands, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenyloin and the like and mixtures or pharmaceutically acceptable salts thereof. Needless to say, a person skilled in the art will take care to select the other compound(s) to be added to these compositions such that the advantageous properties intrinsically associated with the heterocyclic compound are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating cannabinoid receptor-mediated disorders in a human or animal subject in need of such treatment are presented herein, the methods comprising the step of administering to a subject in need thereof an amount of a heterocyclic compound effective to reduce or prevent a disorder in combination with at least one additional agent for the treatment of said disorder that is known in the art.

In a related aspect, therapeutic compositions having at least one novel heterocyclic compound described herein can be administered in combination with one or more additional agents for the treatment of cannabinoid-mediated disorders.

Furthermore, methods of treatment of certain diseases and indications in a human or animal subject in need of such treatment are provided herein. Heterocyclic compounds described herein can be used alone or in combination with other agents and compounds in the treatment of neuropathic pain, addiction (including nicotine, cocaine, opioids, hashish, marijuana, alcohol dependence, food), cancer (including melanoma, lymphomas, and gliomas), inflammation including autoimmune inflammation, cardiovascular disease, liver fibrosis, obesity, osteoporosis and other bone disease. Additional indications for use of the compounds disclosed herein include acne, psoriasis, allergic contact dermatitis, anxiety, spasticity and tremor, bladder dysfunctions, prevention of miscarriage and ectopic pregnancy, Tourette's, Parkinson's disease, stroke, glaucoma and other diseases of the eye including intraocular pressure, diarrhea and nausea. Each such treatment described above includes the step of administering to a subject in need thereof a therapeutic effective amount of the heterocyclic compound described herein to reduce or prevent such disease or indication.

Besides being useful for human treatment, the compounds and formulations of the present invention are also useful for veterinary treatment of companion animals, exotic animals and farm animals, including mammals, rodents, and the like.

More preferred animals include horses, dogs, and cats. These heterocyclic compounds are also helpful in neuronal growth and development.

Therefore, the compounds described herein may be used alone or in combination with another agent or compound in methods for treating, ameliorating or preventing a syndrome, disorder or disease in which cannabinoid receptor is involved, including, but not limited to, ocular complaint such as glaucoma, pain, controlling appetite, regulating metabolism, diabetes, social and mood disorders, seizure-related disorders, substance abuse disorders, learning, cognition and/or memory disorders, bowel disorders, gastrointestinal disorders, respiratory disorders, locomotor activity disorders, movement disorders, immune disorders or inflammation disorders, and controlling organ contraction and muscle spasm.

The compounds presented herein may be also useful in enhancing learning, cognition and/or memory, regulating cell growth, providing neuroprotection and the like. The compounds presented herein may also be used for treating dermatological complaints associated with a keratinization disorder relating to cell differentiation and proliferation, especially for treating acne, for treating other dermatological complaints with or without cell proliferation disorder, and especially all forms of psoriasis, for treating all dermal or epidermal proliferations, for preventing or treating cicatrization disorders, in the treatment of dermatological or general complaints with an immunological component, in the treatment of skin disorders caused by exposure to UV radiation, and also for combating sebaceous function disorders, for repairing or combating ageing of the skin, for preventing or treating cicatrization disorders, in the treatment of pigmentation disorders.

Historically, cannabinoid preparations have been used for medicinal and recreational purposes for many centuries. Cannabinoids are present in the hemp Cannabis sativa L. Identification of the main active ingredient, tetrahydrocannabinol (Δ9-THC) has been done in 1964. Gaoni Y, Mechoulam R, *Isolation, Structure, and Partial Synthesis of an Active Constituent of Hashish*, J Am Chem Soc 1964, 86:1646-7. The endocannabinoid system was elucidated in the early 1990's. Currently, two receptors belonging to the GPCR family CB1 and CB2, five endogenous lipid ligands and the enzymes involved in their syntheses and metabolism have been identified. Matsuda L A, Lolait S J, Brownstein M J, Young A C, Bonner T I, *Structure Of A Cannabinoid Receptor And Functional Expression Of The Cloned Cdna*, Nature 1990, 346: 561-4.

CB1 is abundantly expressed in the central nervous system with highest density level in the basal ganglia, cerebellum, hippocampus and cortex as well as in the peripheral nervous system such as testis, eye, urinary bladder and adipocyte. CB2 is mainly expressed in the immune tissues and cells such as the thymus, marrow, spleen, pancreas and in glioma and skin tumor cells.

CB2 receptors and their gene transcripts have been recently demonstrated as widely distributed in the brain. The multifocal expression of CB2 immunoreactivity in brain suggests that CB2 receptors play a role in the brain and may be involved in depression and substance abuse. See e.g., Onaivi E S, Ishiguro H, Gong J-P, Patel S, Perchuk A, Meozzi P A, Myers L, Mora Z, Tagliaferro P, Gardner E, Brusco A, Akinshola B E, Liu Q-R, Hope B, Iwasaki S, Arinami T, Teasenfitz L, Uhl G R, *Discovery of the Presence and Functional Expression of Cannabinoid CB2 Receptors in Brain*, Ann NY Acad Sci 2006, 1074:514-536; Berghuis P, Rajnicek A M, Morozov Y M, Ross R A, Mulder J, Urban G M, Monory K, Marsicano G, Matteoli M, Canty A, Irving A J, Katona I, Yanagawa Y, Rakic P, Lutz B, Mackie K, Harkany T, *Hardwiring the Brain: Endocannabinoids Shape Neuronal Connectivity*, Science 2007, 316:1212-1216; Kalsi V, Fowler C J, *Therapy Insight: Bladder Dysfunction Associated With Multiple Sclerosis*, Nat Clin Pract Urol 2005, 2:492-501; Kathuria S, Gaetani S, Fegley D, Valino F, Duranti A, Tontini A, Mor M, Tarzia G, Rana G L, Calignano A, Giustino A, Tattoli M, Palmery M, Cuomo V, Piomelli D, *Modulation of Anxiety Through Blockade of Anandamide Hydrolysis*, Nat Med 2003, 9: 76-81; Baker D, Pryce G, Croxford J L, Brown P, Pertwee R G, Huffman J W, Layward L, *Cannabinoids Control Spasticity and Tremor in a Multiple Sclerosis Model*, Nature 2000, 404:84-87. Furthermore, the endocannabinoid system has been implicated in allergic contact dermatitis. Karsak M, Gaffal E, Date R, Wang-Eckhardt L, Rehnelt J, Petrosino S, Starowicz K, Steuder R, Schlicker E, Cravatt B, Mechoulam R, Buettner R, Werner S, Di Marzo V, Tuting T, Zimmer A, *Attenuation of Allergic Contact Dermatitis Through the Endocannabinoid System*, Science 2007, 316: 1494-7.

In addition, studies provide support for the role of cannabinoid system in several physiological functions including food consumption and body weight, in which CB1 receptor activation leads to increased food consumption and weight gain. Fride, E., *Endocannabinoids in the Central Nervous System—an Overview*, Prostaglandins Leukot Essent Fatty Acids 2002, 66:221-33. Subsequently, CB1 receptor blockade reduces food consumption and leads to weight loss. Van Gaal L F, Rissanen A M, Scheen A J, Ziegler O, Rossner S, *Effects Of The Cannabinoid-1 Receptor Blocker Rimonabant On Weight Reduction And Cardiovascular Risk Factors In Overweight Patients: 1-Year Experience From The RIO-Europe Study*, The Lancet 2005, 365:1389-1397.

Modulators of CB1/CB2 receptors have been used in different clinical or preclinical studies. Steffens S, Veillard N R, Arnaud C, Pelli G, Burger F, Staub C, Zimmer A, Frossard J-L, Mach F, *Low Dose Oral Cannabinoid Therapy Reduces Progression of Atherosclerosis in Mice*, Nature 2005, 434: 782-786. For example, CB1 agonists have been used for treatment of nausea, Tourette's, Parkinson's disease, glaucoma, cancer, diarrhoea, and stroke. Guzman M, *Cannabinoids: Potential Anticancer Agents*, Nature Reviews Cancer 2003, 3:745-755. Further, CB2 agonists have been used for treatment pain, gliomas, lymphomas, and inflammation. Maresz K, Pryce G, Ponomarev E D, Marsicano G, Croxford J L, Shriver L P, Ledent C, Cheng X, Carrier E J, Mann M K, Giovannoni G, Pertwee R G, Yamamura T, Buckley N E, Hillard C J, Lutz B, Baker D, Dittel B N, *Direct Suppression of CNS Autoimmune Inflammation Via the Cannabinoid Receptor CB1 on Neurons and CB2 on Autoreactive T Cells*, Nat Med 2007, 13: 492-497.

Moreover, CB1 antagonists have been used for treatment obesity and addiction. Crowley V E F, Yeo G S H, O'Rahilly S, *Obesity Therapy: Altering the Energy Intake-and-Expenditure Balance Sheet*, Nature Reviews Drug Discovery 2002, 1:276-286; Trang T, Sutak M, Jhamandas K, *Involvement of Cannabinoid (CB1)-Receptors in the Development and Maintenance of Opioid Tolerance*, Neuroscience 2007, 146: 1275-1288; Teixeira-Clerc F, Julien B, Grenard P, Van Nhieu J T, Deveaux V, Li L, Serriere-Lanneau V, Ledent C, Mallat A, Lotersztajn S, *CB1 Cannabinoid Receptor Antagonism: A New Strategy For the Treatment of Liver Fibrosis*, Nat Med 2006, 12:671-676. For example, the CB1 antagonist SR141716A reduces food intake in mice. Di Marzo V, Goparaju S K, Wang L, Liu J, Batkai S, Jarai Z, Fezza F, Miura G I, Palmiter R D, Sugiura T, Kunos G, *Leptin-Regulated Endocannabinoids Are Involved In Maintaining Food*

*Intake*, Nature 2001, 410:822-5. Also, CB1 cannabinoid antagonists have been cited to treat drug addiction. Maldonado R, Valverde O, Berrendero F, *Involvement Of The Endocannabinoid System In Drug Addiction*, Trends Neurosci 2006, 29:225-32. Cannabinoids attenuate deep tissue hyperalgesia produced by both cancer and inflammatory conditions. Kehl L J, Hamamoto D T, Wacnik P W, Croft D L, Norsted B D, Wilcox G L, Simone D A, *A Cannabinoid Agonist Differentially Attenuates Deep Tissue Hyperalgesia In Animal Models Of Cancer And Inflammatory Muscle Pain*, Pain 2003, 103:175-86. Cannabinoids also have a good potential for the treatment osteoporosis and other bone diseases. Idris A I, van 't Hof R J, Greig I R, Ridge S A, Baker D, Ross R A, Ralston S H, *Regulation Of Bone Mass, Bone Loss And Osteoclast Activity By Cannabinoid Receptors*, Nat Med 2005, 11:774-9. Cannabinoids are able to reduce intraocular pressure. Szczesniak A M, Kelly M E, Whynot S, Shek P N, Hung O. *Ocular hypotensive effects of an intratracheally delivered liposomal delta9-tetrahydrocannabinol preparation in rats*, J Ocul Pharmacol Ther. 2006 June; 22(3):160-7. CB1 has also been shown to be involved in ectopic pregnancy in mice. Wang H, Guo Y, Wang D, Kingsley P J, Marnett L J, Das S K, DuBois R N, Dey S K, *Aberrant Cannabinoid Signaling Impairs Oviductal Transport of Embryos*, Nat Med 2004, 10:1074-1080.

Certain published data demonstrate that human keratinocytes partake in the peripheral endocannabinoid system. CB1 receptors have been implicated in epidermal differentiation and skin development. Maccarrone M, Di Rienzo M, Battista N, Gasperi V, Guerrieri P, Rossi A, Finazzi-Agro A, *The Endocannabinoid System In Human Keratinocytes. Evidence That Anandamide Inhibits Epidermal Differentiation Through CB1 Receptor-Dependent Inhibition Of Protein Kinase C, Activation Protein-1, And Transglutaminase*, J Biol Chem 2003, 278:33896-903. Hence, cannabinoid modulator can be useful in the treatment of skin diseases.

Recently it has been shown that show that cannabinoids inhibit keratinocyte proliferation, and therefore support a potential role for cannabinoids in the treatment of psoriasis. Wilkinson J D, Williamson E M, *Cannabinoids Inhibit Human Keratinocyte Proliferation Through A Non-CB1/CB2 Mechanism And Have A Potential Therapeutic Value In The Treatment Of Psoriasis*, J Dermatol Sci 2007, 45:87-92. Cannabinoid receptors have also been described as novel targets for the treatment of melanoma. Blazquez C, Carracedo A, Barrado L, Real P J, Fernandez-Luna J L, Velasco G, Malumbres M, Guzman M, *Cannabinoid Receptors As Novel Targets For The Treatment Of Melanoma*, Faseb J 2006, 20:2633-5.

General Synthetic Methods for Preparing Compounds

The following schemes can be used to practice the present invention.

General synthetic scheme for compounds of Formula I, Formula II, Formula III, Formula IV and Formula V:

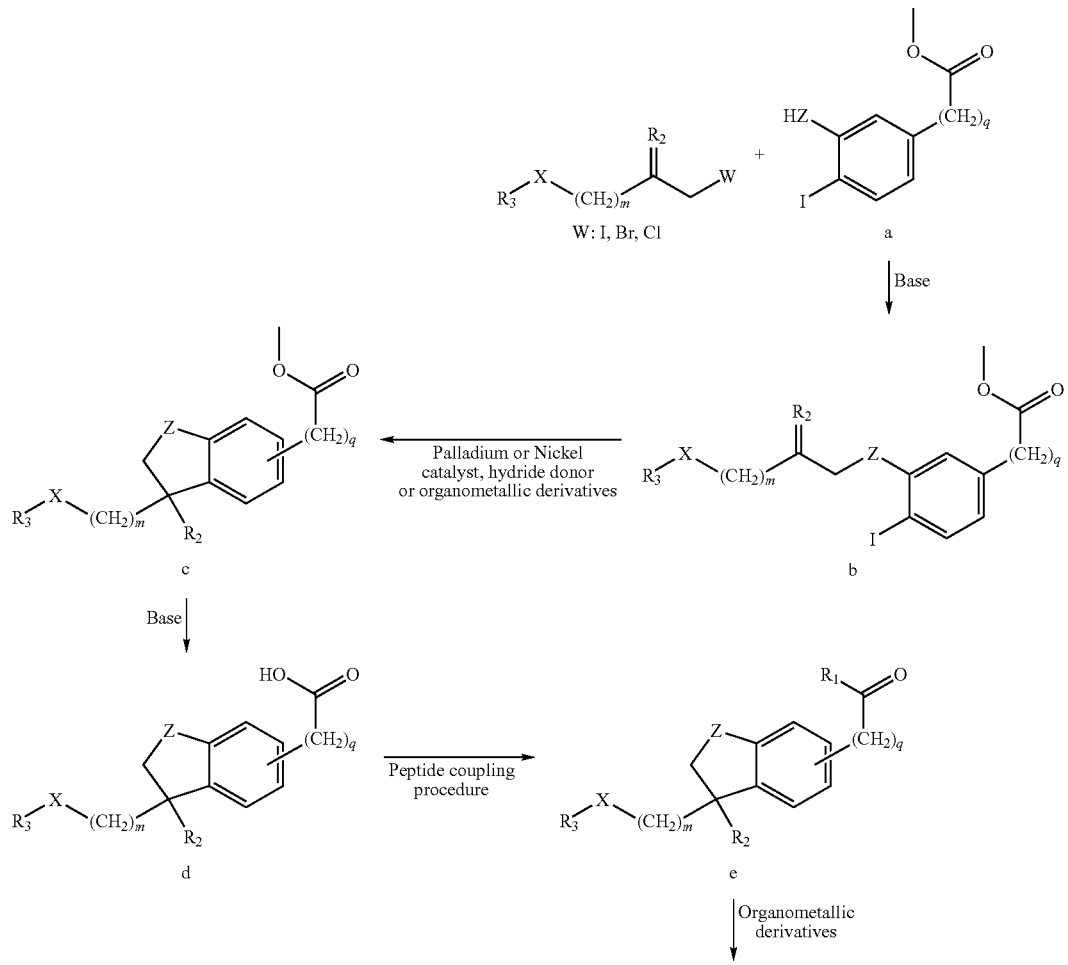

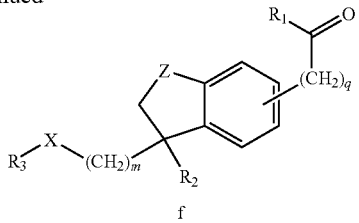

The compounds of Formula I, Formula II, Formula III, Formula IV and Formula V may be obtained by alkylation of the corresponding iodophenol a (Z=O, iodoaniline, Z=N, may be used for indole analogues) using a base such as cesium carbonate or sodium hydride, for example, to provide the phenolic ether b. The phenolic ether is subjected to a transition metal (such as nickel or palladium) catalyzed cyclization in the presence of a hydride donor such as ammonium formate or an organometallic derivatives in order to obtain the cyclized 2,3-dihydrobenzofuran (or indole) product c. After saponification of the ester to yield to the corresponding carboxylic acid d, a peptide coupling procedure using, for example, HATU, DIEA affords the corresponding amide derivatives e ($R_1$=NHR). Using the Weinreb amide ($R_1$=NHOMe) allows for organometallic additions, such as hexyl lithium for example, affording ketone products f in which $R_1$ is, for example, an alkyl or aryl group.

The invention is further illustrated by the following examples.

EXAMPLE 1

3-Benzyl-3-methyl-2,3-dihydro-benzofuran-6-carboxylic acid (2-iodo-phenyl)-amide

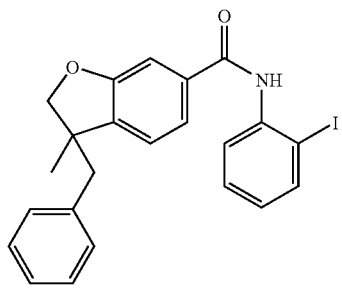 [SMILES: CC1(Cc2ccccc2)COc2cc(C(=O)Nc3ccccc3I)ccc21]

A) 4-Iodo-3-(2-methyl-allyloxy)-benzoic acid methyl ester

To a solution of methyl 3-hydroxy-4-iodobenzoate (1.5 g, 5.4 mmol) in anhydrous methyl ethyl ketone (60 mL) was added finely powdered Potassium carbonate (1.49 g, 10.78 mmol) followed by 3-bromo-2-methyl-propene (0.81 mL, 1.1 g, 8.15 mmol). The reaction mixture was heated at 70° C. for 4 h. The mixture was diluted filtrated, washed with water and dried over MgSO4. Evaporation of the solvent and of the remaining bromopropene in vacuo afforded the requisite alkylated ester as a yellow oil. M: 1.4 g, Yield: 78%

NMR (CDCl$_3$, 1H): 1.90 (3H, d, J=1.2 Hz), 194 (3H, s), 4.56 (2H, s), 5.06 (1H, d, J=1.2 Hz), 5.25 (1H, d, J=1.2 Hz), 7.38 (1H, dd, J=8.1 Hz, J=1.8 Hz), 7.44 (1H, d, J=1.8 Hz), 7.88 (1H, d, J=1.8 Hz)

B) 3-Benzyl-3-methyl-2,3-dihydro-benzofuran-6-carboxylic acid methyl ester

To a solution of 4-Iodo-3-(2-methyl-allyloxy)-benzoic acid methyl ester (455 mg, 1.37 mmol) obtained in Example 4(A), in DMF (15 mL) were added Potassium carbonate (379 mg, 2.74 mmol), Tetrabutylammonium chloride (380 mg, 1.37 mmol), Palladium acetate (25.6 mg, 0.136 mmol) in DMF (5 mL) and Phenylboronic acid (200 mg, 1.64 mmol). The resulting mixture was stirred for 3 h at 115° C., cooled to room temperature, filtered over silica, washed with water, dried over MgSO4 and concentrated. Column chromatography (silica gel, heptane/CH$_2$Cl$_2$: 4/6) afforded 368 mg (95%) of the title compound as a slightly brown oil which crystallize. Mp:52° C.

NMR (CDCl$_3$, 1H): 1.38 (3H, s), 2.86 (1H, d, J=14 Hz), 2.93 (1H, d, J=14 Hz), 3.89 (3H, s), 4.12 (1H, d, J=8.7 Hz), 4.55 (1H, d, J=8.7 Hz), 6.93-6.98 (3H, m), 7.22-7.24 (3H, m), 7.38 (1H, d, J=1.2 Hz), 7.59 (1H, dd, J1=7.5 Hz, J2=1.2 Hz).

C) 3-Benzyl-3-methyl-2,3-dihydro-benzofuran-6-carboxylic acid

A mixture of 3-Benzyl-3-methyl-2,3-dihydro-benzofuran-6-carboxylic acid methyl ester (300 mg, 1.06 mmol) obtained in Example 4(B), sodium hydroxide (260 mg, 6.5 mmol), ethanol (10 ml) and water (1 ml) in tetrahydrofuran (10 ml), is stirred for 12 h at room temperature. The reaction medium is acidified by adding a 1.2 M hydrochloric acid solution and extracted with ethyl acetate. The organic phase is washed with water, dried (Na2SO4), and concentrated in a rotary evaporator. The product is obtained as a white solid (300 mg, 100%). Mp: 165° C.

NMR (CDCl$_3$, $^1$H): 1.39 (3H, s), 2.87 (1H, d, J=14 Hz), 2.93 (1H, d, J=14 Hz), 4.14 (1H, d, J=8.7 Hz), 4.57 (1H, d, J=8.7 Hz), 6.96-7.00 (3H, m), 7.22-7.25 (3H, m), 7.45 (1H, d, J=1.2 Hz), 7.65 (1H, dd, J1=7.8 Hz, J2=1.2 Hz).

D) 3-Benzyl-3-methyl-2,3-dihydro-benzofuran-6-carboxylic acid (2-iodo-phenyl)-amide To a stirred suspension of 3-Benzyl-3-methyl-2,3-dihydro-benzofuran-6-carboxylic acid (80 mg, 0.3 mmol) and 2-Iodoaniline (72 mg, 0.33 mmol) in dichloromethane (3 mL) and DMF (2 mL) were added O-(7-Azabenzotriazol-1-yl)-N,N,N',N'-tetramethyluronium hexafluorophosphate (HATU) (125 mg, 0.33 mmol) and then a solution of N,N-diisopropylethylamine (58 mg, 78 µL, 0.45 mmol, mL) in DMF (1 mL). The reaction mixture was stirred at ambient temperature for 18 h. The reaction medium is acidified by adding a 1.2 M hydrochloric acid solution and extracted with ethyl acetate. The organic phase is washed with water, dried (MgSO$_4$), and concentrated to give the amide which is purified by flash chromatography (AcOEt/heptane: 4/6). The column was chosen too small and a bigger column was chosen (AcOEt/heptane: 4/6) to afford 22 mg of the desired amid as a pale yellow solid (16%).

NMR (CDCl₃, ¹H): 1.44 (3H, s), 2.92 (1H, d, J=13.2 Hz), 2.98 (1H, d, J=13.2 Hz), 4.21 (1H, d, J=8.7 Hz), 4.62 (1H, d, J=8.7 Hz), 6.98-7.00 (2I-1, m), 7.07 (1II, d, J=7.8 Hz), 7.26-728 (4H, m), 7.46 (1H, dd, J1=4.5 Hz, J2=8.4 Hz), 7.61 (1H, d, J=1.2 Hz), 7.85 (1H, dd, J1=1.2 Hz, J2=7.8 Hz), 8.46 (1H, dd, J1=1.5 Hz, J2=8.4 Hz), 8.74 (1H, dd, J1=1.5 Hz, J2=4.5 Hz).

EXAMPLE 2

3-Benzyl-3-methyl-2,3-dihydro-benzofuran-6-carboxylic acid cyclohexylamide

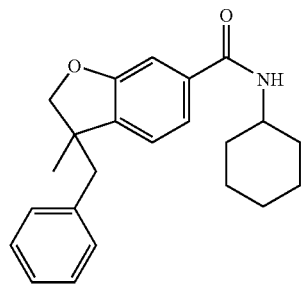 [SMILES: CC1(Cc2ccccc2)COc2cc(C(=O)NC3CCCCC3)ccc21]

A) 4-Iodo-3-(2-methyl-allyloxy)-benzoic acid methyl ester

To a solution of methyl 3-hydroxy-4-iodobenzoate (1.5 g, 5.4 mmol) in anhydrous methyl ethyl ketone (60 mL) was added finely powdered Potassium carbonate (1.49 g, 10.78 mmol) followed by 3-bromo-2-methyl-propene (0.81 mL, 1.1 g, 8.15 mmol). The reaction mixture was heated at 70° C. for 4 h. The mixture was diluted filtrated, washed with water and dried over MgSO4. Evaporation of the solvent and of the remaining bromopropene in vacuo afforded the requisite alkylated ester as a yellow oil. M: 1.4 g, Yield: 78%

NMR (CDCl₃, 1H): 1.90 (3H, d, J=1.2 Hz), 3.94 (3H, s), 4.56 (2H, s), 5.06 (1H, d, J=1.2 Hz), 5.25 (1H, d, J=1.2 Hz), 7.38 (1H, dd, J=8.1 Hz, J=1.8 Hz), 7.44 (1H, d, J=1.8 Hz), 7.88 (1H, d, J=1.8 Hz)

B) 3-Benzyl-3-methyl-2,3-dihydro-benzofuran-6-carboxylic acid methyl ester

To a solution of 4-Iodo-3-(2-methyl-allyloxy)-benzoic acid methyl ester (455 mg, 1.37 mmol) obtained in Example 4(A), in DMF (15 mL) were added Potassium carbonate (379 mg, 2.74 mmol), Tetrabutylammonium chloride (380 mg, 1.37 mmol), Palladium acetate (25.6 mg, 0.136 mmol) in DMF (5 mL) and Phenylboronic acid (200 mg, 1.64 mmol). The resulting mixture was stirred for 3 h at 115° C., cooled to room temperature, filtered over silica, washed with water, dried over MgSO4 and concentrated. Column chromatography (silica gel, heptane/CH₂Cl₂: 4/6) afforded 368 mg (95%) of the title compound as a slightly brown oil which crystallize. Mp:52° C.

NMR (CDCl₃, 1H): 1.38 (3H, s), 2.86 (1H, d, J=14 Hz), 2.93 (1H, d, J=14 Hz), 3.89 (3H, s), 4.12 (1H, d, J=8.7 Hz), 4.55 (1H, d, J=8.7 Hz), 6.93-6.98 (3H, m), 7.22-7.24 (3H, m), 7.38 (1H, d, J=1.2 Hz), 7.59 (1H, dd, J1=7.5 Hz, J2=1.2 Hz).

C) 3-Benzyl-3-methyl-2,3-dihydro-benzofuran-6-carboxylic acid

A mixture of 3-Benzyl-3-methyl-2,3-dihydro-benzofuran-6-carboxylic acid methyl ester (300 mg, 1.06 mmol) obtained in Example 4(B), sodium hydroxide (260 mg, 6.5 mmol), ethanol (10 ml) and water (1 ml) in tetrahydrofuran (10 ml), is stirred for 12 h at room temperature. The reaction medium is acidified by adding a 1.2 M hydrochloric acid solution and extracted with ethyl acetate. The organic phase is washed with water, dried (Na2SO4), and concentrated in a rotary evaporator. The product is obtained as a white solid (300 mg, 100%). Mp: 165° C.

NMR (CDCl₃, ¹H): 1.39 (3H, s), 2.87 (1H, d, J=14 Hz), 2.93 (1H, d, J=14 Hz), 4.14 (1H, d, J=8.7 Hz), 4.57 (1H, d, J=8.7 Hz), 6.96-7.00 (3H, m), 7.22-7.25 (3H, m), 7.45 (1H, d, J=1.2 Hz), 7.65 (1H, dd, J1=7.8 Hz, J2=1.2 Hz).

D) 3-Benzyl-3-methyl-2,3-dihydro-benzofuran-6-carboxylic acid cyclohexylamide To a stirred suspension of 3-Benzyl-3-methyl-2,3-dihydro-benzofuran-6-carboxylic acid (80 mg, 0.3 mmol) previously obtained in Example 4(C) and Cyclohexylamine (33 mg, 38 µL, 0.33 mmol) in dichloromethane (3 mL) and DMF (2 mL) were added 0-(7-Azabenzotriazol-1-yl)-N,N,N',N'-tetramethyluronium hexafluorophosphate (HATU) (125 mg, 0.33 mmol) and then a solution of N,N-diisopropylethylamine (58 mg, 78 pt, 0.45 mmol, mL) in DMF (1 mL). The reaction mixture was stirred at ambient temperature for 18 h. The reaction medium is acidified by adding a 1.2 M hydrochloric acid solution and extracted with ethyl acetate. The organic phase is washed with water, dried (MgSO₄), and concentrated to give the amide which is purified by flash chromatography (AcOEt/heptane: 4/6) to afford 70 mg of a white solid (yield: 67%).

NMR (CDCl₃, ¹H): 1.15-1.28 (3H, m), 1.34-1.46 (5H, m), 1.6-1.78 (3H, m), 1.99-2.04 (2H, m), 2.00-2.04 (2H, m), 2.86 (1H, d, J=13.2 Hz), 2.92 (1H, d, J=13.2 Hz), 3.96 (1H, m), 4.11 (1H, d, J=8.7 Hz), 4.54 (1H, d, J=8.7 Hz), 5.85 (1H, m), 6.92 (1H, d, J=7.5 Hz), 6.96-6.99 (2H, m), 7.10 (1H, d, J=1.5 Hz), 7.22-728 (4H, m).

EXAMPLE 3

3-benzyl-3-methyl-2,3-dihydrobenzofuran-6-carboxylic acid-piperidine amide

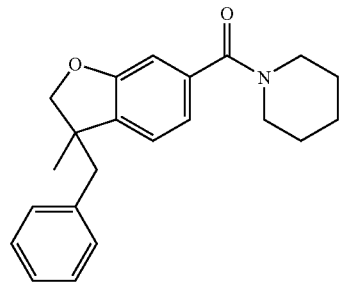 [SMILES: CC1(Cc2ccccc2)COc2cc(C(=O)N3CCCCC3)ccc21]

To a stirred suspension of the 3-Benzyl-3-methyl-2,3-dihydro-benzofuran-6-carboxylic acid (80 mg, 0.3 mmol) previously obtained in Example 1(C) and Piperidine (28 mg, 33 µL, 0.33 mmol) in dichloromethane (3 mL) and DMF (2 mL) were added O-(7-Azabenzotriazol-1-yl)-N,N,N',N'-tetramethyluronium hexafluorophosphate (HATU) (125 mg, 0.33 mmol) and then a solution of N,N-diisopropylethylamine (58 mg, 78 µL, 0.45 mmol, mL) in DMF (1 mL). The reaction mixture was stirred at ambient temperature for 18 h. The reaction medium is acidified by adding a 1.2 M hydrochloric acid solution and extracted with ethyl acetate. The organic phase is washed with water, dried ($MgSO_4$), and concentrated to give the amide which is purified by flash chromatography (AcOEt/heptane: 4/6) to afford 50 mg of a white solid (yield: 50%).

NMR ($CDCl_3$, $^1H$): 1.36 (3H, s), 1.54-1.67 (6H, m), 2.85 (1H, d, J=13.2 Hz), 2.90 (1H, d, J=13.2 Hz), 3.35 (2H, m), 3.68 (2H, m), 4.09 (1H, d, J=8.7 Hz), 4.53 (1H, d, J=8.7 Hz), 6.75 (1H, m), 6.88 (1H, dd, 31=7.5 Hz, J2=1.2 Hz), 6.94 (1H, d, J=7.5 Hz), 7.00 (2H, m), 7.21-7.24 (3H, m).

EXAMPLE 4

3-Benzyl-3-methyl-2,3-dihydro-benzofuran-5-carboxylic acid-o-iodoanilide

A) 4-Hydroxy-3-iodo-benzoic acid

4-Hydroxybenzoic acid (0.037 mol, 5.1 g) was dissolved in 100 mL of methanol. One equivalent each of sodium iodide (0.037 mol, 5.54 g) and sodium hydroxide (0.037 mol, 1.48 g) was added, and the solution was cooled to 0° C. Aqueous sodium hypochlorite (64 ml, 4.0% NaOCl) was added dropwise over 75 min at 0-3° C. As each drop hit the solution, a red color appeared and faded almost instantly. The resulting colorless slurry was stirred for 1 h at 0-2° C. and then was treated with 40 mL of 10% aqueous sodium thiosulfate. The mixture was acidified by 4M aqueous HCl. A product crystallized and was filtered off to afford 1.1 g. Ethyl acetate (250 mL) was added, and the layers were separated. The organic layer was washed with brine (240 mL), water and then dried over $MgSO_4$. After evaporation of the solvent, 4.3 g of a white powder was obtained. The aqueous phase was acidified to pH 1. Ethyl acetate (250 mL) was added, and the layers were separated. The organic layer was washed with brine (240 mL), water and then dried over $MgSO_4$. After evaporation of the solvent, 8.22 g of a white powder was obtained.

B) Methyl 4-hydroxy-3-iodobenzoate

A solution of 3-iodo-4-Hydroxybenzoic acid (7.25 g, 27.4 mmol) and sulfuric acid (1.9 ml, 36 mmol) in methanol is stirred at 55° C. for 6 hours. TLC (dichloromethane): 30% of starting material. The solution is stirred 12 h at room temperature. TLC (dichloromethane): 10% of starting material and stirred at 55° C. for 2 h. After cooling, ethyl acetate (200 mL) was added and the mixture was adjusted to pH 3 using sodium bicarbonate. The organic layer was washed two times with water and then dried over $MgSO_4$. Filtration and rotary evaporation at 40° C. afforded a white solid. The solid was triturated with hexane, filtered off and dried under reduced pressure. M=4.47 g. Yield: 59%.

C) 3-Iodo-4-(2-methyl-allyloxy)-benzoic acid methyl ester

To a solution of methyl 4-hydroxy-3-iodobenzoate (1.5 g, 5.4 mmol) in anhydrous methyl ethyl ketone (60 mL) was added finely powdered Potassium carbonate (1.49 g, 10.78 mmol) followed by 3-bromo-2-methyl-propene (0.81 mL, 1.1 g, 8.15 mmol). The reaction mixture was heated at 70° C. for 4 h. The mixture was diluted filtrated, washed with water and dried over $MgSO_4$. Evaporation of the solvent and of the remaining bromopropene in vacuo afforded the requisite alkylated ester as a yellow oil. M: 1.77, Yield: 98%.

1H(CDCl3): 1.88 (3H, d, J=1.2 Hz), 3.09 (3H, s), 4.54 (2H, s), 5.04 (1H, d, J=1.2 Hz), 5.19 (1H, d, J=1.2 Hz), 6.80 (1H, d, J=8.7 Hz), 7.98 (1H, dd, J=8.7 Hz, J=1.8 Hz), 8.46 (1H, d, J=1.8 Hz)

D) 3-Benzyl-3-methyl-2,3-dihydro-benzofuran-5-carboxylic acid methyl ester

To a solution of 3-Iodo-4-(2-methyl-allyloxy)-benzoic acid methyl ester (455 mg, 1.37 mmol) in DMF (15 mL) were added Potassium carbonate (379 mg, 2.74 mmol), Tetrabutylammonium chloride (380 mg, 1.37 mmol), a solution of Palladium acetate (25.6 mg, 0.136 mmol) in DMF (5 mL) and Phenylboronic acid (200 mg, 1.64 mmol). The resulting mixture was stirred for 3 h at 115° C., cooled to room temperature, filtered over silica, washed with water, dryed over MgSO4 and concentrated. Column chromatography (silica gel, heptane/$CH_2Cl_2$: 4/6) afforded 202 mg (52%) of the title compound as a slight brown oil.

NMR ($CDCl_3$, $^1H$): 1.39 (3H, s), 2.87 (1H, d, J=15 Hz), 2.93 (1H, d, J=15 Hz), 3.89 (3H, s), 4.13 (1H, d, J=9 Hz), 4.59 (1H, d, J=9 Hz), 6.74 (1H, d, J=8.4 Hz), 6.99 92H, m), 7.22-7.24 (3H, m), 7.72 (1H, d, J=1.8 Hz), 7.89 (1H, dd, J1=8.4 Hz, J2=1.8 Hz).

E) 3-Benzyl-3-methyl-2,3-dihydro-benzofuran-5-carboxylic acid

A mixture of 3-Benzyl-3-methyl-2,3-dihydro-benzofuran-5-carboxylic acid methyl ester (125 mg, 0.44 mmol), sodium hydroxide (120 mg, 3 mmol), ethanol (6 mL) and water (1 mL) in tetrahydrofuran (6 mL), is stirred for 12 h at room temperature. The reaction medium is acidified by adding a 1.2 M hydrochloric acid solution and extracted with ethyl acetate. The organic phase is washed with water, dried ($Na_2SO_4$), and concentrated in a rotary evaporator. The product is obtained as slightly brown oil (116 mg, 97%).

NMR ($CDCl_3$, $^1H$): 1.30 (3H, s), 2.77 (1H, d, J=13 Hz), 2.83 (1H, d, J=13 Hz), 4.05 (1H, d, J=9 Hz), 4.52 (1H, d, J=9 Hz), 6.67 (1H, d, J=8.4 Hz), 6.86-6.89 (2H, m), 7.11-7.14 (3H, m), 7.69 (1H, d, J=1.8 Hz), 7.89 (1H, dd, J1=8.4 Hz, J2=1.8 Hz), 11.41 (1H).

F) -Benzyl-3-methyl-2,3-dihydro-benzofuran-5-carboxylic acid-o-iodoanilide

To a stirred suspension of 3-Benzyl-3-methyl-2,3-dihydro-benzofuran-5-carboxylic acid (60 mg, 0.225 mmol) and 2-Iodoaniline (54 mg, 0.25 mmol) in dichloromethane (2 mL) and DMF (1 mL) were added O-(7-Azabenzotriazol-1-yl)-N,N, N', N'-tetramethyluronium hexafluorophosphate (HATU) (94 mg, 0.25 mmol) and a solution of N,N-diisopropylethylamine (44 mg, 59 µL, 0.34 mmol) in DMF (1 mL). The reaction mixture was stirred at ambient temperature for 18 h. The reaction medium is acidified by adding a 1.2 M hydrochloric acid solution and extracted with ethyl acetate. The organic phase is washed with water, dried (MgSO$_4$), and concentrated to give the amide which is purified by flash chromatography (AcOEt/heptane: 3/7) to afford 10 mg (10%) of a slightly brown solid.

NMR (CDCl3, 1H): 1.45 (3H, s), 2.88 (1H, d, J=13.5 Hz), 2.98 (1H, d, J=13.5 Hz), 4.24 (1H, d, J=9 Hz), 4.70 (1H, d, J=9 Hz), 6.89 (1H, d, J=8.4 Hz), 6.96-7.02 (3H, m), 7.22-7.28 (3H, m), 7.46 (2H, dd, J1=4.5 Hz, J2=8.4 Hz), 7.89 (1H, d, 2.1 Hz), 8.16 (1H, dd, J=1.8 Hz, j=8.4 Hz), 8.47 (1H, dd, J1=1.2 Hz, J2=8.4 Hz).

EXAMPLE 5

3-benzyl-3-methyl-2,3-dihydrobenzofuran-5-carboxylic acid-cyclohexylamide

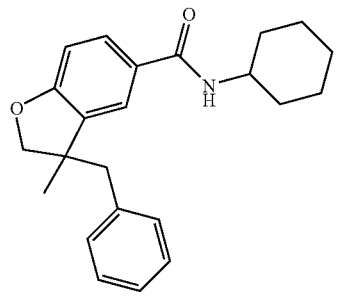 [SMILES: CC1(Cc2ccccc2)COc2ccc(C(=O)NC3CCCCC3)cc21]

A) 4-Hydroxy-3-iodo-benzoic acid

4-Hydroxybenzoic acid (0.037 mol, 5.1 g) was dissolved in 100 mL of methanol. One equivalent each of sodium iodide (0.037 mol, 5.54 g) and sodium hydroxide (0.037 mol, 1.48 g) was added, and the solution was cooled to 0° C. Aqueous sodium hypochlorite (64 ml, 4.0% NaOCl) was added dropwise over 75 min at 0-3° C. As each drop hit the solution, a red color appeared and faded almost instantly. The resulting colorless slurry was stirred for 1 h at 0-2° C. and then was treated with 40 mL of 10% aqueous sodium thiosulfate. The mixture was acidified by 4M aqueous HCl. A product crystallized and was filtered off to afford 1.1 g. Ethyl acetate (250 mL) was added, and the layers were separated. The organic layer was washed with brine (240 mL), water and then dried over MgSO$_4$. After evaporation of the solvent, 4.3 g of a white powder was obtained. The aqueous phase was acidified to pH 1. Ethyl acetate (250 mL) was added, and the layers were separated. The organic layer was washed with brine (240 mL), water and then dried over MgSO$_4$. After evaporation of the solvent, 8.22 g of a white powder was obtained.

B) Methyl 4-hydroxy-3-iodobenzoate

A solution of 3-iodo-4-Hydroxybenzoic acid (7.25 g, 27.4 mmol) and sulfuric acid (1.9 ml, 36 mmol) in methanol is stirred at 55° C. for 6 hours. TLC (dichloromethane): 30% of starting material. The solution is stirred 12 h at room temperature. TLC (dichloromethane): 10% of starting material and stirred at 55° C. for 2 h. After cooling, ethyl acetate (200 mL) was added and the mixture was adjusted to pH 3 using sodium bicarbonate. The organic layer was washed two times with water and then dried over MgSO$_4$. Filtration and rotary evaporation at 40° C. afforded a white solid. The solid was triturated with hexane, filtered off and dried under reduced pressure. M=4.47 g. Yield: 59%.

C) 3-Iodo-4-(2-methyl-allyloxy)-benzoic acid methyl ester

To a solution of methyl 4-hydroxy-3-iodobenzoate (1.5 g, 5.4 mmol) in anhydrous methyl ethyl ketone (60 mL) was added finely powdered Potassium carbonate (1.49 g, 10.78 mmol) followed by 3-bromo-2-methyl-propene (0.81 mL, 1.1 g, 8.15 mmol). The reaction mixture was heated at 70° C. for 4 h. The mixture was diluted filtrated, washed with water and dried over MgSO$_4$. Evaporation of the solvent and of the remaining bromopropene in vacuo afforded the requisite alkylated ester as a yellow oil. M: 1.77, Yield: 98%.

1H(CDCl$_3$): 1.88 (3H, d, J=1.2 Hz), 3.09 (3H, s), 4.54 (2H, s), 5.04 (1H, d, J=1.2 Hz), 5.19 (1H, d, J=1.2 Hz), 6.80 (1H, d, J=8.7 Hz), 7.98 (1H, dd, J=8.7 Hz, J=1.8 Hz), 8.46 (1H, d, J=1.8 Hz)

D) 3-Benzyl-3-methyl-2,3-dihydro-benzofuran-5-carboxylic acid methyl ester

To a solution of 3-Iodo-4-(2-methyl-allyloxy)-benzoic acid methyl ester (455 mg, 1.37 mmol) in DMF (15 mL) were added Potassium carbonate (379 mg, 2.74 mmol), Tetrabutylammonium chloride (380 mg, 1.37 mmol), a solution of Palladium acetate (25.6 mg, 0.136 mmol) in DMF (5 mL) and Phenylboronic acid (200 mg, 1.64 mmol). The resulting mixture was stirred for 3 h at 115° C., cooled to room temperature, filtered over silica, washed with water, dryed over MgSO4 and concentrated. Column chromatography (silica gel, heptane/CH$_2$Cl$_2$: 4/6) afforded 202 mg (52%) of the title compound as a slight brown oil.

NMR (CDCl$_3$, $^1$H): 1.39 (3H, s), 2.87 (1H, d, J=15 Hz), 2.93 (1H, d, J=15 Hz), 3.89 (3H, s), 4.13 (1H, d, J=9 Hz), 4.59 (1H, d, J=9 Hz), 6.74 (1H, d, J=8.4 Hz), 6.99 92H, m), 7.22-7.24 (3H, m), 7.72 (1H, d, J=1.8 Hz), 7.89 (1H, dd, J1=8.4 Hz, J2=1.8 Hz).

E) 3-Benzyl-3-methyl-2,3-dihydro-benzofuran-5-carboxylic acid

A mixture of 3-Benzyl-3-methyl-2,3-dihydro-benzofuran-5-carboxylic acid methyl ester (125 mg, 0.44 mmol), sodium hydroxide (120 mg, 3 mmol), ethanol (6 mL) and water (1 mL) in tetrahydrofuran (6 mL), is stirred for 12 h at room temperature. The reaction medium is acidified by adding a 1.2 M hydrochloric acid solution and extracted with ethyl acetate. The organic phase is washed with water, dried (Na$_2$SO$_4$), and concentrated in a rotary evaporator. The product is obtained as slightly brown oil (116 mg, 97%).

NMR (CDCl$_3$, 1H): 1.30 (3H, s), 2.77 (1H, d, J=13 Hz), 2.83 (1H, d, J=13 Hz), 4.05 (1H, d, J=9 Hz), 4.52 (1H, d, J=9 Hz), 6.67 (1H, d, J=8.4 Hz), 6.86-6.89 (2H, m), 7.11-7.14 (3H, m), 7.69 (1H, d, J=1.8 Hz), 7.89 (1H, dd, J1=8.4 Hz, J2=1.8 Hz), 11.41 (1H).

F) 3-Benzyl-3-methyl-2,3-dihydro-benzofuran-5-carboxylic acid cyclohexylamide

To a stirred suspension of the 3-Benzyl-3-methyl-2,3-dihydro-benzofuran-5-carboxylic acid (60 mg, 0.225 mmol)

previously obtained in Example 4(E) and Cyclohexylamine (25 mg, 29 µL, 0.25 mmol in dichloromethane (2 mL) and DMF (1 mL) were added O-(7-Azabenzotriazol-1-yl)-N,N,N',N'-tetramethyluronium hexafluorophosphate (HATU) (94 mg, 0.25 mmol) and then N,N-diisopropylethylamine (44 mg, 59 µL, 0.34 mmol). The reaction mixture was stirred at ambient temperature for 18 h. The reaction medium is acidified by adding a 1.2 M hydrochloric acid solution and extracted with ethyl acetate. The organic phase is washed with water, dried (MgSO$_4$), and concentrated to give the amide as a white solid. The solid was washed with a mixture of heptane and dichloromethane 9/1 to afford 38 mg of a white solid (Yield: 48%). The filtrate was concentrated and the white solid obtained was washed with a mixture of heptane and dichloromethane (9/1) to afford 13 mg of a white solid.

NMR (CDCl$_3$, 1H): 1.19-1.28 (3H, m), 1.3-1.45 (9H, m), 2.02 (2H, m), 2.86 (1H, d, J=13.5 Hz), 2.92 (1H, d, J=13.5 Hz), 3.91-3.97 (2H, m), 4.14 (1H, d, J=8.7 Hz), 4.57 (1H, d, J=8.7 Hz), 5.73 (1H, m), 6.75 (1H, d, J=8.4 Hz), 6.96-6.99 (2H, m), 7.23-7.26 (4H, m), 7.56 (1H, dd, J=1.8 Hz, j=8.4 Hz).

EXAMPLE 6

3-benzyl-3-methyl-2,3-dihydrobenzofuran-5-carboxylic acid-piperidine amide

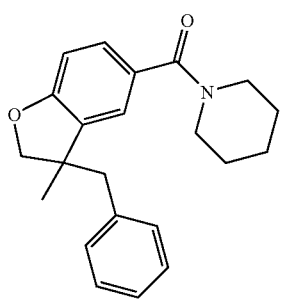 [SMILES: CC1(Cc2ccccc2)COc2ccc(C(=O)N3CCCCC3)cc21]

To a stirred suspension of the 3-Benzyl-3-methyl-2,3-dihydro-benzofuran-5-carboxylic acid (60 mg, 0.225 mmol) previously obtained in Example 4(E) and Piperidine (21 mg, 25 µL 0.25 mmol) in dichloromethane (2 mL) and DMF (1 mL) were added O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL). The reaction mixture was stirred at ambient temperature for 18 h. The reaction medium is acidified by adding a 1.2 M hydrochloric acid solution and extracted with ethyl acetate. The organic phase is washed with water, dried (MgSO$_4$), and concentrated to give the amide which is purified by flash chromatography (AcOEt/heptane: 4/6) to afford 54 mg (71.5%) of the desired amide as a colorless oil.

NMR (CDCl$_3$, 1H): 1.37 (3H, s), 1.58-1.69 (6H, m), 2.86 (1H, d, J=13.5 Hz), 2.92 (1H, d, J=13.5 Hz), 3.51 (4H, broad), 4.10 (1H, d, J=8.7 Hz), 4.54 (1H, d, J=8.7 Hz), 6.73 (1H, d, J=8.1 Hz), 6.98-7.03 (3H, m), 7.18-7.23 (4H, m).

EXAMPLE 7

3-benzyl-3-methyl-2,3-dihydrobenzofuran-5-carboxylic acid (2,2-dimethyl-propyl)-amide

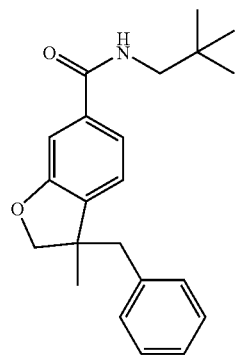 [SMILES: CC(C)(C)CNC(=O)c1ccc2c(c1)OCC2(C)Cc1ccccc1]

In a manner similar to that of Example 6, by reacting 3-Benzyl-3-methyl-2,3-dihydro-benzofuran-6-carboxylic acid (60 mg, 0.225 mmol) previously obtained in Example 1(C), neopentylamine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL) expected derivative was obtained as an colorless oil. NMR (CDCl$_3$): δ 0.98 (s, 9H), 1.37 (s, 6H), 2.86 (d, 1H), 2.91 (d, 1H), 3.26 (d, 2H), 4.12 (d, 1H), 4.54 (d, 1H), 6.08 (br s, 1H), 6.95 (d, 1H), 6.98-7.00 (m, 2H), 7.12 (d, 1H), 7.23-7.25 (m, 3H), 7.29 (dd, 1H).

EXAMPLE 8

3-Benzyl-3-methyl-2,3-dihydro-benzofuran-6-carboxylic acid (tetrahydro-pyran-4-ylmethyl)-amide

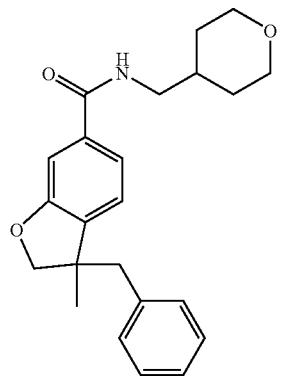 [SMILES: CC1(Cc2ccccc2)COc2cc(C(=O)NCC3CCOCC3)ccc21]

In a manner similar to that of Example 6, by reacting 3-Benzyl-3-methyl-2,3-dihydro-benzofuran-6-carboxylic acid (60 mg, 0.225 mmol) previously obtained in Example 1(C), 4-(Aminomethyl)tetrahydropyran (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL) expected derivative was obtained as an colorless oil. NMR (CDCl$_3$): δ 1.30-1.45 (m, 9H), 1.65 (d, 2H), 2.86 (d, 1H), 2.91 (d, 1H), 3.23-3.40 (m, 4H), 3.98 (dd, 2H), 4.12 (d, 1H), 4.54 (d, 1H), 6.23 (br s, 1H), 6.94 (d, 1H), 6.98-7.00 (m, 2H), 7.12 (d, 1H), 7.23-7.25 (m, 3H), 7.28 (dd, 1H).

EXAMPLE 9

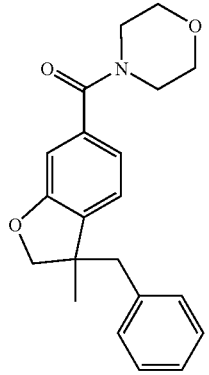 [SMILES: CC1(Cc2ccccc2)COc2cc(C(=O)N3CCOCC3)ccc21]

In a manner similar to that of Example 6, by reacting 3-Benzyl-3-methyl-2,3-dihydro-benzofuran-6-carboxylic acid (60 mg, 0.225 mmol) previously obtained in Example 1(C), Morpholine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL) expected derivative was obtained as an colorless oil. NMR (CDCl$_3$): δ 1.36 (s, 6H), 2.86 (d, 1H), 2.90 (d, 1H), 3.46-3.72 (br m, 8H), 4.10 (d, 1H), 4.54 (d, 1H), 6.77 (d, 1H), 6.90 (dd, 1H), 6.95 (d, 1H), 7.00 (dd, 1H), 7.22-7.26 (m, 3H).

EXAMPLE 10

3-Benzyl-3-methyl-2,3-dihydro-benzofuran-6-carboxylic acid (2,2-dimethyl-propyl)-methyl-amide

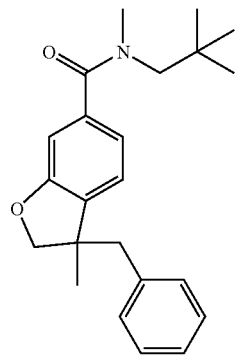 [SMILES: CN(CC(C)(C)C)C(=O)c1ccc2c(c1)OCC2(C)Cc1ccccc1]

In a manner similar to that of Example 6, by reacting 3-Benzyl-3-methyl-2,3-dihydro-benzofuran-6-carboxylic acid (60 mg, 0.225 mmol) previously obtained in Example 1(C), N-tert-Butylmethylamine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL) expected derivative was obtained as an colorless oil. NMR (CDCl$_3$): δ 1.35 (s, 6H), 1.49 (s, 9H), 2.85-2.88 (m, 5H), 4.08 (d, 1H), 4.51 (d, 1H), 6.78 (d, 1H), 6.89 (d, 1H), 6.93 (dd, 1H), 6.97-7.00 (m, 2H), 7.20-7.24 (m, 3H).

EXAMPLE 11

3-Benzyl-3-methyl-2,3-dihydro-benzofuran-6-carboxylic acid ((S)-1,2,2-trimethyl-propyl)-amide

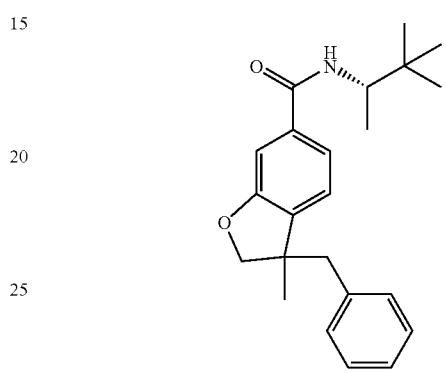

In a manner similar to that of Example 6, by reacting 3-Benzyl-3-methyl-2,3-dihydro-benzofuran-6-carboxylic acid (60 mg, 0.225 mmol) previously obtained in Example 1(C), (S)-(+)-3,3-Dimethyl-2-butylamine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL) expected derivative was obtained as an colorless oil. NMR (CDCl$_3$): δ 0.97 (s, 9H), 1.15 (d, 3H), 1.36 (s, 3H), 2.86 (d, 1H), 2.93 (d, 1H), 4.06-4.13 (m, 2H), 4.54 (d, 1H), 6.93 (d, 1H), 6.99 (dd, 1H), 7.10 (dd, 1H), 7.23-7.29 (m, 5H).

EXAMPLE 12

3-Benzyl-3-methyl-2,3-dihydro-benzofuran-6-carboxylic acid ((R)-1,2,2-trimethyl-propyl)-amide

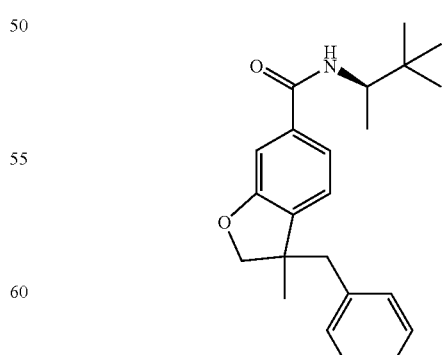

In a manner similar to that of Example 6, by reacting 3-Benzyl-3-methyl-2,3-dihydro-benzofuran-6-carboxylic acid (60 mg, 0.225 mmol) previously obtained in Example 1(C), (R)-(+3,3-Dimethyl-2-butylamine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL) expected derivative was obtained as an colorless oil.

EXAMPLE 13

[3-(4-Chloro-benzyl)-3-methyl-2,3-dihydro-benzofuran-6-yl]-piperidin-1-yl-methanone

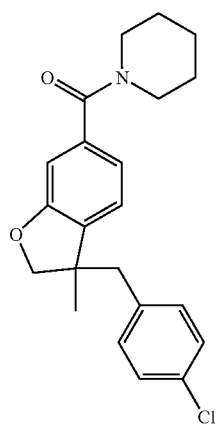 [SMILES: CC1(Cc2ccc(Cl)cc2)COc2cc(C(=O)N3CCCCC3)ccc21]

A) 3-(4-Chloro-benzyl)-3-methyl-2,3-dihydro-benzofuran-6-carboxylic acid methyl ester A solution of 4-Iodo-3-(2-methyl-allyloxy)-benzoic acid methyl ester (455 mg, 1.37 mmol) in DMF (15 mL) were added Potassium carbonate (379 mg, 2.74 mmol), Tetrabutylammonium chloride (380 mg, 1.37 mmol), Palladium acetate (25.6 mg, 0.136 mmol) in DMF (5 mL) and 4-Chlorophenylboronic acid, (256 mg, 1.64 mmol) was submitted to microwave irradiation at 140° C. for 21 minutes. The resulting mixture was filtered over silica, washed with water, dried over MgSO4 and concentrated. Column chromatography (silica gel, heptane/CH$_2$Cl$_2$: 5/5) afforded 160 mg (37%) of the title compound as a slightly brown oil.

B) 3-(4-Chloro-benzyl)-3-methyl-2,3-dihydro-benzofuran-6-carboxylic acid

A mixture of 3-(4-Chloro-benzyl)-3-methyl-2,3-dihydrobenzofuran-6-carboxylic acid methyl ester (100 mg, 0.32 mmol), sodium hydroxide (100 mg, 2.5 mmol), ethanol (3 ml) and water (0.5 ml) in tetrahydrofuran (4 ml), was stirred for 12 h at room temperature. The reaction medium was acidified by adding a 1.2 M hydrochloric acid solution and extracted with ethyl acetate. The organic phase was washed with water, dried (Na$_2$SO$_4$), and concentrated in a rotary evaporator. The product was obtained as a white solid. (M: 89 mg, 92%).

C) [3-(4-Chloro-benzyl)-3-methyl-2,3-dihydro-benzofuran-6-yl]-piperidin-1-yl-methanone In a manner similar to that of Example 6, by reacting 3-(4-Chloro-benzyl)-3-methyl-2,3-dihydro-benzofuran-6-carboxylic acid (0.225 mmol) previously obtained in Example 13(B), Piperidine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL) expected derivative was obtained as an colorless oil. NMR (CDCl$_3$): δ 1.36 (s, 3H), 2.84 (t, 1H), 3.33 (br s, 2H), 3.67 (br s, 2H), 4.10 (d, 1H), 4.48 (d, 1H), 6.74 (s, 1H), 6.88-6.91 (m, 4H), 7.2 (d, 2H).

EXAMPLE 14

(3-Methyl-3-naphthalen-1-ylmethyl-2,3-dihydro-benzofuran-6-yl)-piperidin-1-yl-methanone

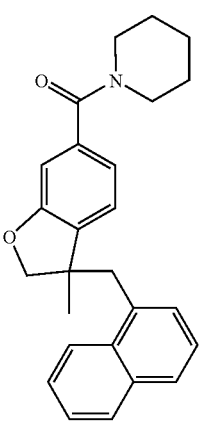 [SMILES: CC1(Cc2cccc3ccccc23)COc2cc(C(=O)N3CCCCC3)ccc21]

A) 3-Methyl-3-naphthalen-1-ylmethyl-2,3-dihydro-benzofuran-6-carboxylic acid methyl ester A solution of 4-Iodo-3-(2-methyl-allyloxy)-benzoic acid methyl ester (455 mg, 1.37 mmol) in DMF (15 mL) were added Potassium carbonate (379 mg, 2.74 mmol), Tetrabutylammonium chloride (380 mg, 1.37 mmol), Palladium acetate (25.6 mg, 0.136 mmol) in DMF (5 mL) and 1-Naphthylboronic acid, (282 mg, 1.64 mmol) was submitted to microwave irradiation at 100° C. for 10 minutes and as the reaction was not completed at 150° C. for 15 minutes. The resulting mixture was filtered over silica, washed with water, dried over MgSO4 and concentrated. Column chromatography (silica gel, heptane/CH$_2$Cl$_2$: 4/6) afforded 196 mg (43%) of the title compound as a slightly brown oil.

B) 3-Methyl-3-naphthalen-1-ylmethyl-2,3-dihydro-benzofuran-6-carboxylic acid A mixture of 3-Methyl-3-naphthalen-1-ylmethyl-2,3-dihydro-benzofuran-6-carboxylic acid methyl ester (150 mg, 0.45 mmol), sodium hydroxide (150 mg, 3.75 mmol), ethanol (5 ml) and water (1 ml) in tetrahydrofuran (5 ml), was stirred for 12 h at room temperature. The reaction medium was acidified by adding a 1.2 M hydrochloric acid solution and extracted with ethyl acetate. The organic phase was washed with water, dried (Na$_2$SO$_4$), and concentrated in a rotary evaporator. The product was obtained as a brown oil (M: 128 mg, 89%).

C) (3-Methyl-3-naphthalen-1-ylmethyl-2,3-dihydro-benzofuran-6-yl)-piperidin-1-yl-methanone In a manner similar to that of Example 6, by 3-Methyl-3-naphthalen-1-ylmethyl-2,3-dihydro-benzofuran-6-carboxylic acid (0.225 mmol) previously obtained in Example 14(B), Piperidine (0.25 mmol) in dichloromethane (2 mL) and DMF (1 mL), O-(7-Azabenzothazol-1-yl)-N,N,N',N'-tetramethyluronium hexafluorophosphate (HATU) (94 mg, 0.25 mmol) and a solution of N,N-diisopropylethylamine (44 mg, 59 μL, 0.34 mmol) in DMF (1 mL) expected derivative was obtained as an colorless oil. NMR (CDCl$_3$): δ 1.43 (s, H), 3.30 (br d, 3H), 3.50 (d, 1H), 3.67 (br s, 2H), 4.09 (d, 1H), 4.58 (d, 1H), 6.74 (m, 2H), 7.19 (dd, 1H), 7.32-7.43 (m, 3H), 7.75 (d, 1H), 7.81 (d, 1H).

EXAMPLE 15

(3-Methyl-3-naphthalen-2-ylmethyl-2,3-dihydro-benzofuran-6-yl)-piperidin-1-yl-methanone

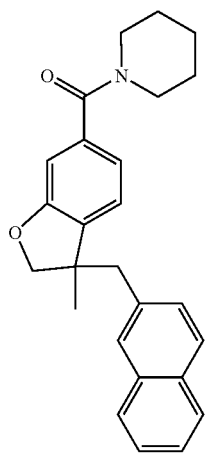 [SMILES: CC1(Cc2ccc3ccccc3c2)COc2cc(C(=O)N3CCCCC3)ccc21]

A) 3-Methyl-3-naphthalen-2-ylmethyl-2,3-dihydro-benzofuran-6-carboxylic acid methyl ester A solution of 4-Iodo-3-(2-methyl-allyloxy)-benzoic acid methyl ester (455 mg, 1.37 mmol) in DMF (15 mL) were added Potassium carbonate (379 mg, 2.74 mmol), Tetrabutylammonium chloride (380 mg, 1.37 mmol), Palladium acetate (25.6 mg, 0.136 mmol) in DMF (5 mL) and 2-Naphthylboronic acid, (282 mg, 1.64 mmol) was submitted to microwave irradiation at 150° C. for 16 minutes. The resulting mixture was filtered over silica, washed with water, dried over MgSO$_4$ and concentrated. Column chromatography (silica gel, heptane/CH$_2$Cl$_2$: 4/6) afforded 100 mg (22%) of the title compound as a slightly brown oil which crystallized.

B) 3-Methyl-3-naphthalen-2-ylmethyl-2,3-dihydro-benzofuran-6-carboxylic acid A mixture of PhD001.125 (80 mg, 0.24 mmol), sodium hydroxide (90 mg, 2.25 mmol), ethanol (4 ml) and water (1 ml) in tetrahydrofuran (4 ml), was stirred for 12 h at room temperature. The reaction medium was acidified by adding a 1.2 M hydrochloric acid solution and extracted with ethyl acetate. The organic phase was washed with water, dried (Na$_2$SO$_4$), and concentrated in a rotary evaporator. The product was obtained as a white solid (M: 52 mg, yield: 68%).

C) (3-Methyl-3-naphthalen-2-ylmethyl-2,3-dihydro-benzofuran-6-yl)-piperidin-1-yl-methanone In a manner similar to that of Example 6, by reacting 3-Methyl-3-naphthalen-2-ylmethyl-2,3-dihydro-benzofuran-6-carboxylic acid (0.225 mmol) previously obtained in Example 15(B), Piperidine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 μL, 0.34 mmol) in DMF (1 mL) expected derivative was obtained as an colorless oil. NMR (CDCl$_3$): δ 1.41 (s, H), 3.04 (d, 2H), 3.34 (br s, 2H), 3.68 (br s, 2H), 4.09 (d, 1H), 4.60 (d, 1H), 6.74 (m, 2H), 6.88 (dd, 1H), 6.95 (d, 2H), 7.12 (dd, 1H), 7.42-7.46 (m, 3H), 7.69-7.74 (m, 2H), 7.79 (dd, 1H).

EXAMPLE 16

[3-((E)-Hex-2-enyl)-3-methyl-2,3-dihydro-benzofuran-6-yl]-piperidin-1-yl-methanone

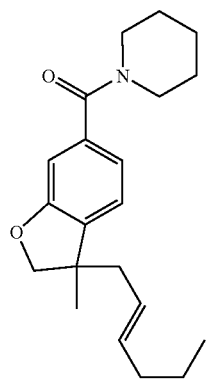 [SMILES: CCC/C=C/CC1(C)COc2cc(C(=O)N3CCCCC3)ccc21]

A) 3-((E)-Hex-2-enyl)-3-methyl-2,3-dihydro-benzofuran-6-carboxylic acid methyl ester To a solution of 4-Iodo-3-(2-methyl-allyloxy)-benzoic acid methyl ester (65 mg, 0.2 mmol) in DMF (2 mL) were added Potassium carbonate (54 mg, 0.39 mmol), Tetrabutylammonium chloride (54 mg, 0.2 mmol), Palladium acetate (3.5 mg, 0.02 mmol) in DMF (5 mL) and 1-Penten-1-ylboronic acid, (26 mg, 0.23 mmol). The resulting mixture was stirred under microwave irradiation (160° C., 15 min), cooled to room temperature, filtered over silica, washed with water, dried over MgSO$_4$ and concentrated. Column chromatography (silica gel, heptane/CH$_2$Cl$_2$: 4/6) afforded title compound as a slightly colorless oil.

B) 3-((E)-Hex-2-enyl)-3-methyl-2,3-dihydro-benzofuran-6-carboxylic acid

A mixture of 3-((E)-Hex-2-enyl)-3-methyl-2,3-dihydro-benzofuran-6-carboxylic acid methyl ester (200 mg, 0.73 mmol), sodium hydroxide (200 mg, 5 mmol), ethanol (7 ml) and water (1 ml) in tetrahydrofuran (7 ml), was stirred for 12 h at room temperature. The reaction medium was acidified by adding a 1.2 M hydrochloric acid solution and extracted with ethyl acetate. The organic phase was washed with water, dried (Na$_2$SO$_4$), and concentrated in a rotary evaporator. The product was obtained as colorless oil which crystallized (M: 155 mg, 82%).

C) [3-((E)-Hex-2-enyl)-3-methyl-2,3-dihydro-benzofuran-6-yl]-piperidin-1-yl-methanone In a manner similar to that of Example 6, by reacting 3-((E)-Hex-2-enyl)-3-methyl-2,3-dihydro-benzofuran-6- carboxylic acid (0.225 mmol) previously obtained in Example 16(B), Piperidine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 μL, 0.34 mmol) in DMF (1 mL) expected derivative was obtained as an colorless oil. NMR (CDCl$_3$): δ 0.86 (t, 3H), 1.23-1.40 (m, 5H), 1.95 (dd, 2H), 2.28 (d, 2H), 3.35 (br s, 2H), 3.34 (br s, 2H), 3.67 (br s, 2H), 4.13 (d, 1H), 4.40 (d, 1H), 5.24-5.34 (m, 1H), 5.40-5.50 (m, 1H), 6.77 (d, 1H), 6.88 (dd, 1H), 7.06 (d, 1H).

EXAMPLE 17

3-((E)-Hex-2-enyl)-3-methyl-2,3-dihydro-benzofuran-6-carboxylic acid cyclohexylamide

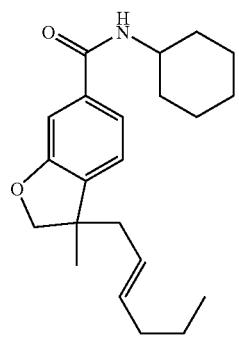 [SMILES: CCC/C=C/CC1(C)COc2cc(C(=O)NC3CCCCC3)ccc21]

In a manner similar to that of Example 6, by reacting 3-((E)-Hex-2-enyl)-3-methyl-2,3-dihydro-benzofuran-6-carboxylic acid (0.225 mmol) previously obtained in Example 16(B), cyclohexylamine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 μL, 0.34 mmol) in DMF (1 mL) expected derivative was obtained as an colorless oil. NMR (CDCl$_3$): δ 0.86 (t, 3H), 1.19-2.03 (m, 13H), 2.28 (d, 2H), 3.89-4.02 (m, 1H), 4.14 (d, 1H), 4.41 (d, 1H), 5.23-5.29 (m, 1H), 5.42-5.47 (m, 1H), 5.85 (d, 1H), 7.09 (d, 1H), 7.11 (d, 1H), 7.27 (dd, 1H).

EXAMPLE 18

3-Methyl-3-naphthalen-1-ylmethyl-2,3-dihydro-benzofuran-6-carboxylic acid cyclohexylamide

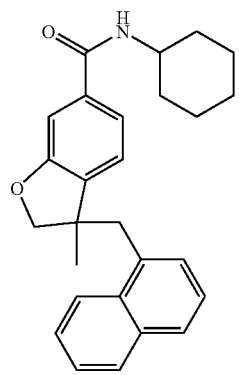 [SMILES: CC1(Cc2cccc3ccccc23)COc2cc(C(=O)NC3CCCCC3)ccc21]

In a manner similar to that of Example 6, by reacting 3-Methyl-3-naphthalen-1-ylmethyl-2,3-dihydro-benzofuran-6-carboxylic acid (0.225 mmol) previously obtained in Example 14(B), cyclohexylamine (0.25 mmol) in dichloromethane (2 mL) and DMF (1 mL), O-(7-Azabenzotriazol-1-yl)-N,N,N',N'-tetramethyluronium hexafluorophosphate (HATU) (94 mg, 0.25 mmol) and a solution of N,N-diisopropylethylamine (44 mg, 59 μL, 0.34 mmol) in DMF (1 mL) expected derivative was obtained as an colorless oil. NMR (CDCl$_3$): δ 1.20-1.59 (m, 11H), 2.00 (d, 2H), 3.38 (dd, 2H), 3.90-3.98 (m, 1H), 4.09 (d, 1H), 4.57 (d, 1H), 5.85 (d, 1H), 6.84 (d, 1H), 7.12-7.17 (m, 3H), 7.33-7.46 (m, 3H), 7.75 (d, 1H), 7.82-7.87 (m, 2H).

EXAMPLE 19

3-Benzyl-3-methyl-6-(piperidine-1-carbonyl)-1,3-dihydro-indol-2-one

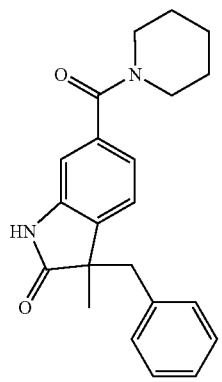 [SMILES: CC1(Cc2ccccc2)C(=O)Nc2cc(C(=O)N3CCCCC3)ccc21]

A) 4-Iodo-3-(2-methyl-acryloylamino)-benzoic acid methyl ester

To a stirred suspension of Methyl 3-amino-4-iodobenzoate (1.67 g, 6 mmol) and Methacrylic acid (568 mg, 6.6 mmol) in dichloromethane (60 mL) and DMF (60 mL) were added O-(7-Azabenzotriazol-1-yl)-N,N,N',N'-tetramethyluronium hexafluorophosphate (HAM) (2.5 g, 6.6 mmol) and then a solution of N,N-diisopropylethylamine (1.16 g, 1560 μL, 9 mmol) in DMF (20 mL). The reaction mixture was stirred at ambient temperature for 24 h. The reaction medium was acidified by adding a 1.2 M hydrochloric acid solution and extracted with ethyl acetate. The organic phase was washed with water, dried (MgSO$_4$), and concentrated to give the amide which was purified by flash chromatography (AcOEt/heptane: 5/5).

B) 3-Benzyl-3-methyl-2-oxo-2,3-dihydro-1H-indole-6-carboxylic acid methyl ester

In a manner similar to that of Example 1B, by reacting 4-Iodo-3-(2-methyl-acryloylamino)-benzoic acid methyl ester (1.37 mmol) obtained in Example 19(A), in DMF (20 mL), potassium carbonate (379 mg, 2.74 mmol), tetrabutylammonium chloride (380 mg, 1.37 mmol), palladium acetate (25.6 mg, 0.136 mmol) and Phenylboronic acid (200 mg, 1.64 mmol), expected derivative was obtained as an colorless oil after purification by flash chromatography (AcOEt/heptane: 4/6).

C) 3-Benzyl-3-methyl-2-oxo-2,3-dihydro-1H-indole-6-carboxylic acid

In a manner similar to that of Example 1C, by reacting 3-Benzyl-3-methyl-2-oxo-2,3-dihydro-1H-indole-6-carboxylic acid methyl ester (1.06 mmol) obtained in Example 19(B), sodium hydroxide (260 mg, 6.5 mmol), ethanol (10 ml) and water (1 ml) in tetrahydrofuran (10 ml), expected derivative was obtained as a white solid.

D) 3-Benzyl-3-methyl-6-(piperidine-1-carbonyl)-1,3-dihydro-indol-2-one

In a manner similar to that of Example 6, by reacting 3-Benzyl-3-methyl-2-oxo-2,3-dihydro-1H-indole-6-carboxylic acid (0.225 mmol) previously obtained in Example 19(C), cyclohexylamine (0.25 mmol) in dichloromethane (2 mL) and DMF (1 mL), O-(7-Azabenzothiazol-1-yl)-N,N,N',N'-tetramethyluronium hexafluorophosphate (HATU) (94 mg, 0.25 mmol) and a solution of N,N-diisopropylethylamine (44 mg, 59 µL, 0.34 mmol) in DMF (1 mL) expected derivative was obtained as an colorless oil after purification by flash chromatography (AcOEt/heptane: 7/3).

EXAMPLE 20

(3-Benzyl-3-methoxymethyl-2,3-dihydro-benzofuran-6-yl)-piperidin-1-yl-methanone

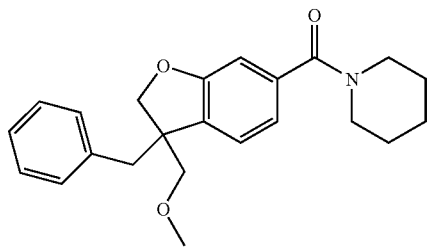 [SMILES: COCC1(Cc2ccccc2)COc2cc(C(=O)N3CCCCC3)ccc21]

A) [3-(2-Chloromethyl-allyloxy)-4-iodo-phenyl]-piperidin-1-yl-methanone

A mixture of Cesium carbonate (940 mg, 2.88 mmol), 3-Hydroxy-4-iodo-benzoic acid methyl ester (400 mg, 1.44 mmol), 3-Chloro-2-chloromethyl-1-propene (360 mg, 2.88 mmol) in dimethylformamide 20 mL was stirred at room temperature for 48 h. The reaction medium was acidified by adding a 1.2 M hydrochloric acid solution and extracted with ethyl acetate. The organic phase was washed with water, dried ($Na_2SO_4$), concentrated in a rotary evaporator and purified by flash chromatography.

B) 1-(4-iodo-3-{[2-(methoxymethyl)prop-2-enyl]oxy}benzoyl)piperidine

To a solution of [3-(2-Chloromethyl-allyloxy)-4-iodo-phenyl]-piperidin-1-yl-methanone (200 mg, 0.48 mmol) in anhydrous methyl ethyl ketone (5.3 mL) was added with Sodium methylate, (124.46 mg, 0.56 mmol). The reaction mixture was heated at 70° C. for 4 h. Additional 0.1 mL of sodium methylate was added after heating the reaction at 80 C for 5 hours. Reaction was left overnight at r.t. The mixture was diluted filtered, washed with water and dried over $MgSO_4$. Evaporation of the solvent and of the remaining bromopropene in vacuo afforded the requisite alkylated ester as a yellow oil. M: 210 mg, Yield: 100% raw. The desired compound was purified by flash chromatography (AcOEt/heptane: 4/6)

C) (3-Benzyl-3-methoxymethyl-2,3-dihydro-benzofuran-6-yl)-piperidin-1-yl-methanone In a manner similar to that of Example 1(B), by reacting 1-(4-iodo-3-{[2-(methoxymethyl)prop-2-enyl]oxy}benzoyl)piperidine (0.4 mmol) obtained in Example 20(B), in DMF (6 mL), potassium carbonate (111 mg, 0.8 mmol), tetrabutylammonium chloride (111 mg, 0.4 mmol), palladium acetate (7 mg, 0.38 mmol) and Phenylboronic acid (60 mg, 0.5 mmol), expected derivative was obtained as an colorless oil after purification by flash chromatography (AcOEt/heptane: 4/6).

Additional compounds of Formula I-V include:

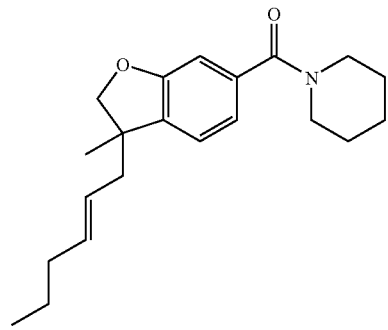

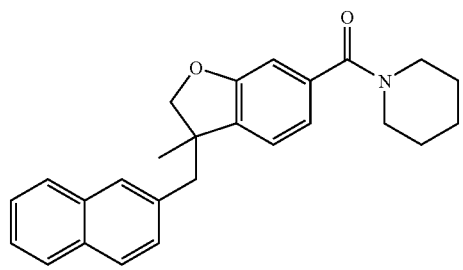

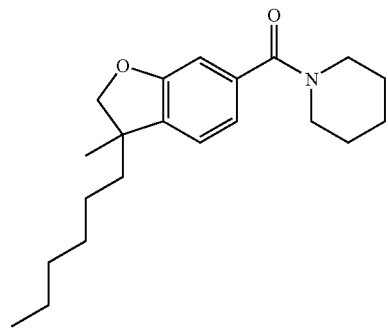

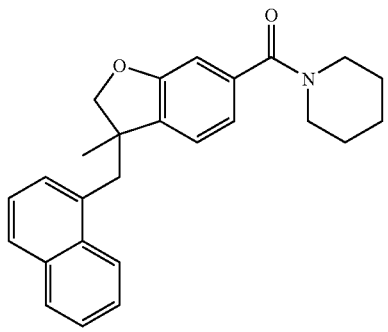
Additional compounds of Formula VI include:
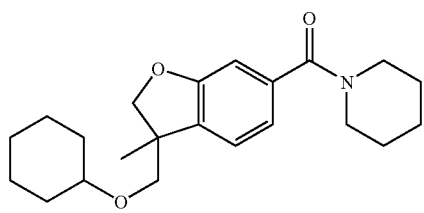
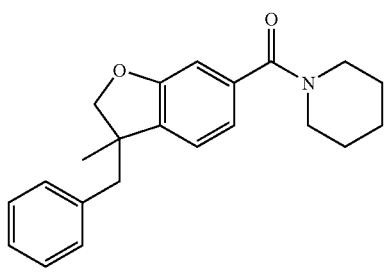
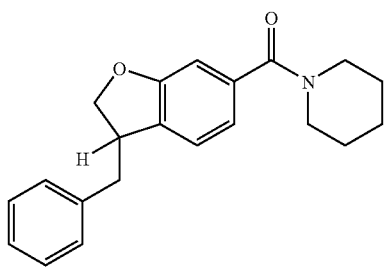
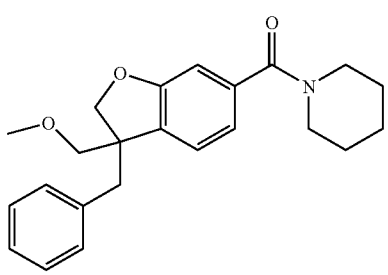
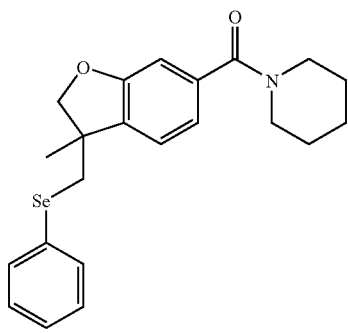
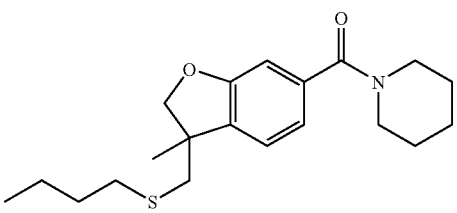
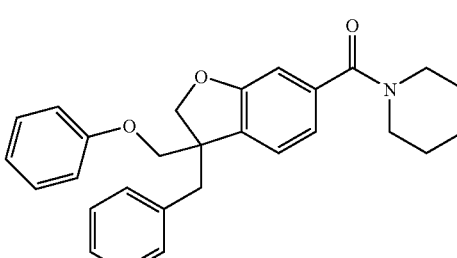
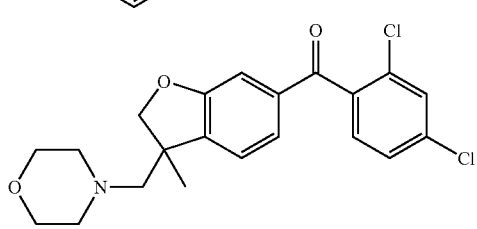
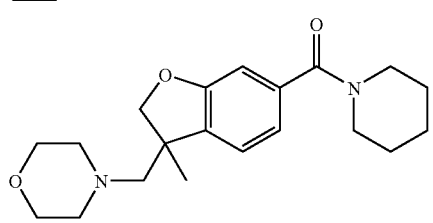
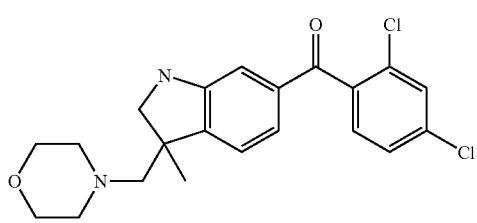
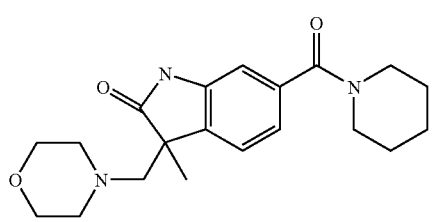

Biological Activity Assay

CB1 Binding Assay

Cell membrane homogenates (25 μg protein) were incubated for 120 min at 37° C. with 0.5 nM [$^3$H]CP 55940 (the reference standard [Rinaldi-Carmona, 1996 #1320]) in the absence or presence of the test compound in a buffer containing 50 mM Tris HCl (pH 7.4), 5 mM $MgCl_2$, 2.5 mM EDTA, and 0.3% bovine serum albumin (BSA). Nonspecific binding was determined in the presence of 10 μM WIN 55212-2. After being incubated, the samples were filtered rapidly under vacuum through glass fiber filters (GF/B; Packard) presoaked with 0.3% PEI and rinsed several times with ice-cold buffer containing 50 mM Tris HCl (pH 7.4) and 0.5% BSA using a 96-sample cell harvester (Unifilter; Packard). The filters were dried then counted for radioactivity in a scintillation counter (Topcount; Packard) using a scintillation cocktail (Microscint 0; Packard). The results were expressed as a percentage of the inhibition of the control radioligand-specific binding. The reference standard compounds were tested in each experiment at several concentrations to obtain a competition curve from which its $IC_{50}$ was calculated.

CB2 Binding Assay

Cell membrane homogenates (15 μg protein) were incubated for 120 mM at 37° C. with 0.8 nM [3H]WIN 55212-2 (the reference standard [Munro, 1993 #1321]) in the absence or presence of the test compound in a buffer containing 50 mM HEPES/Tris HCL (pH 7.4), 5 mM MgCl2, 2.5 mM EGTA, and 0.1% BSA. Nonspecific binding was determined in the presence of 10 μM WIN 55212-2. After being incubated, the samples were filtered rapidly under vacuum through glass fiber filters (GF/B; Packard) presoaked with 0.3% PEI and rinsed several times with ice-cold buffer containing 50 mM Tris HCl (pH 7.4) and 0.5% BSA using a 96-sample cell harvester (Unifilter; Packard). The filters were dried then counted for radioactivity in a scintillation counter (Topcount; Packard) using a scintillation cocktail (Microscint 0; Packard). The results were expressed as a percentage of the inhibition of the control radioligand-specific binding. The reference standard compounds were tested in each experiment at several concentrations to obtain a competition curve from which its $IC_{50}$ was calculated.

CB1/CB2 Functional Assay

A dose response curve was generated at eight concentrations in duplicate on CB1 and CB2 in light of reference agonists. The reference agonists for cannabinoid receptors was CP55,940. See FIGS. 1A, 1B, 2A, 2B, 3A and 3B.

Membranes (CB1, ES-110-MG or CB2, ES-111-MG) were mixed with GDP (volume:volume) and incubated for at least 15 min on ice. In parallel, GTPγ[$^{35}$S] were mixed with the beads (volume:volume) just before starting the reaction. The following reagents were successively added in the wells of an Optiplate: 50 μl of ligand, 20 μl of the membranes:GDP mix, 10 μl of assay buffer for agonist testing and 20 μl of the GTPγ[$^{35}$S]: beads mix. The plates were covered with a topseal, shaken on an orbital shaker for 2 min, and then incubated between 30 to 60 min. at room temperature. Then the plates were centrifuged for 10 min at 2000 rpm, incubated at room temperature between 1 to 4 hours and counted for 1 min with a PerkinElmer TopCount reader.

Using the above-identified assays, the binding data for certain heterocyclic compounds to the CB1 and CB2 receptors have been obtained and is provided in Tables 1, and Table2 below.

TABLE 1

CB1 - Binding Data

| Example No. | % Inhibition of Control Specific Binding | % of Control Specific Binding | | | SEM % Control | Test Concentration (MD) |
|---|---|---|---|---|---|---|
| | | $1^{st}$ | $2^{nd}$ | Mean | | |
| 1 | 14 | 85.7 | 85.3 | 85.5 | 0.2 | 1.0E−05 |
| 2 | 68 | 29.9 | 33.8 | 31.8 | 2 | 1.0E−05 |
| 3 | 71 | 22 | 36 | 29 | 7 | 1.0E−05 |
| 4 | 9 | 85.9 | 95.1 | 90.5 | 4.6 | 1.0E−05 |
| 5 | 43 | 53.5 | 60.8 | 57.2 | 3.7 | 1.0E−05 |
| 6 | 26 | 66.8 | 80.4 | 73.6 | 6.8 | 1.1E−05 |

TABLE 2

CB2 - Binding Data

| Example No. | % Inhibition of Control Specific Binding | % of Control Specific Binding | | | SEM % Control | Test Concentration (MD) |
|---|---|---|---|---|---|---|
| | | $1^{st}$ | $2^{nd}$ | Mean | | |
| 1 | 23 | 78.3 | 74.8 | 76.6 | 1.8 | 1.0E−05 |
| 2 | 85 | 21.3 | 8.6 | 14.9 | 6.4 | 1.0E−05 |
| 3 | 91 | 13 | 5.8 | 9.4 | 3.6 | 1.0E−05 |
| 4 | 15 | 83.9 | 85.5 | 84.7 | 0.8 | 1.0E−05 |
| 5 | 72 | 29.9 | 25.1 | 27.5 | 2.4 | 1.0E−05 |
| 6 | 31 | 71.6 | 67.3 | 69.4 | 2.2 | 1.0E−05 |

Using the above identified functional assay, the activity of the CB1 and CB2 receptors was obtained and is shown in Tables 3 and 4 below. This data is also charted in FIGS. 1 through 3.

TABLE 3

CB1 Functional Activity Activty

| Example No. | % Inhibition of Control Specific Binding CB1 | EC50 (nM) for GTP Binding | % Activation Average | Compound Function |
|---|---|---|---|---|
| 2 | 68 | 0 | −35.79 | Inverse Agonist |
| 3 | 71 | 0 | 22.85 | Agonist |
| 5 | 43 | 0 | −36.02 | Inverse Agonist |

TABLE 4

CB2 Functional Activity Data

| Example No. | % Inhibition of Control Specific Binding CB2 | EC50 (nM) for GTP Binding | % Activation Average | Compound Function |
|---|---|---|---|---|
| 2 | 85 | 478.69 | 52.94 | Agonist |
| 3 | 91 | 160.09 | 87.2 | Agonist |
| 5 | 72 | 408.51 | 55.71 | Agonist |

In Vivo Testing

I. Assessment of Mechanical Allodynia in Rats

All experiments were performed on male Sprague-Dawley rats (200-250 g). Rats were housed individually in plastic cages with soft bedding at room temperature and maintained on a 12-hour light-dark cycle with free access to food and water.

Surgical Procedures

All surgical procedures were performed with the rats anesthetized inhalational isoflurane in 100% oxygen, induced at 5% and maintained at 2%. Animals that show neurologic deficits after surgery were excluded from the study. Prophylactic antibiotic (enrofloxacin 5 mg/kg subcutaneously) and analgesic (buprenorphine, 0.2-0.5 mg/kg, or morphine, 2.5 mg/kg, both given subcutaneously) were administered once daily for 3 days. Lumbar 5/6 Spinal-Nerve Ligation (Nerve-Ligation Model)

Neuropathic pain was induced following the methods of Kim and Chung. Kim S H, Chung J M. *An experimental model for peripheral neuropathy produced by segmental spinal nerve ligation in the rat*. Pain 1992; 50:355-63. Rats were anesthetized and placed prone under a microsurgical apparatus. A midline incision was made on the back, and the right paraspinal muscles were separated from the spinous processes at the L4S2 levels. The L6 transverse process was carefully removed, and the L4/5 spinal nerves were identified. The L5 nerve was tightly ligated with a 6-0 silk suture. The right L6 spinal nerve was then located just caudal and medial to the sacroiliac junction and tightly ligated with a silk suture.

Intrathecal Catheterization

Two weeks later after spinal nerve ligation, Intrathecal catheters (PE-10 tubing) was inserted into the rats while they were anesthetized with isoflurane, as described by Yaksh and Rudy. Yaksh T L, Rudy T A. *Chronic catheterization of the spinal subarachnoid space*. Physiology & Behavior 1976; 17:1031-6. A midline incision was made on the back of the neck. The muscle was freed at the attachment to the skull exposing the cisternal membrane. The membrane was opened with a stab blade and an 8.5 cm polyethylene (PE-10) catheter was then inserted through the cisternal opening, and passed carefully and caudally into the intrathecal space at the L1-L3 spinal segments. The end of the catheter was tunneled through the subcutaneous space over the frontal bones, flushed with 10 μl saline, and then plugged with a short length of wire. Animal testing was performed 5-7 days after intrathecal catheter placement.

Results

To assess mechanical allodynia, the mechanical paw withdrawal threshold was measured with a series of von Frey hairs (range 0.4-15 g). Rats were placed in elevated Perspex enclosures (28 cm×15 cm×18 cm) with wire mesh bases and given 15-20 min to acclimatize to the testing environment. Rats will be allowed to acclimatize for 30 min in a clear plastic cage with a wire mesh bottom. The calibrated von Frey filament fibers were applied to the hindpaw briefly for 6 seconds to determine the paw withdrawal threshold before and after drug injection (intraperitoneally or intrathecally). A series of von Frey filaments with exponentially incremental stiffness (0.4, 0.7, 1.2, 2.0, 3.6, 5.5, 8.5 and 15 g) were used to measure the 50% threshold for hindpaw withdrawal in awake, unrestrained rats. Chaplan S R, Bach F W, Pogrel J W, Chung J M, Yaksh T L. Quantitative assessment of tactile allodynia in the rat paw. Journal of Neuroscience Methods 1994; 53:55-63. Brisk paw withdrawal from the pressure of a filament gently bent against the plantar paw was defined as a positive response, and absence of withdrawal within 6 s as a negative response. Filaments were touched to the hindpaw in sequential ascending or descending order until the threshold of response is crossed (allowing about 10 s between each increment of the von Frey filaments). Each time the threshold is crossed, the direction of stimulus presentation was reversed and the procedure will be resumed. Four responses were collected after the first threshold detection, and the 50% withdrawal thresholds were interpolated. In cases where response thresholds fell outside the range of detection, 15.00 and 0.25 g were, respectively, assigned for continuous negative or positive responses to the limit of stimuli.

Drugs

The compound of Example 3 was prepared in dimethyl sulfoxide (DMSO).

Results

Figure 4:
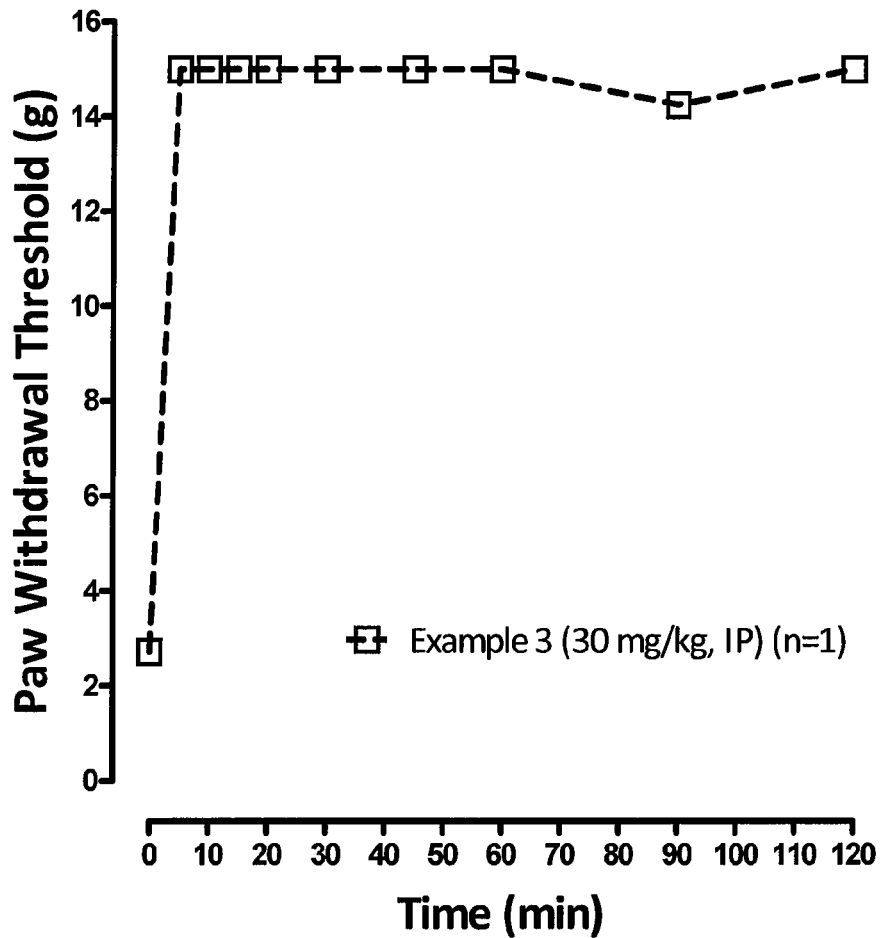
FIG. 4 shows paw withdrawal threshold versus time for IP administered compound of Example 3.

IP administration of 30 mg/kg in 0.5 ml of the compound of Example 3 as shown in FIG. 4 produced an increase in mechanical paw withdrawal threshold. The peak effect for both drugs was noted within 5 min following IP administration. The high threshold (15 g) was maintained beyond the 2-h observation period for the compound of Example 3.

Figure 5:
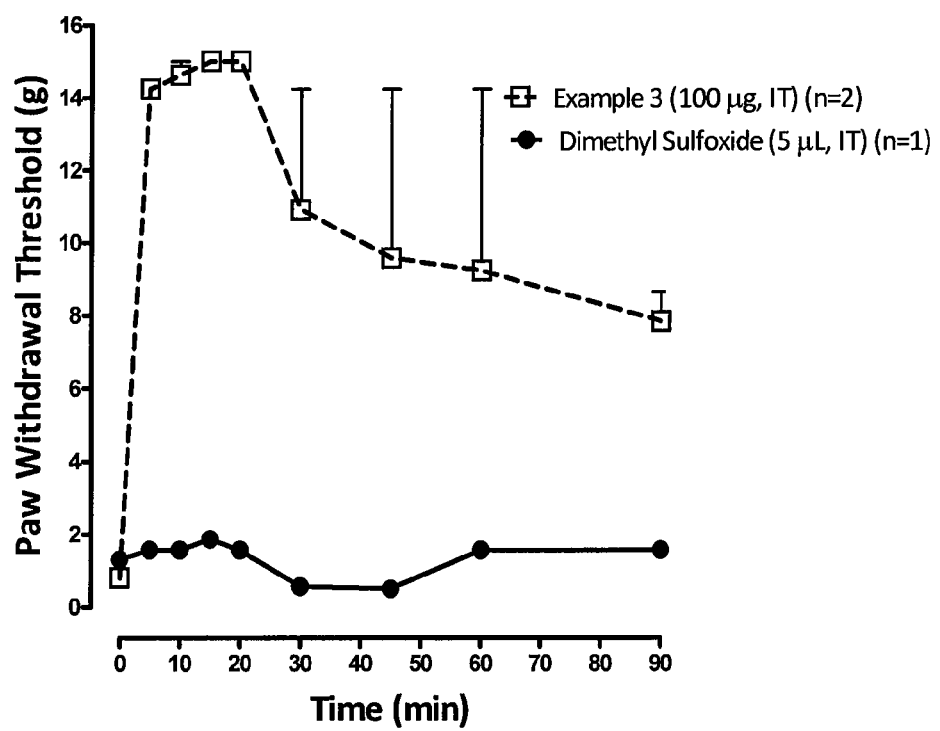
FIG. 5 shows paw withdrawal threshold versus time for IT administered compound of Example 3.

IT administration of the compound of Example 3 as shown in FIG. 5 produced an increase in mechanical paw withdrawal threshold that lasted for the 90-min observation period. No behavioral abnormalities or side effects were noted in animals.

Figure 6:
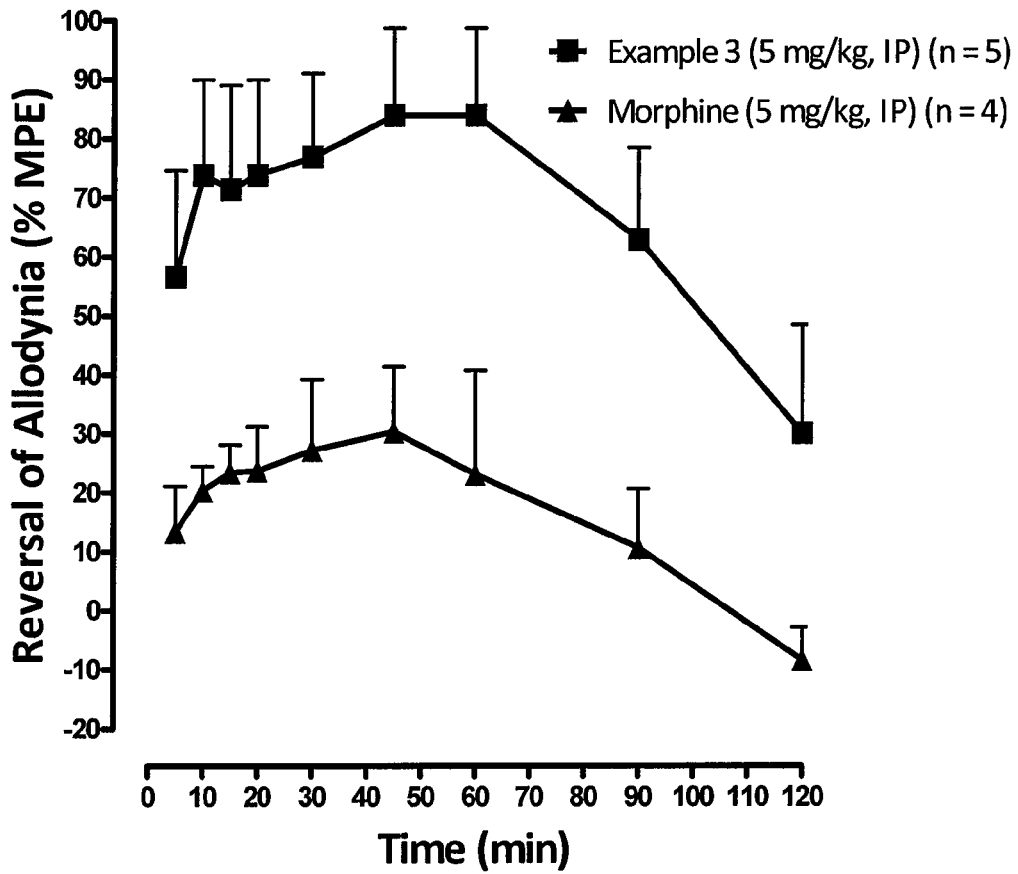
FIG. 6 shows reversal of allodynia as a function time with IP administered compound of Example 3 and IP administered morphine.

Intraperitoneal (IP) administration of the compound of Example 3 compared to morphine is shown in FIG. 6.

Conclusions

The compound of Example 3 is a very potent analgesic in the neuropathic pain animal model when administered IP. The compound of Example 3 appears to be a longer-acting compound.

II. In Vitro Receptor Radioligand Binding Studies

AM630 and AM251 were purchased from Tocris Bioscience (Ellisville, Mich., USA). AM1241 and naloxone were purchased from Sigma-Aldrich Corp. (St. Louis, Mo., USA).

WIN 55, 212-2, AM1241, paclitaxel, and all chemicals used for synthesis of the compound of Example 3 were purchased from Sigma-Aldrich, St. Louis, Mo.

Figure 7:
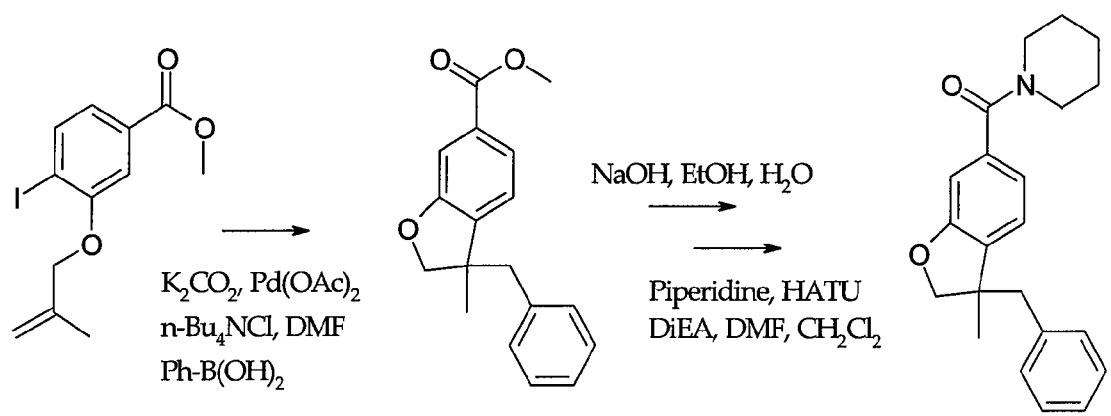
FIG. 7 shows the synthetic steps of making the compound of Example 3 as used in in vitro and in vivo biological studies.
Figure 8A:
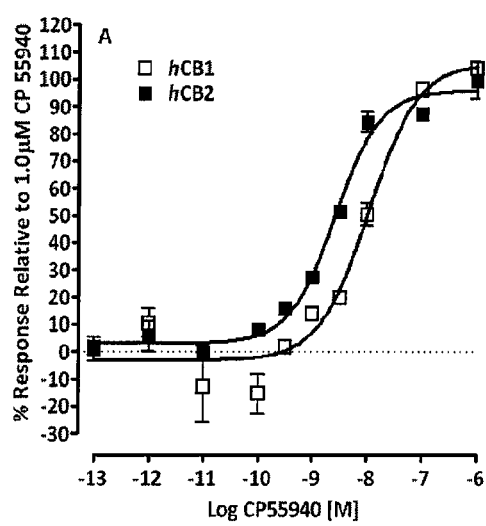
FIGS. 8A and 8B show the characterization of CP55,940 (FIG. 8A) and the compound of Example 3 (FIG. 8B) in recombinant human CB1 and CB2 GTPγ[$^{35}$S] assay systems. Levels of receptor activation are calculated and are expressed as a percentage relative to the response of 1 µM CP55,940.
Figure 8B:
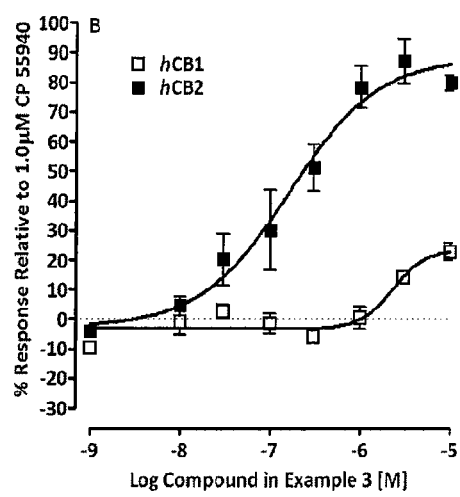

The compound of Example 3 was synthesized as shown in FIG. 7. Briefly, the 3-hydroxy-4-iodo-benzoic acid was obtained by iodination (NaI, NaOCl, NaOH, MeOH, 80% yield) of meta-hydroxybenzoic acid. The corresponding methyl benzoate was obtained by esterification (MeOH, $H_2SO_4$). The phenol derivative was then coupled with 3-bromo-2-methyl-propene using potassium carbonate in methylethylketone in 98% yield. The resulting compound was submitted to a Pd-catalyzed tandem cyclization/Suzuki-coupling reaction to afford the corresponding heterocyclic in 95% yield. Szlosek-Pinaud, M., et al., *Efficient Synthetic Approach to Heterocycles Possessing the 3,3-Disubstituted-2,3-Dihydrobenzofuran Skeleton Via Diverse Palladium-Catalyzed Tandem Reactions*, Tetrahedron, 2007, 63:3340-9. The compound of Exhibit 3 was obtained after saponification (97% yield) and coupling with piperidine (71% yield).

Analytical Data for the Compound of Example 3

1-[(3-benzyl-3-methyl-2,3-dihydro-1-benzofuran-6-yl) carbonyl]piperidine, $^1$H NMR (CDCl$_3$): δ 1.37 (s, 3H), 1.58-1.69 (m, 6H), 2.8 (d, J=13.5 Hz, 1H), 2.90 (d, J=13.5 Hz, 1H), 3.34 (br s, 2H), 3.68 (br s, 2H), 4.09 (d, J=8.7 Hz, 1H), 4.53 (d, J=8.7 Hz, 1H), 6.75 (d, J=1.2 Hz, 1H), 6.88 (dd, J=1.2 Hz, J=7.5 Hz) 6.94 (d, J=7.5 Hz, 1H), 6.99-7.02 (m, 2H), 7.22-7.24 (m, 3H). $^{13}$C NMR (CDCl$_3$): δ 24.56 (CH$_3$), 24.64 (CH$_2$), 25.67 (CH$_2$), 26.56 (CH$_2$), 43.15 (CH$_2$), 46.22 (C), 46.57 (CH$_2$), 48.75 (CH$_2$), 82.28 (CH$_2$), 108.20 (CH), 119.09 (CH), 123.43 (CH), 126.58 (CH), 127.99 (CH), 130.36 (CH), 136.21 (C), 136.75 (C), 137.26 (C), 159.47 (C), 170.19 (C=O). HRMS (ES+) calcd for $C_{22}H_{25}NO_2$ (M+H$^+$), m/e, 336.1964; found, 336.1958.

The compound of Example 3 was screened in a competitive binding experiment using membranes of Chinese hamster ovarian cells (CHO-K1) expressing selectively the human CB1 receptor, at different concentrations, in duplicate. Mukherjee, S., et al., *Species Comparison and Pharmacological Characterization of Rat and Human CB2 Cannabinoid Receptors*, Eur J Pharmacol, 2004, 505:1-9. The competition binding experiment was performed in 96 well plates (Masterblock®, Catalogue number 786201, Greiner Bio-One) containing binding buffer (50 mM Tris pH 7.4, 2.5 mM EDTA, 0.5% protease free BSA, saponine 10 µg/ml), recombinant membrane extracts (2 µg protein/well) and 1 nM [$^3$H] SR141716A (GE Healthcare, TRK1028, 42 Ci/mmol, diluted in binding buffer). Non-specific binding is determined in the presence of 10 µM CP55,940 (Tocris, Bioscience, Ellisville, Mich., USA). The sample is incubated in a final volume of 0.1 ml for 60 min at 25° C. and then filtered on GF/C Unifilter microplate (Perkin Elmer, Catalogue number 6005177) presoaked in 0.05% Brij for 2 hrs at room temperature. Filters are washed six times with 4 ml of cold binding buffer and bound [$^3$H] SR141716A is determined by liquid scintillation counting. IC$_{50}$ were determined by non-linear regression using one site competition equation. The inhibition constants (Ki) were calculated using the Cheng Prusoff equation (Ki=IC$_{50}$/(1+(L/K$_D$)), where L=concentration of radioligand in the assay, and K$_D$=affinity of the radioligand for the receptor).

The compound of Example 3 was screened in a competitive binding experiment using membranes of Chinese hamster ovarian cells (CHO-K1) expressing selectively the human CB2 receptor, at different concentrations, in duplicate. Mukherjee, S., et al., *Species Comparison and Pharmacological Characterization of Rat and Human CB2 Cannabinoid Receptors*, Eur J Pharmacol, 2004, 505:1-9. The competition binding experiment was performed in 96 well plates (Masterblock®, Catalogue number 786201, Greiner Bio-One) containing binding buffer (50 mM Tris pH 7.4, 2.5 mM EDTA, 0.5% protease free BSA), recombinant membrane extracts (0.25 µg protein/well) and 1 nM [$^3$H]CP 55,940 (Perkin Elmer, NEX-1051, 161 Ci/mmol, diluted in binding buffer). Non-specific binding is determined in the presence of 10 µM CP55940 (Tocris, Bioscience, Ellisville, Mich., USA). The sample is incubated in a final volume of 0.1 ml for 60 min at 30° C. and then filtered on GF/B Unifilter microplate (Perkin Elmer, Catalogue number 6005177) presoaked in 0.5% PEI for 2 hrs at room temperature. Filters are washed six times with 4 ml of cold buffer (50 mM Tris pH 7.4, 2.5 mM EDTA, 0.5% protease free BSA) and bound [$^3$H]CP55940 is determined by liquid scintillation counting. IC$_{50}$ were determined by non-linear regression using one site competition equation. The inhibition constants (Ki) were calculated using the Cheng Prusoff equation (Ki=IC$_{50}$/(1+(L/K$_D$)), where L=concentration of radioligand in the assay, and K$_D$=affinity of the radioligand for the receptor).

GTPγ[$^{35}$S] Functional Assays

Functional activity was evaluated using GTPγ[$^{35}$S] assay in CHO membrane extracts expressing recombinant hCB1 (human CB1) receptors or hCB2 (human CB2) receptors. The assay relies on the binding of GTPγ[$^{35}$S], a radiolabeled non-hydrolyzable GTP analogue, to the G protein upon binding of an agonist of the G-protein-coupled receptor. In this system, agonists stimulate GTPγ[$^{35}$S] binding whereas neutral antagonist have no effect and inverse agonists decrease GTPγ[$^{35}$S] basal binding.

The compound of Example 3 was solubilized in 100% DMSO at a concentration of 10 mM within 4 hours of the first testing session (master solution). A predilution for the dose response curve was performed in 100% DMSO and then diluted 100 fold in assay buffer at a concentration 2 fold higher than the concentration to be tested. The compound of Example 3 was tested for agonist and antagonist activities at eight concentrations in duplicate: 10, 3, 1, 0.3, 0.1, 0.03, 0.01 and 0.001 µM with CP55,940 (Tocris, Bioscience, Ellisville, Mich., USA) as reference agonist. For GTPγS membranes were mixed with GDP diluted in assay buffer to give 30 µM solution (volume:volume) and incubated for at least 15 min on ice. In parallel, GTPγ[$^{35}$S] (GE Healthcare, Catalogue number SJ1308) were mixed with the beads (PVT-WGA (GE Healthcare, RPNQ001)), diluted in assay buffer at 50 mg/ml (0.5 mg/10 µl) (volume:volume) just before starting the reaction. The following reagents were successively added in the wells of an Optiplate (Perkin Elmer): 50 µL of ligand or the reference antagonist (AM251), 20 µl of the membranes:GDP mix, 10 µL of reference agonist (CP55,940) at historical EC$_{80}$ (30 nM), and 20 µl of the GTPγ[$^{35}$S]:beads mix. The plates were covered with a topseal, shacked on an orbital shaker for 2 min, and then incubated for 1 hour at room temperature. Then the plates were centrifuged for 10 min at 2000 rpm and counted for 1 min/well with a PerkinElmer TopCount reader. Assay reproducibility was monitored by the use of reference compound CP55,940. For replicate determinations, the maximum variability tolerated in the test was of ±20% around the average of the replicates. Efficacies (E$_{max}$) for CB1 or CB2 are expressed as a percentage relative to the efficacy of CP55, 940.

cAMP Activation Assays

The compound of Example 3 was tested for agonist activity at the rat CB1 (rCB1) and rCB2 receptors, at eight concentrations, in duplicate: 10, 3, 1, 0.3, 0.1, 0.03, 0.01 and 0.001 µM. Recombinant cells grown to mid-log phase in culture media without antibiotics were detached with PBS containing 5 mM EDTA, centrifuged and resuspended in assay buffer at a concentration of 16.6×105 cells/ml. The test was performed in 96 well plates. For testing, 12 μl of cells (2×10$^3$ cells/well) were mixed with 12 μl of agonist at increasing concentrations. After incubation for 10 min at room temperature, 6 μl of the reference agonist (CP55,940) were added at a final agonist concentration corresponding to the historical EC$_{80}$. The plates were then incubated for 30 min at room temperature. After addition of the lysis buffer, cAMP concentrations were estimated, according to the manufacturer specification, with the HTRF kit from Cis-Bio International (Catalogue number 62AM2PEB).

In Vivo Biological Activity Studies

Adult, male Sprague Dawley (Harlan Sprague Dawley, Indianapolis, Ind.) rats weighing 120-150 gm were used in experimental procedures approved by the Animal Care and Use Committee of the M. D. Anderson Cancer Center, University of Texas. Animals were housed three per cage on a 12/12 hr light/dark cycle with water and food pellets available ad libitum.

Lumbar 5/6 Spinal Nerve Ligation Pain Model

All surgical procedures were performed under deep isoflurane anesthesia in 100% O2. The spinal nerve ligation (SNL) was performed as described previously. Kim, S. H., et al., *An Experimental Model for Peripheral Neuropathy Produced by Segmental Spinal Nerve Ligation in the Rat*, Pain, 1992, 50:355-63. Briefly, a midline incision above the lumbar spine exposed the left L6 transverse process. The process was then removed, the left L5 and L6 spinal nerves were isolated, and both nerves were tightly ligated with 6-0 silk. Prophylactic antibiotic (norfloxacin 5 mg/kg subcutaneously) and analgesic (buprenorphine, 0.2-0.5 mg/kg, or morphine, 2.5 mg/kg, given subcutaneously) were administered once daily for 3 days. All the experiments were conducted 10-14 days after spinal nerve ligation.

Paclitaxel-Induced Neuropathy Model

Groups of rats received daily i.p. injections of either vehicle or 1.0 mg/kg paclitaxel daily for four consecutive days for a final cumulative dose of 4 mg/kg; using an injection volume of 1 ml/kg. Polomano, R. C., et al., *A Painful Peripheral Neuropathy in the Rat Produced by the Chemotherapeutic Drug, Paclitaxel*, Pain, 2001, 94:293-304. The vehicle used in our experiments was the same vehicle used clinically for paclitaxel injections and is composed of a mixture of 10% saline and Cremophor EL® and ethylene oxide. Baseline responses to mechanical stimulation of the hindpaw (see below) were established on day zero and continued daily until the development of neuropathy was confirmed.

Assessment of Mechanical Withdrawal Thresholds

Rats were placed in a compartment with a wire mesh bottom and allowed to acclimate for a minimum of 30 min before testing. Mechanical sensitivity was assessed using a series of Von Frey filaments with logarithmic incremental stiffness (0.41, 0.70, 1.20, 2.00, 3.63, 5.50, 8.50, and 15.1 g) (Stoelting, Wood Dale, Ill.) as previously described, and 50% probability withdrawal thresholds were calculated with the up-down method. Chaplan, S. R., et al., *Quantitative Assessment of Tactile Allodynia in the Rat Paw*, J. Neurosci. Methods, 1994, 53:55-63; Dixon, W., *The Up-and-Down Method for Small Samples*, J. Am. Stat. Assoc., 1965, 60:967-78. In brief, beginning with the 2.0-g probe, filaments were applied to the plantar surface of a hind paw for 6-8 s, in an ascending or descending order after a negative or positive withdrawal response, respectively. Six consecutive responses from the first change in the response were used to calculate the withdrawal threshold (in grams). In cases where response thresholds fell outside the range of detection, 15.00 and 0.25 g were, respectively, assigned for continuous negative or positive responses to the limit of stimuli. The percent maximal possible effect (% MPE) was calculated as ([postdrug threshold–baseline threshold]/[cutoff threshold (15 g)–baseline threshold])×100.

Assessment of Thermal Paw Withdrawal Latencies

To determine sensitivity to noxious heat, rats were placed in plexiglas enclosures on a transparent glass surface maintained at 30° C. and allowed to acclimate for 30 min. A thermal testing apparatus, consisting of a heat-emitting projector lamp and an electronic timer, was used. The device was activated after the lamp is placed directly beneath the planter surface of the hindpaw. The paw withdrawal latency in response to the radiant heat was recorded by a digital timer. A cutoff of 30 s was used to prevent potential tissue damage. After the baseline was measured, three groups of naïve rats (n=10) received 1.0, 3.0, or 10 mg/kg of the compound of Example 3i.p. Response latencies were determined twice for each rat before drug injection and at 5, 10, 15, 30, 45, 60, 90 and 120 min after IP injection. The percent maximal possible effect (% MPE) was calculated as ([postdrug latency–baseline latency]/[cutoff time (30 s)–baseline latency])×100.

Open Field Chamber Testing

The automated open-field chamber (Med Associates ENV-515 Test Environment, St. Albans, Vt.) 43.2×43.2×30.5 cm (L×W×H) equipped with three pairs of 16 infrared arrays that continually monitored the animal's movement was used to determine potential CNS effects of the compound of Example 3, WIN55212-2, and haloperidol in naïve rats. Rats were individually tested 15 min after i.p. drug administration. The infrared beams were set 2.5 cm apart horizontally and at a height of 3 cm above the floor, with the rearing array set at 12 cm from the floor. The area in the box was divided into 4 equal quadrants (zones), with data collected within each quadrant and across quadrants (zone entries). An ambulatory movement was defined as a motion of at least 5 cm and was coded by quadrant. Vertical movements were counted when the rat moved vertically a minimum of 12 cm from the floor. Zone entries were defined as an entry into a zone (from another zone). Entry into a zone was counted when the rat was far enough into the zone to break 2 sets of photoelectric beams for the new zone beams during an ambulatory movement.

Data Analysis

Statistical analyses were carried out using BMDP 2007 (Statistical Solutions, Saugus, Mass., USA) and Graph Pad Prism (version 4.03; Graph Pad Software Inc., San Diego, Calif., USA). Data were analyzed using one-way ANOVA, repeated measures ANOVA, or t-test where appropriate. If ANVOA was significant, Tukey-Kramer post hoc analysis was used for multiple group comparison. Area under the curve (AUC) was calculated using the trapezoidal rule. The results are presented as mean±s.e. mean and were considered significant at P<0.05. Analyses of the dose-response curves and statistics were obtained using the pharmacologic software programs of Tallarida and Murray and included calculation of the ED$_{50}$ values and their 95% confidence intervals (CI). Tallarida, R. J., et al., *Manual of Pharmacologic Calculations With Computer Programs*, Second ed. New York: Springer-Verlag, 1987.

Results

In Vitro Characterization of the Compound of Example 3

In the competition binding assays performed in membranes of CHO expressing selectively the hCB2 receptor, the compound of Example 3 displaced [$^3$H]CP55,490 from human receptors with Ki values of 422±123 nM. The compound of Example 3 did not demonstrate detectable radioactive ligand displacement at hCB1 receptors (up to 10 μM). See Table 5 immediately below.

TABLE 5

Radioligand Competition Binding Assays

| Ligands | Mean Ki (nM) | |
|---|---|---|
| | hCB1 | hCB2 |
| Compound of Example 3 | >10,000 | 422 ± 123 |
| CP55,940 | 3.4 | 1.8 ± 1.1 |

The $EC_{50}$ value of the compound of Example 3 in GTPγ [$^{35}$S] functional assays was 128±32 nM at hCB2 with an Emax of 88%. The compound of Example 3 did not result in any agonistic or antagonistic activities at hCB1 receptors. In cAMP activation assays, the compound of Example 3 had an $EC_{50}$ of 21.7±7.9 nM at rCB2 receptors. The compound of Example 3 did not exhibit any activity at rCB1 receptors. See Table 6 immediately below.

TABLE 6

GTPγ[$^{35}$S] Functional and cAMP Activation Assays

Agonist $EC_{50}$ (mean ± s.e. mean) relative to CP55,490 (%)

| Ligands | GTPγ[$^{35}$S] functional assays | | cAMP activation assays | |
|---|---|---|---|---|
| | hCB1 | hCB2 | rCB1 | rCB2 |
| Compound of Example 3 | >10,000 | 128 ± 32 | >10,000 | 21.7 ± 7.9 |
| CP55,940 | 9 ± 1.3 | 6.5 ± 2.1 | 0.14 ± 0.1 | 1.13 ± 0.13 |

Effects of the Compound of Example 3 in Naïve Rats

Figure 9:
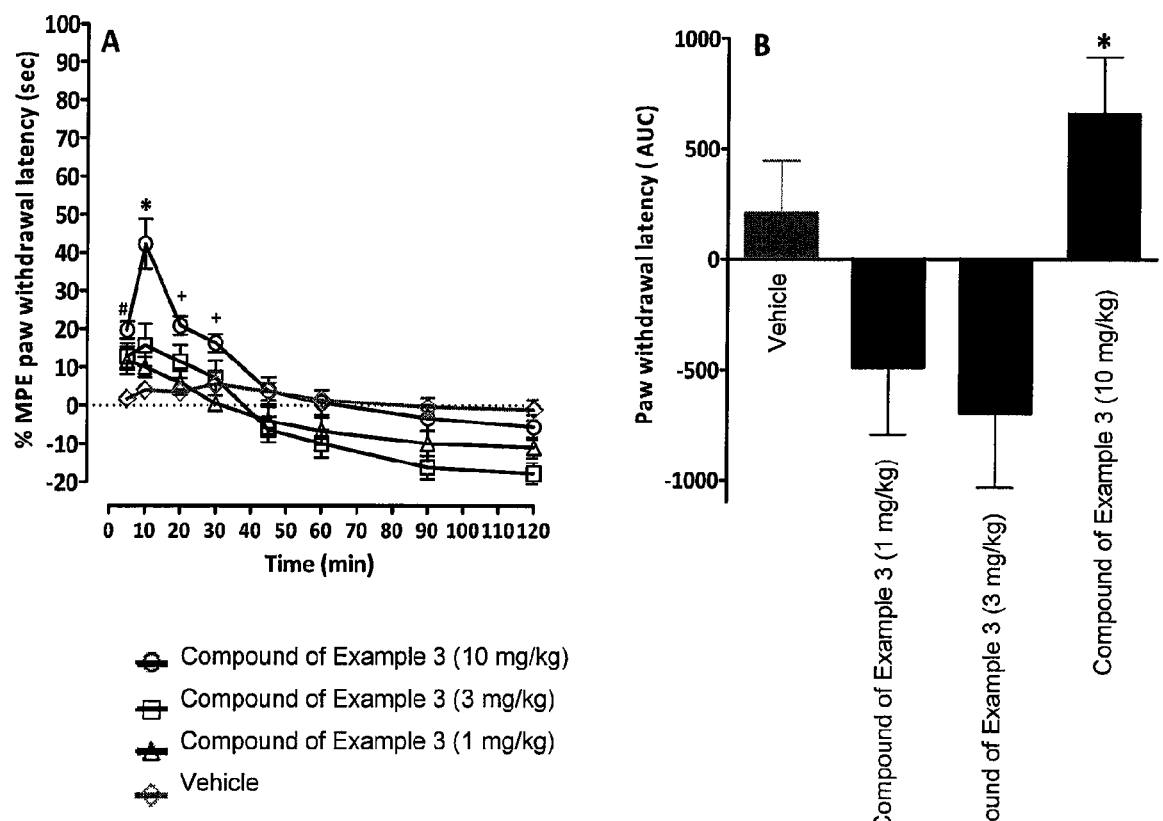
FIG. 9 shows the effects of different doses of the compound of Example 3 (i.p.) on thermally evoked hind paw withdrawal latency in naïve rats (n=10 per group). (A) The time course of percent maximal possible effect (% MPE) and (B) the area under the curve (AUC) of 1.0, 3.0, and 10 mg/kg of the compound of Example 3 and the vehicle. #P<0.01 as compared to the vehicle. *P<0.001 as compared to 1.0 or 3.0 mg/kg of the compound of Example 3 and to the vehicle. $^{+}$P<0.05 as compared to 1.0 mg/kg of the compound of Example 3 and the vehicle. Each point represents the mean±s.e. mean.

Administration of 1 mg/kg or 3 mg/kg of the compound of Example 3 i.p. did not block the nociceptive effect of a thermal stimulus applied to hind paws of naïve rats. Increasing the dose of the compound of Example 3 to 10 mg/kg i.p. resulted in a short-lasting antinociceptive effect (FIG. 9).

Effects of the Compound of Example 3 on Tactile Allodynia in a SNL Neuropathic Pain Model In rats, SNL produced tactile allodynia one week following surgery as demonstrated by a reduction in paw withdrawal threshold to mechanical stimulation to 2.5±0.19 g using Von Frey filaments (FIG. 10A). The compound of Example 3 treatment attenuated tactile allodynia in a dose-related manner with an $ED_{50}$ of 7.48 mg/kg i.p. (95% CI=5.6-9.9 mg/kg). The higher doses (10 mg/kg and 15 mg/kg) produced significantly antiallodynic effect than that noted with 5 mg/kg of the compound of Example 3 (FIGS. 11A, 11B & 11C).

Figure 12:
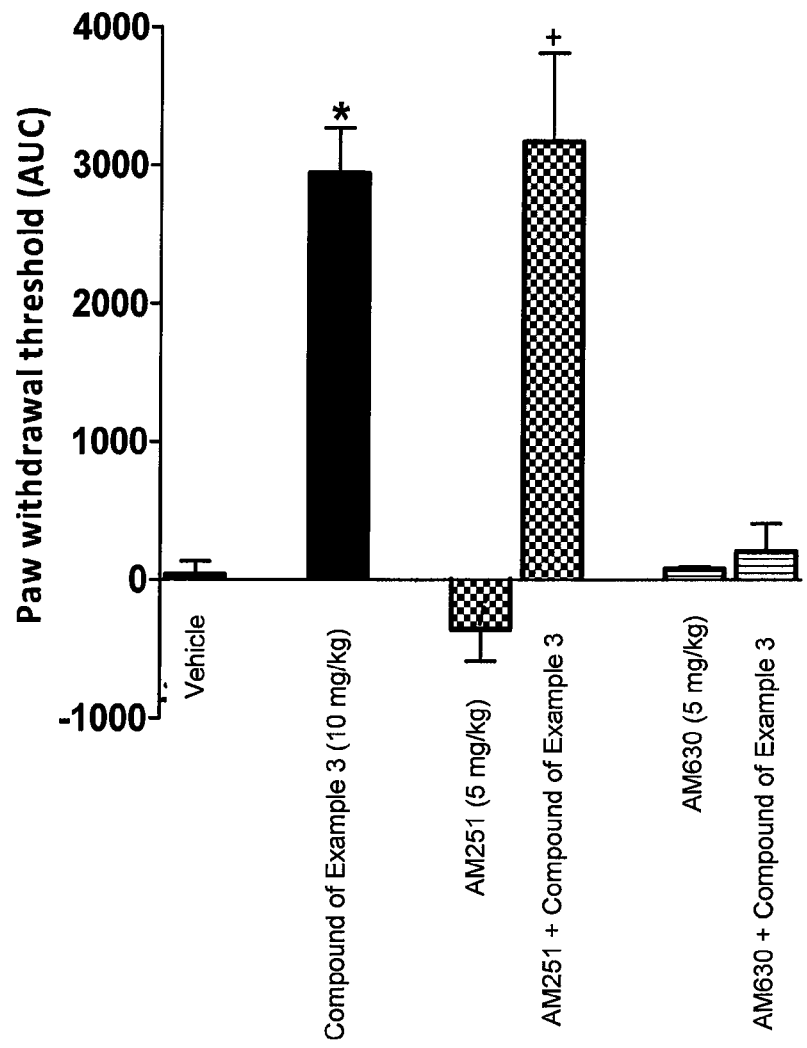
FIG. 12 shows the effects of CB1 and CB2 selective antagonists on the antiallodynic effects of 10 mg/kg of the compound of Example 3i.p. in a spinal nerve ligation neuropathic pain model in rats (n=6 per group). I.p. administration of 5 mg/kg of AM251, a CB1 antagonist or a 5 mg/kg of AM630, a selective CB2 antagonist alone had no effect. Administration of 5 mg/kg AM600 i.p. 15 min prior to the administration of 10 mg/kg of the compound of Example 3i.p. reversed the antiallodynic effects of the compound of Example 3 (AM630+ the compound of Example 3 group). Pretreatment with 5 mg/kg AM251 i.p. followed 15 min later by 10 mg/kg of the compound of Example 3i.p. did not affect the antiallodynic effects of the compound of Example 3 (AM251+ the compound of Example 3 group). *P<0.001 as compared to vehicle, AM251, AM630, and AM630+ the compound of Example 3 groups. $^{+}$P<0.001 as compared to vehicle and AM251 groups.

The receptor specificity of the compound of Example 3 was investigated in SNL model using receptor-selective antagonists (FIG. 12). Pretreatment with AM630 (5 mg/kg i.p.), a CB2 receptor-selective antagonist, significantly reversed antiallodynic effects induced by i.p. administration of 10 mg/kg the compound of Example 3 (P<0.001). Hosohata, Y., et al., *AM630 Antagonism of Cannabinoid-Stimulated [$^{35}$S] GTP Gamma S Binding in the Mouse Brain*, Eur. J. Pharmacol, 1997, 321:R1-3; Ross, R. A., et al., *Agonist-Inverse Agonist Characterization at CB1 and CB2 Cannabinoid Receptors of L759633, L759656, and AM630*, Br. J. Pharmacol., 1999, 126:665-72. In contrast, pretreatment with AM251 (5 mg/kg i.p.), a selective CB1 receptor antagonist, had no effect on the antiallodynic effects induced by the compound of Example 3. Gatley, S. J., et al., *123I-labeled AM251: A Radioiodinated Ligand Which Binds In Vivo to Mouse Brain Cannabinoid CB1 Receptors*, Eur J Pharmacol, 1996, 307:331-8. The rats treated with CB1 or CB2 receptor antagonists alone at the doses used in the present studies did not exhibit any change in paw withdrawal threshold as compared with the vehicle-treated animals (FIG. 12).

Figure 13:
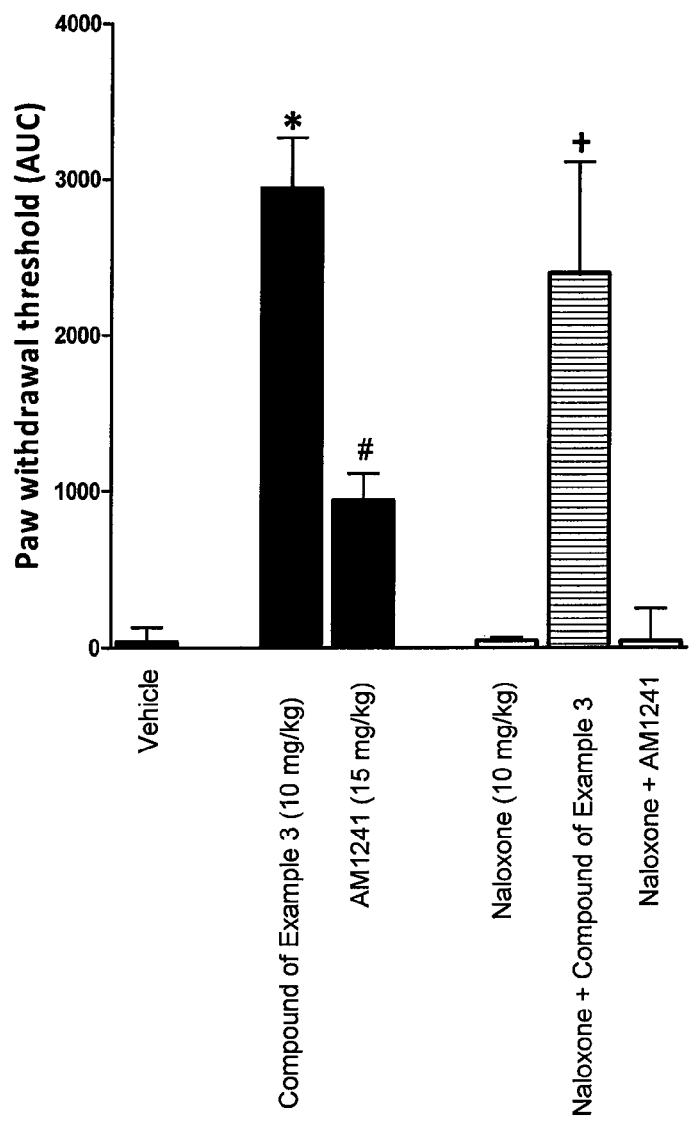
FIG. 13 shows the effects of the opioid antagonist naloxone on the compound of Example 3 and AM1241-induced antiallodynic effects in a spinal nerve ligation neuropathic pain model in rats (n=6 per group). The compound of Example 3 (10 mg/kg i.p.) significantly attenuated tactile allodynia threshold that that of a CB2-selective agonist AM1241 (15 mg/kg i.p.). Administration of the opioid antagonist naloxone (10 mg/kg i.p.) per se did not affect paw withdrawal threshold. Pretreatment with 10 mg/kg naloxone i.p. followed 15 min later by 10 mg/kg of the compound of Example 3i.p. did not affect the antiallodynic effects of the compound of Example 3 (Noloxone+ the compound of Example 3). Reversal of the antiallodynic effects of 15 mg/kg of AM251 i.p. by pretreatment with 10 mg/kg naloxone i.p. *P<0.001 as compared to vehicle and AM1241. $^{+}$P<0.001 as compared to vehicle, naloxone, and naloxone+AM1241 groups. $^{\#}$P<0.01 as compared to vehicle and naloxone+AM1241 groups.

I.p. administration of 15 mg/kg AM1241, a CB2 ligand produced antiallodynic effects that was significantly different (P<0.001) from the vehicle (FIG. 13). Ibrahim, M. M., *Activation of CB2 Cannabinoid Receptors by AM1241 Inhibits Experimental Neuropathic Pain: Pain Inhibition by Receptors Not Present in the CNS*, Proc. Natl. Acad. Sci. U.S.A., 2003, 100:10529-33. However, the antiallodynic effects of 10 mg/kg the compound of Example 3 i.p. was significantly (P<0.001) greater than that observed with 15 mg/kg AM1241 i.p. The antinociceptive effects AM1241 have been shown to be dependent on β-endorphin and μ-opioid receptor system and were blocked by the administration of naloxone or antiserum to β-endorphin. Ibrahim, M. M., et al., *CB2 Cannabinoid Receptor Activation Produces Antinociception by Stimulating Peripheral Release of Endogenous Opioids*, Proc. Natl. Acad. Sci. U.S.A., 2005, 102:3093-8. To investigate whether the antiallodynic effects of the compound of Example 3 are mediated via μ-opioid receptor-dependent activity, SNL rats were injected with the opioid receptor antagonist naloxone (10 mg/kg i.p.) 15 min prior to the administration of the compound of Example 3. Naloxone pretreatment had no effect on the antiallodynic activity of the compound of Example 3 (FIG. 13, P<0.001). However, under similar conditions, pretreatment with naloxone significantly reversed the analgesic effects induced by AM1241 at 15 mg/kg i.p. (FIG. 13, P<0.01).

Prevention of Chemotherapy-induced Peripheral Neuropathy by Cannabinoid Receptor Subtype 2 (CB2) Modulators CB2 agonist is able to suppress neuropathic nociception induced by a chemotherapeutic agent. Prevention of the development of this peripheral neuropathy by pre or co-administration of a CB2 modulator (or any other drug) with a chemotherapeutic agent is provided herein.

Paclitaxel is an antineoplastic drug used in cancer chemotherapy. Paclitaxel is used to treat patients with lung, ovarian, breast, head and neck cancer, and advanced forms of Kaposi's sarcoma. Neuropathic pain is one of the side effects associated with the use of paclitaxel. Mielke, S., et al., *Peripheral neuropathy: a persisting challenge in paclitaxel-based regimes*, Eur J Cancer, 2006, 42:24-30. Neuropathic pain, a debilitating condition characterized by severe, persistent pain that is refractory to traditional analgesia. This side effect is also associated with the use of other antineoplastic agents such as vinca alkaloids (e.g. vincristine), other taxane derivatives or platinum-derivatives (e.g. cisplatin). In the US, the annual healthcare cost attributable to neuropathic pain is almost $40 billion. Turk, D.C., *Clinical effectiveness and cost-effectiveness of treatments for patients with chronic pain*, Clin J Pain, 2002, 18:355-65. There is no effective or satisfactory treatment for neuropathic pain. Warms, C. A., et al., *Treatments for chronic pain associated with spinal cord injuries: many are tried, few are helpful*, Clin J Pain, 2002, 18:154-63.

Chemotherapy-induced neuropathic pain is dose dependent; the mechanism of which might be accompanied by morphological to primary afferent. Recently, CB2 has emerged as a new target for the treatment of neuropathic pain with an added advantage of lacking the psychotropic side effects that are normally seen with the use of the CB1 agonists. Cox, M. L., *The antinociceptive effect of [Delta]9-tetrahydrocannabinol in the arthritic rat involves the CB2 cannabinoid receptor*, European Journal of Pharmacology, 2007, 570:50-56; Beltramo, M., et al., *C2 receptor-mediated antihyperalgesia: possible direct involvement of neural mechanisms*, Eur J Neurosci, 2006, 23:1530-8; Ibrahim, M. M., *CB2 cannabinoid receptor mediation of antinociception*, Pain, 2006, 122:36-42; Guindon, J., et al., *Cannabinoid CB2 receptors: a therapeutic target for the treatment of inflammatory and neuropathic pain*, Br J Pharmacol, 2007.

Peripheral nerve injury induces CB2 protein expression in rat sensory neurons. Wotherspoon, G., *Peripheral nerve injury induces cannabinoid receptor 2 protein expression in rat sensory neurons*, Neuroscience, 2005, 135:235-45. CB2 mRNA is expressed in dorsal root ganglia (DRG) of neuropathic rats and is up-regulated in the spinal cord of neuropathic rats. CB2 mRNA expression was also shown in cultured spinal cord microglia and are upregulated in reactive microglia. Beltramo, M., *CB2 receptor-mediated antihyperalgesia: possible direct involvement of neutral mechanicms*, Eur J Neurosci, 2006, 23:1530-8; Ashton, J. C., *Class M: The Cannabinoid CB2 Receptor as a Target for Inflammation-Dependent Neurodegeneration*, Current Neuropharmacology, 2007, 5:73-80; Romero-Sandoval, A., et al., *Spinal Cannabinoid Receptor Type 2 Activation Reduces Hypersensitivity and Spinal Cord Glial Activation after Paw Incision*, Anesthesiology, 2007, 106:787-794.

CB2 agonists are neuroprotective and are emerging as a target for treating demyelinating diseases such as multiple sclerosis. Arevalo-Martin, A., et al., *CB(2) cannabinoid receptors as an emerging target for demyelinating diseases: from neuroimmune interactions to cell replacement strategies*, Br J Pharmacol, 2007. For instance, treatment with a selective CB2 agonist JWH-015 not only switched microglial cells morphology toward normal in the spinal cord of Theiler's murine encephalomyelitis virus-infected mice, but also significantly improved the neurological recovery and remyelination process. Arevalo-Martin, A., et al., *Therapeutic action of cannabinoids in a murine model of multiple sclerosis*, J Neurosci 2003, 23:2511-6. Cannabinoids abrogated major histocompatibility complex class II antigen expression, and decreased the number of CD4-infiltrating T cells. This protective mechanism of CB2 agonists has been attributed to reduction in the release of inflammatory cytokines or reactive oxygen species and/or increase in the production of protective molecules such as TGFa or anti-inflammatory cytokines such as IL-10. Sagrego, O., et al., *Cannabinoids and neuroprotection in basal ganglia disorders*, Mol Neurobiol, 2007, 36:82-91.

The use of CB2 agonists produce a dose-dependent reduction in mechano-allodynia and mechano-hyperalgesia in paclitaxel-treated rats, and the duration of effect is dependent on the duration of action of the CB2 agonist studied. There is evidence that a non-specific cannabinoid agonist with both CB1 and CB2 activities was able to prevent mechanical allodynia induced by cisplatinum. Vera, G., et al., *WIN 55, 212-2 prevents mechanical allodynia but not alterations in feeding behaviour induced by chronic cisplatin in the rat*, Life Sci, 2007, 81:468-79. Provided herein is a treatment that prevents the development of chemotherapy induced-peripheral neuropathy. Administration of the compound of Example 3, a novel CB2 selective agonist, prevented the development of neuropathic pain induced by paclitaxel.

(A) Paclitaxel-Induced Neuropathy

First, an experiment was performed to demonstrate that paclitaxel can produce the rat model of paclitaxel-induced neuropathy. A mixture of saline and CREMOPHOR® ELP 10% was used as vehicle for paclitaxel. It was injected at a concentration of 1.0 mg/kg intraperitoneally to the chemotherapy-treated group of rats on 4 consecutive days for a final cumulative dose of 4 mg/kg to 18 rats.

Figure 17:
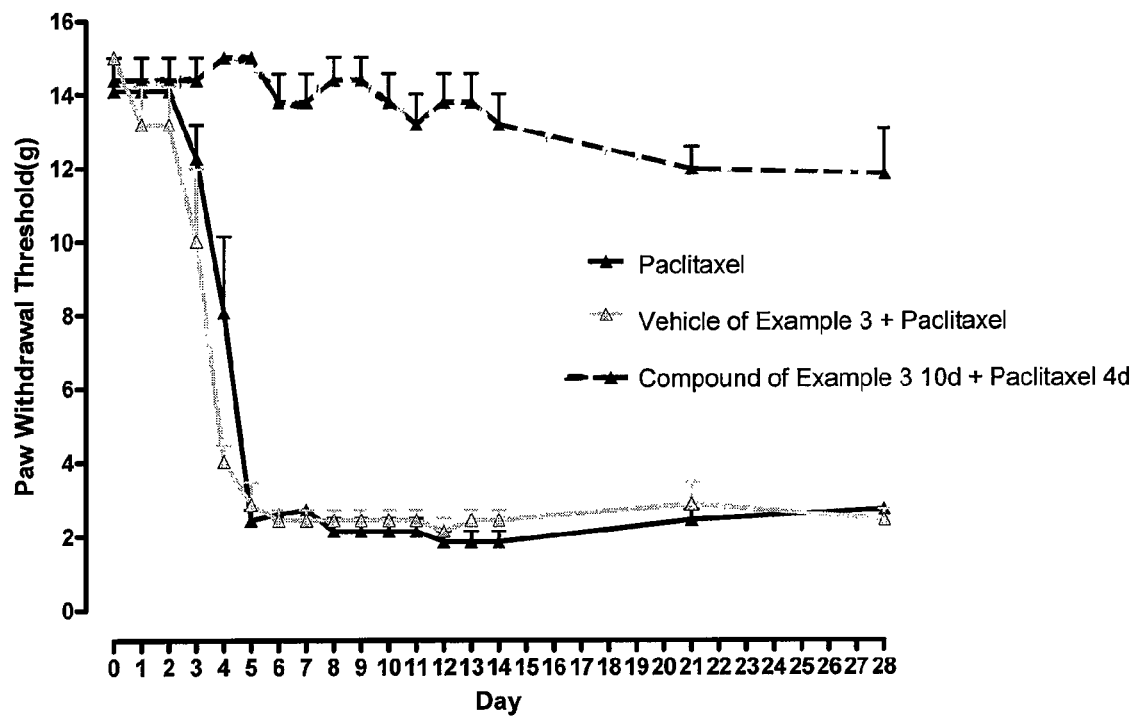
FIG. 17 shows the effects of the compound of Example 3 on Paclitaxel-induced neuropathy in rats (right paw). Peripheral neurophathy started to develop within a few days of paclitaxel administration, but was prevented by administration of the compound of Example 3.
Figure 18:
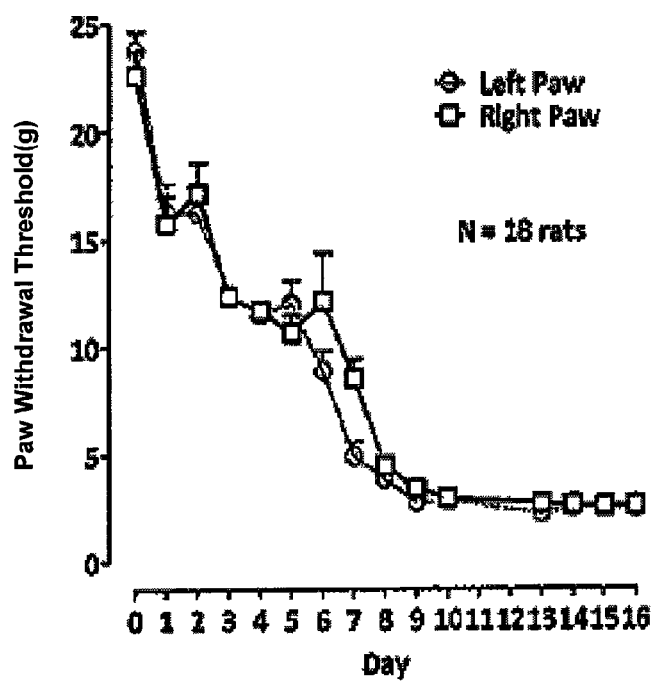
FIG. 18 illustrates paclitaxel-induced peripheral neuropathy in rats. The peripheral neuropathy started to develop within a few days of paclitaxel administration and reached a plateau by the 10th day.

Assessment of neuropathic pain. Paw withdrawal thresholds were determined daily in both hind paws of each animal using calibrated von Frey monofilaments according to an up-down procedure. A series of von Frey filaments with exponentially incremental degrees of stiffness (0.4, 0.7, 1.2, 2.0, 3.6, 5.5, 8.5, and 15.1 g) was used to measure the 50% threshold for both hindpaw withdrawal in awake, unrestrained rats. Chaplan, S.R., *Quantitative assessment of tactile allodynia in the rat paw*, Journal of Neuroscience Methods, 1994, 53:55-63. Brisk paw withdrawal from the pressure of a filament gently bent against the plantar surface of the paw was defined as a positive response, and absence of withdrawal within 6 sec was considered a negative response. The series of filaments touched the hindpaw in sequential ascending or descending order of stiffness until the threshold of response was crossed (allowing about 10 sec between each increment). Each time the threshold was crossed, the direction of stimulus presentation was reversed and the procedure resumed. Four responses were collected after the first threshold detection, and the 50% withdrawal thresholds was interpolated. In cases in which the response thresholds fall outside the range of detection, 15.1 and 0.25 g were assigned for continuous negative or positive responses, respectively, to the limits of stimulation. FIG. 17 and FIG. 18 show results from these experiments and that peripheral neuropathy started to develop within a few days. FIG. 18 reflects that a plateau was reached by the 10th day.

B) Prevention of Neuropathy Induced by Paclitaxel

These experiments were designed to show that the administration of the compound of Example 3, 30 minutes prior to the administration of paclitaxel will prevent the development of neuropathy. Group 1 of rats received paclitaxel for four days, as described immediately above in subpart (A) titled "Paclitaxel-induced Neuropathy." In group 2, a dose of 15 mg/kg of the compound of Example 3, injected intraperitoneally was administered 30 minutes prior to the administration of paclitaxel. In group 3, vehicle of the compound of Example 3 was administered 30 min prior to the administration of paclitaxel. Paw withdrawal thresholds were determined daily in both hind paws of each animal using calibrated von Frey monofilaments according to an up-down procedure as described immediately above in subpart (A) titled "Paclitaxel-induced Neuropathy." The results are shown in FIG. 17.

Figure 19A:
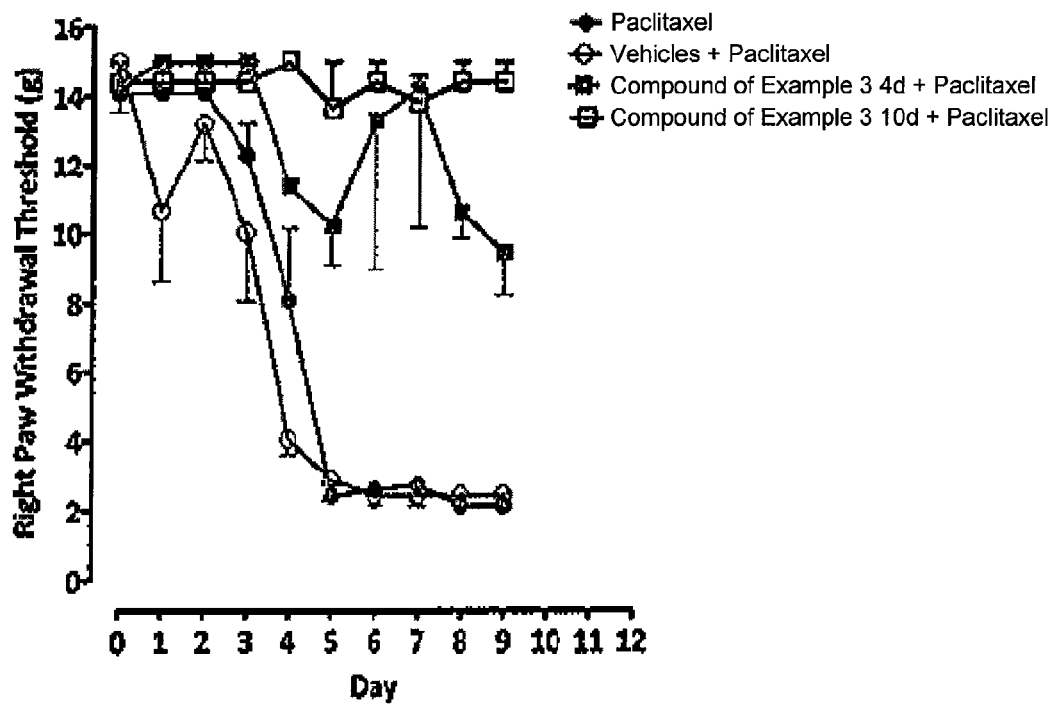
FIGS. 19A and 19B show the effects of the compound of Example 3 on paclitaxel-induced neuropathy in rats. Group 1 of the rats received paclitaxel for four days, as did the rats in FIG. 18. In groups 2 to 4, 0.25 mL of the compound of Example 3 or the vehicle, a mixture of NMP, propylene glycol, and chromophore ELP (25%,25%,10%) in sterile water were administered 30 min prior to the administration of paclitaxel. Groups 2 and 4 continued to receive either the vehicle (group 2) or the compound of Example 3 (group 4) daily for 11 more days. Paw withdrawal thresholds were determined daily in both hind paws of each animal using calibrated von Frey monofilaments according to an up-down procedure. As shown, continued administration of 15 mg/kg of the compound of Example 3 intraperitoneally (IP) daily completely prevented the development of paclitaxel-evoked mechano-allodynia. Administration of 15 mg/kg of the compound of Example 3 IP for 4 days only did not prevent but significantly prevented the severity of paclitaxel-evoked mechano-allodynia
Figure 19B:
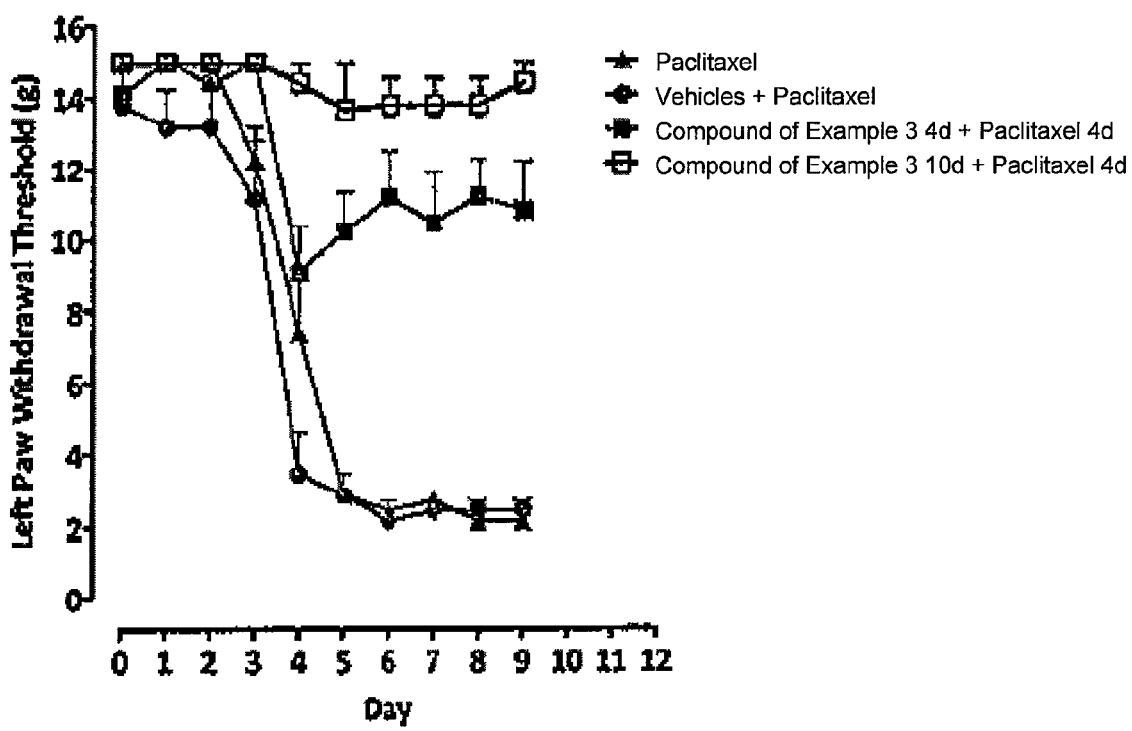

FIGS. 19A and 19B show results from an experiment in which three groups of rats were administered 0.25 mL of the compound of Example 3 or the vehicle, a mixture of NMP, propylene glycol, chromophore ELP (25%,25%,10%) in sterile water 30 min prior to the administration of paclitaxel. Two of the three experimental groups continued to receive either the vehicle or the compound of Example 3 daily for 11 more days. Paw withdrawal thresholds were determined daily in both hind paws of each animal using calibrated von Frey monofilaments according to an up-down procedure as described immediately above in subpart (A) titled "Paclitaxel-induced Neuropathy." A fourth group of rats received paclitaxel for four days, as described immediately above in subpart (A) titled "Paclitaxel-induced Neuropathy." As shown in FIGS. 19A and 19B, continued administration of 15 mg/kg the compound of Example 3 intraperitoneally (IP) daily completely prevented the development of paclitaxel-evoked mechano-allodynia. Administration of 15 mg/kg of the compound of Example 3 for 4 days only did not prevent but significantly prevented the severity of paclitaxel-evoked mechano-allodynia.

Figure 14A:
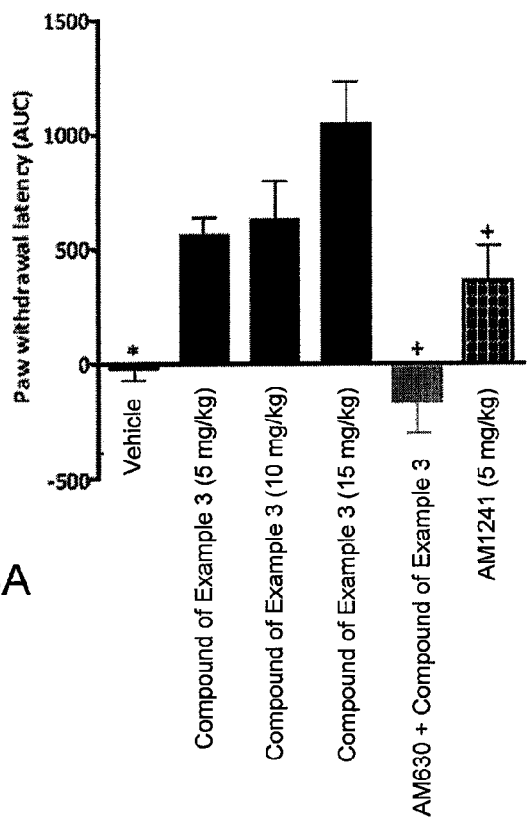
FIGS. 14A, 14B, 14C and 14D show the effects of the compound of Example 3 (i.p) on thermal hyperalgesia and tactile allodynia in a paclitaxel-induced neuropathic pain model in rats (n=8 per group).
Figure 14B:
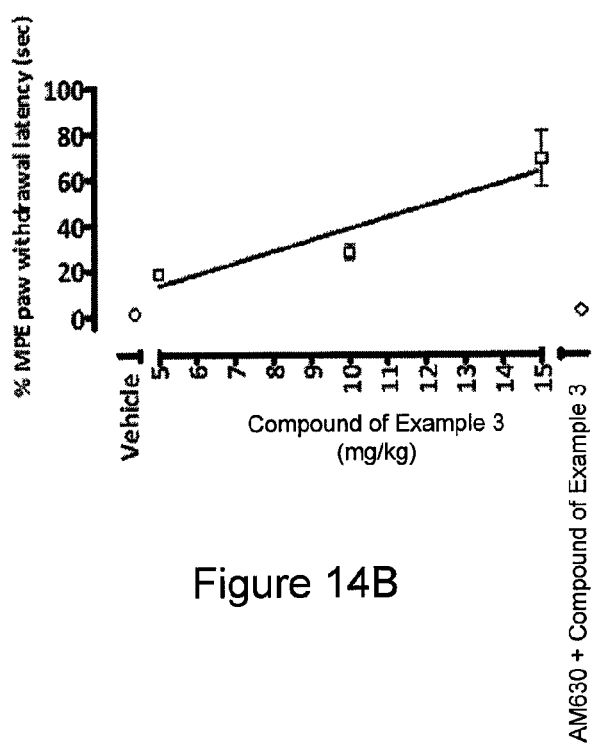
Figure 14C:
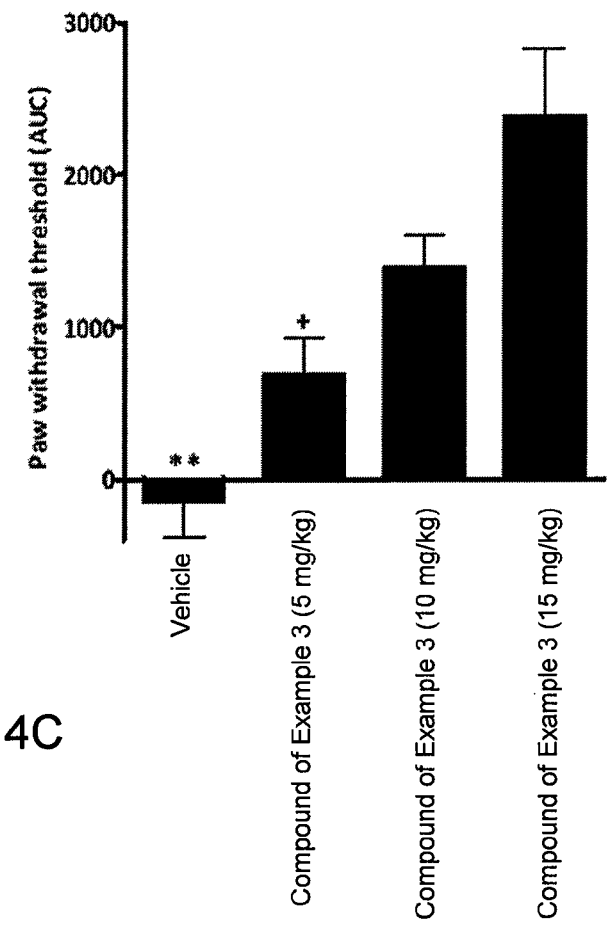
Figure 14D:
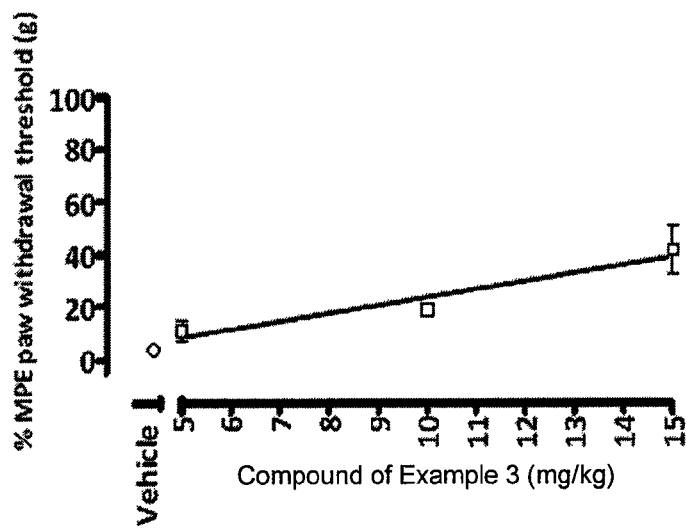

Effects of the Compound of Example 3 on Tactile Allodynia in a Paclitaxel-Induced Neuropathic Pain Model Tactile allodynia was developed in 100% of rats 10 days after the start of paclitaxel administration as demonstrated by a reduction in paw withdrawal threshold to mechanical stimulation to 2.9±0.19 g and 2.8±0.15 g for the right and left paws, respectively using Von Frey filaments (FIG. 10B). The compound of Example 3 suppressed paclitaxel-evoked thermal hyperalgesia (FIGS. 14A and 14B) and mechanical allodynia (FIGS. 14C and 14D) relative to treatment with vehicle in a dose-dependent manner. This suppression was maximal at 20 min. The calculated $ED_{50}$ of the compound of Example 3 for suppressing thermal hyperalgesia at 20 min was 13.5 mg/kg i.p. (95% CI=8.2-22 mg/kg) (FIG. 14B). Pretreatment with AM630 (5 mg/kg i.p.) significantly reversed anti-hyperalgesic effects induced by i.p. administration of 15 mg/kg the compound of Example 3 administered 15 min later (P<0.001) (FIG. 14A). The effect of 5 mg/kg AM1241 i.p. on reversing thermal hyperalgesia was significantly less than (P<0.05) that noted for 15 mg/kg the compound of Example 3i.p. (FIG. 14A). The compound of Example 3 dose-dependently attenuated tactile allodynia in this model, which is seen as an increase in the % MPE withdrawal threshold AUC (FIG. 14C) with an $ED_{50}$ of 24 mg/kg i.p. (FIG. 14D).

Figure 15:
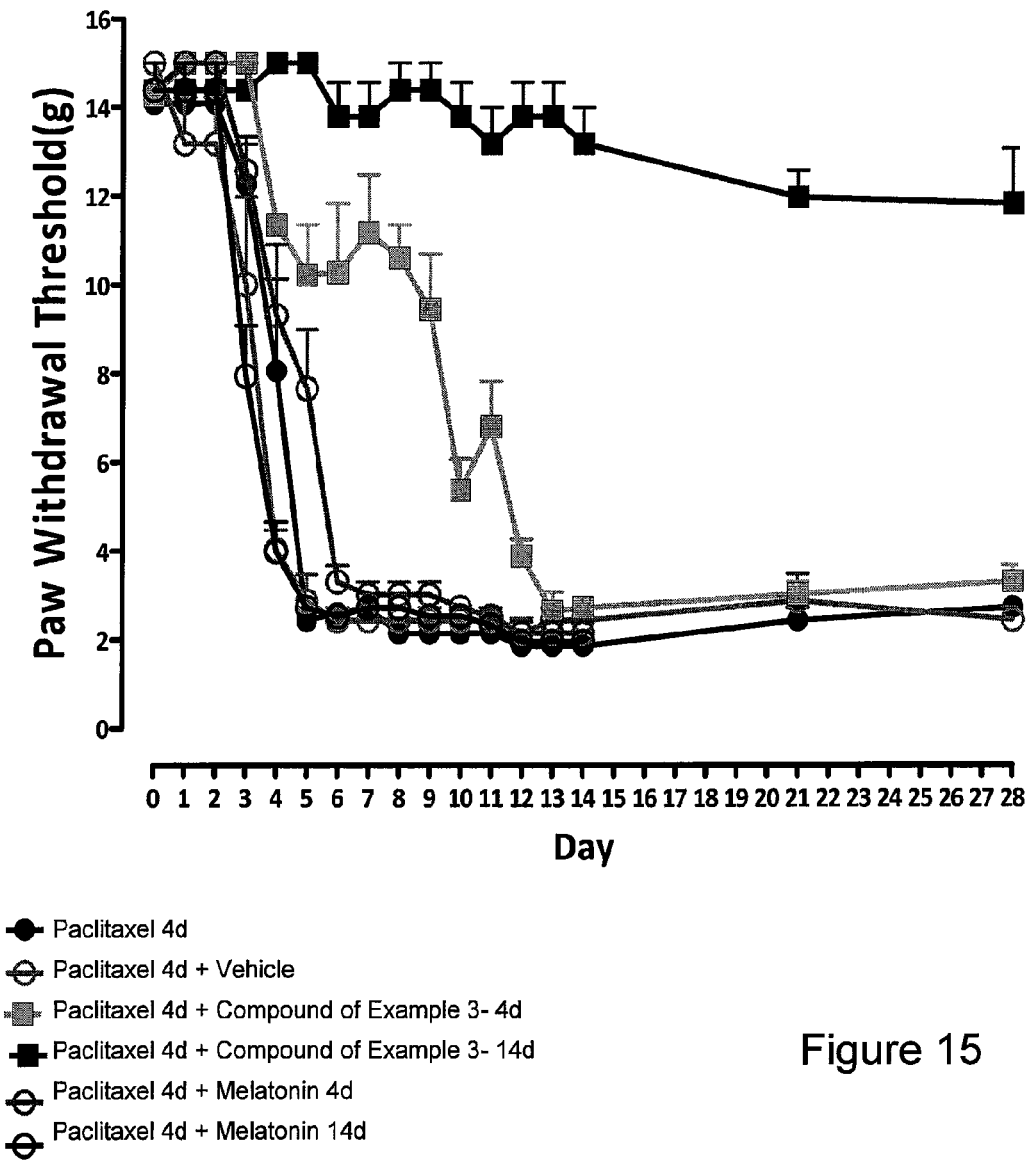
FIG. 15 shows after the administration of the compound of Example 3 with the start of paclitaxel administration for 14 days [four days concomitant with the administration of paclitaxel and continued for further 10 days] resulted in prevention of paclitaxel-induced neuropathy in 100% of rats. Administration of paclitaxel alone of 4 days resulted in development of neuropathy in 100 percent of rats. The compound of Example 3 for four days only resulted in short-lived prevention of paclitaxel-induced neuropathy. Melatonin did not provide any protection against neuropathy in this model.
Figure 16A:
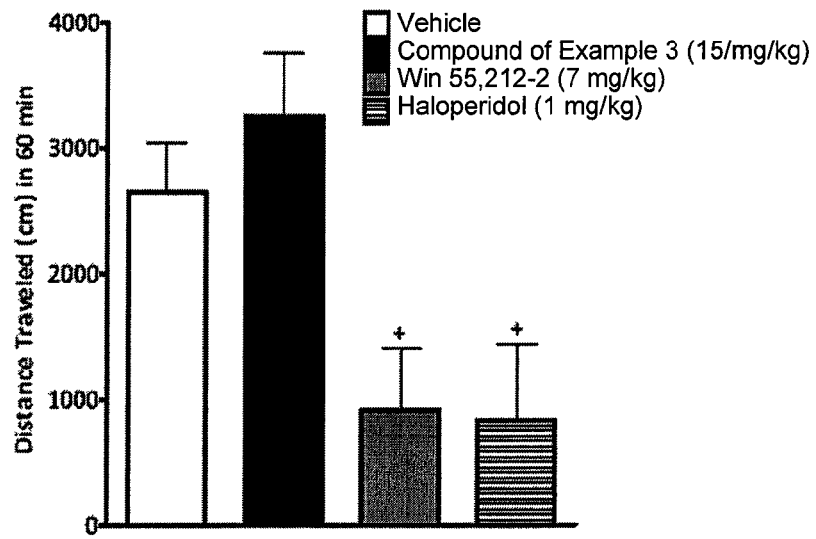
FIGS. 16A, 16B, 16C and 16D show the absence of psychoactive cannabinoid effect of the compound of Example 3. Exploratory behavior was tested in the open field following i.p. administration of vehicle, the compound of Example 3, WIN 55,212-2, and haloperidol (n=6 per group). The following parameters were scored for 60 minutes: distance traveled (FIG. 16A), ambulatory time (FIG. 16B), vertical activity (FIG. 16C), and number of zone entries (FIG. 16D). $^+P<0.05$ versus vehicle and the compound of Example 3. $^*P<0.05$ versus the compound of Example 3.
Figure 16B:
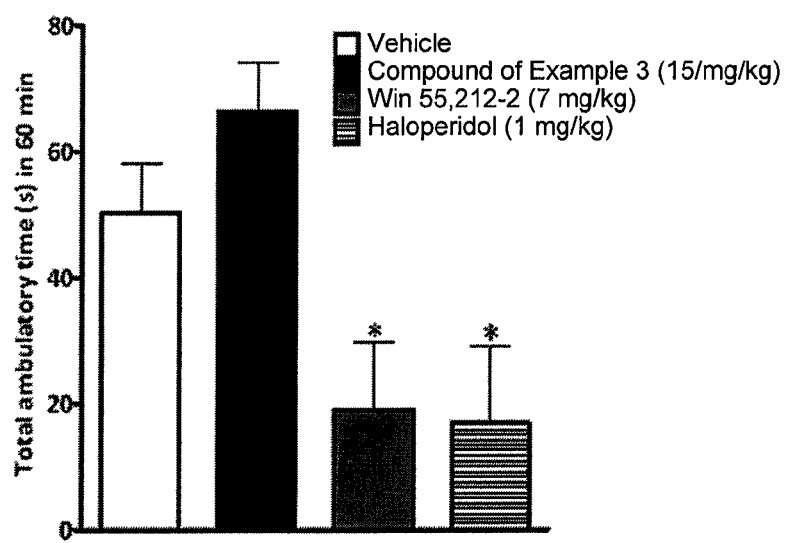
Figure 16C:
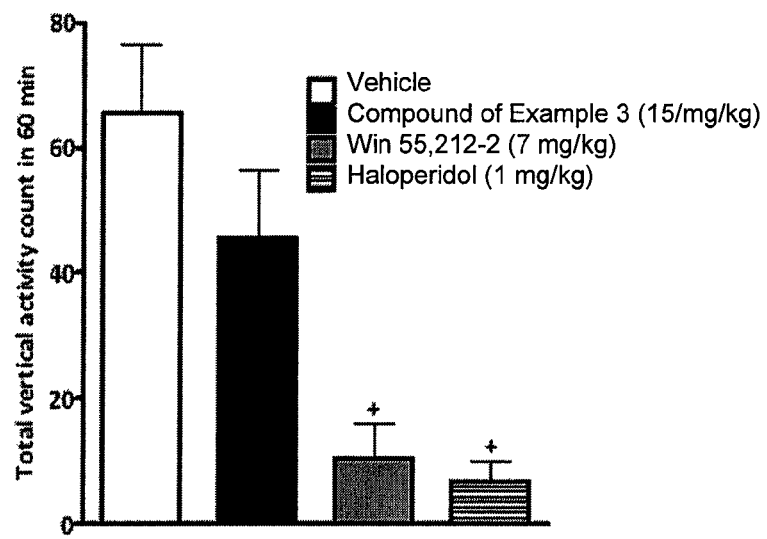
Figure 16D:
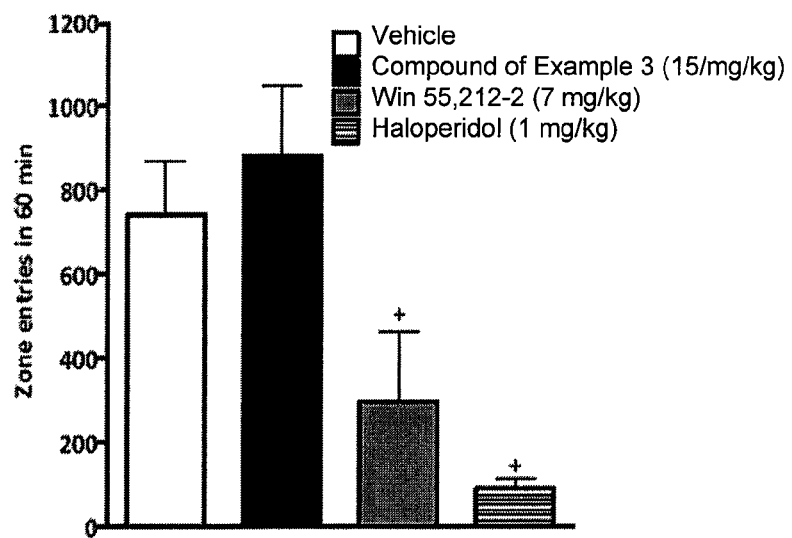

Administration of the Compound of Example 3 Prevents the Development of Neuropathy Associated With Paclitaxel Administration Administration of the compound of Example 3 with the start of paclitaxel administration for 14 days [4 days concomitant with the administration of paclitaxel and continued for further 10 days] resulted in prevention of paclitaxel-induced neuropathy in 100% of rats (FIG. 15). Administration of the compound of Example 3 for four days only resulted in short-lived prevention of paclitaxel-induced neuropathy. Melatonin did not provide any protection against neuropathy in this model.

Open Field Chamber Testing

In contrast to the compound of Example 3 (15 mg/kg i.p.), administration of 7 mg/kg WIN 55, 212-2 i.p and 1 mg/kg haloperidol i.p. significantly (P<0.05) decreased exploratory behavior in rats, as evidenced by a reduction in the total distance traveled (FIG. 10A), time spent ambulating (FIG. 10B), rearing in the open field (FIG. 10C), and zone entries (FIG. 10D). Herzberg, U., et al., *The Analgesic Effects of R(+)-WIN 55, 212-2 Mesylate, a High Affinity Cannabinoid Agonist, in a Rat Model of Neuropathic Pain*, Neurosci Lett, 1997, 221:157-60.

We claim the following:

1. A compound, or pharmaceutically acceptable salt thereof selected from the group consisting of:

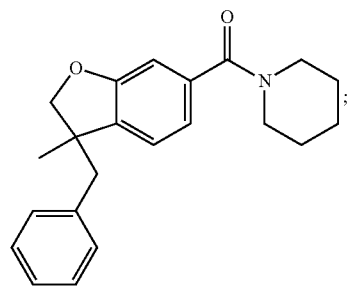

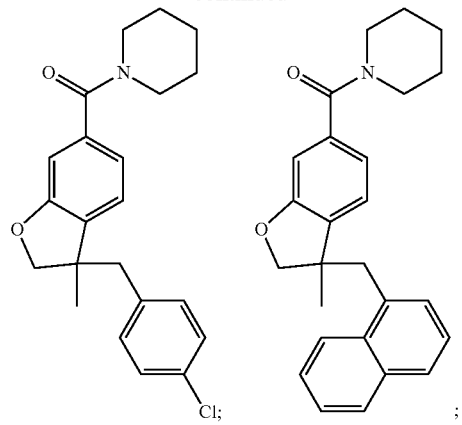

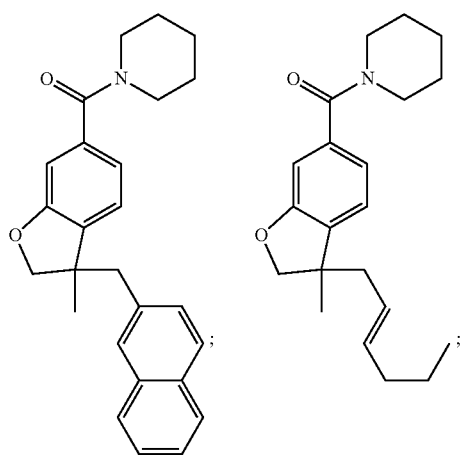

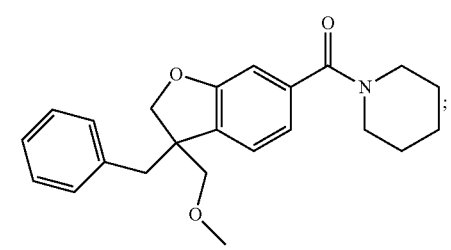

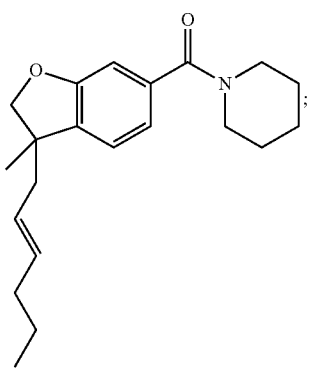

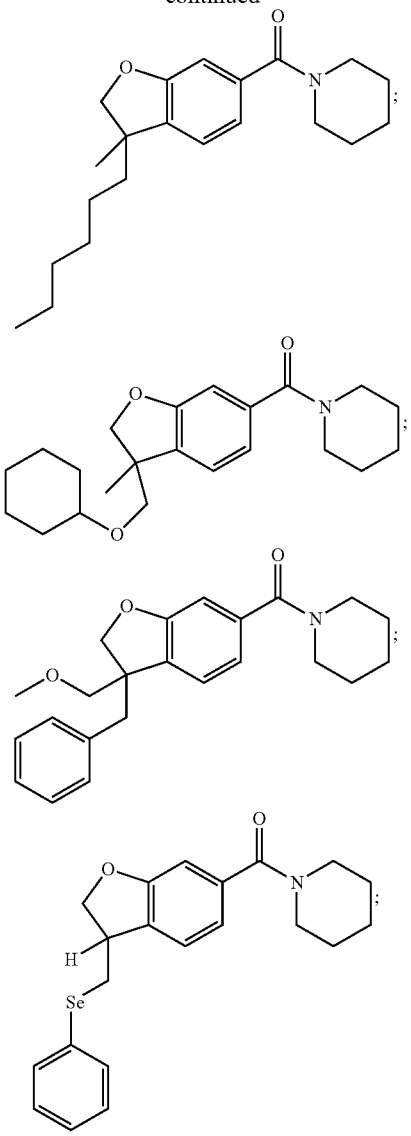
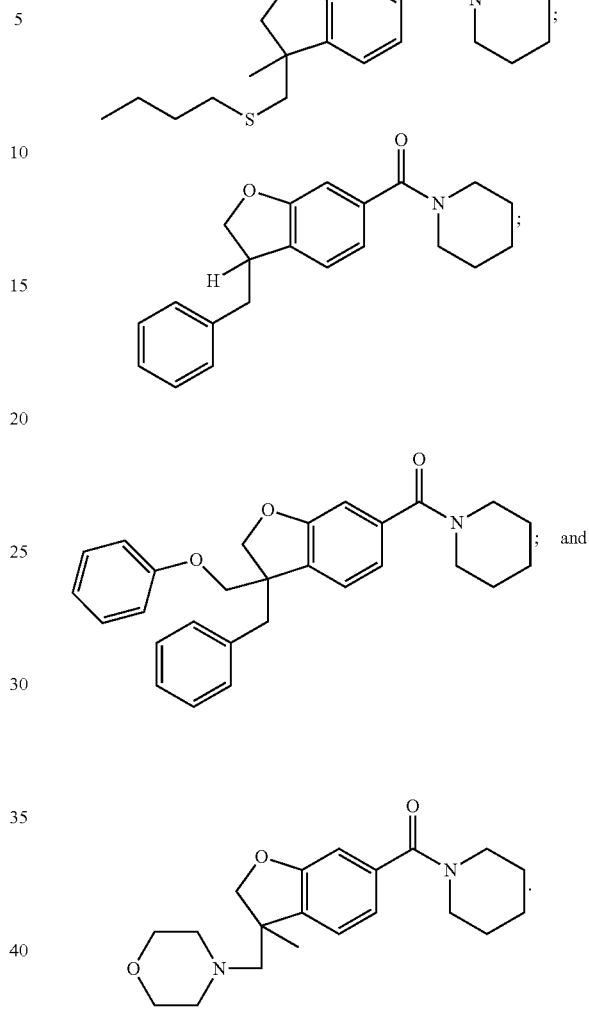
* * * * *